United States Patent
Jansen et al.

(10) Patent No.: US 10,548,906 B2
(45) Date of Patent: Feb. 4, 2020

(54) METHODS OF PROMOTING HEPATIC REGENERATION

(71) Applicant: Intercept Pharmaceuticals, Inc., New York, NY (US)

(72) Inventors: Peter Leonardus Maria Jansen, Haren (NL); Stephanus Willibrordus Maria Olde Damink, Margraten (NL); Franciscus Gerardus Schaap, El Bunde (NL); Isabelle Anne Leclercq, Brussels (BE)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/760,769

(22) PCT Filed: Sep. 21, 2016

(86) PCT No.: PCT/US2016/052886
§ 371 (c)(1),
(2) Date: Mar. 16, 2018

(87) PCT Pub. No.: WO2017/053428
PCT Pub. Date: Mar. 30, 2017

(65) Prior Publication Data
US 2018/0256602 A1    Sep. 13, 2018

Related U.S. Application Data

(60) Provisional application No. 62/221,324, filed on Sep. 21, 2015.

(51) Int. Cl.
*A61K 31/575* (2006.01)
*A61P 1/16* (2006.01)

(52) U.S. Cl.
CPC .............. *A61K 31/575* (2013.01); *A61P 1/16* (2018.01)

(58) Field of Classification Search
None
See application file for complete search history.

(56) References Cited

U.S. PATENT DOCUMENTS

| | | |
|---|---|---|
| 7,786,102 B2 | 8/2010 | Pellicciari |
| 7,932,244 B2 | 4/2011 | Pellicciari et al. |
| 7,994,352 B2 | 8/2011 | Ferrari et al. |
| 2014/0057886 A1 | 2/2014 | Pellicciari et al. |
| 2014/0206657 A1 | 7/2014 | Yu et al. |
| 2014/0371190 A1 | 12/2014 | Pellicciari |

FOREIGN PATENT DOCUMENTS

| WO | WO 2008/002573 A2 | 1/2008 |
|---|---|---|
| WO | WO 2015/075557 A2 | 5/2015 |

OTHER PUBLICATIONS

Borude et al. "Hepatocyte-Specific Deletion of Farnesoid X Receptor Delays But Does Not Inhibit Liver Regeneration After Partial Hepatectomy in Mice", Hepatology, 2012, vol. 56, No. 6, p. 2344-2352.
Boyer et al. "Upregulation of a basolateral FXR-dependent bile acid efflux transporter OSTα-OSTβ in cholestasis in humans and rodents", Am J Physiol Gastrointest Liver Physiol, 2006, 290, p. G1124-G1130.
Chen et al. "Farnesoid X Receptor Alleviates Age-Related Proliferation Defects in Regenerating Mouse Livers by Activating Forkhead Box m1b Transcription", Hepatology, 2010, vol. 51, No. 3, p. 953-962.
Chen et al. "Oleanolic acid attenuates obstructive cholestasis in bile duct-ligated mice, possibly via activation of NRF2-MRPs and FXR antagonism", European Journal of Pharmacology, 2015, vol. 765, p. 131-139.
Dai G, et al. "Pregnane X Receptor is Essential for Normal Progression of Liver Regeneration", Hepatology, 2008, vol. 47, No. 4, p. 1277-1287.
Dai J. et al. "Impact of bile acids on the growth of human cholangiocarcinoma via FXR", Journal of Hematology & Oncology, 2011, vol. 4, p. 41-48.
D'Aldebert E. et al. "Bile Salts Control the Antimicrobial Peptide Cathelicidin Through Nuclear Receptors in the Human Biliary Epithelium", Gastroenterology, 2009, vol. 136, p. 1435-1443.
De Graaf W. et al. "Increase in future remnant liver function after preoperative portal vein embolization", British Journal of Surgery, 2011, vol. 98, p. 825-834.
De Meijer V.E. et al. "Systematic review and meta-analysis of steatosis as a risk factor in major hepatic resection", British Journal of Surgery, 2010, vol. 97, p. 1331-1339.
Dixon "Factors affecting morbidity and mortality after surgery for obstructive jaundice: a review of 373 patients", Gut. 1983, vol. 24, p. 845-852.

(Continued)

*Primary Examiner* — Brian J Davis
(74) *Attorney, Agent, or Firm* — Michelle Iwamoto-Fan; Intercept Pharmaceuticals, Inc.

(57) ABSTRACT

The present invention relates to methods of accelerating, promoting or increasing hepatic regeneration, or increasing liver mass in a subject, by using a compound of formula (A): or a pharmaceutically acceptable salt thereof, and wherein R1, R2, R3, R4, R5, R6, m, and n are as described herein.

(A)

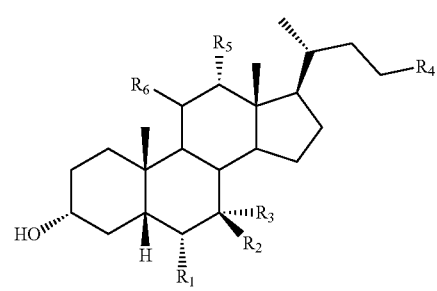

19 Claims, 35 Drawing Sheets

(56) References Cited

OTHER PUBLICATIONS

Fickert et al. "Ursodeoxycholic Acid Aggravates Bile Infarcts in Bile Duct-Ligated and Mdr2 Knockout Mice via Disruption of Cholangioles", Gastroenterology, 2002, vol. 123, p. 1238-1251.

Fiorucci et al. "Targeting FXR in cholestasis: hype or hope", Expert Opinion Ther. Targets, 2014, vol. 18, No. 12, p. 1450-1459.

Fiorucci et al. "Protective Effects of 6-Ethyl Chenodeoxycholic Acid, a Farnesoid X Receptor Ligand, in Estrogen-Induced Cholestasis", The Journal of Pharmacology and Experimental Pharmaceutics, 2005, vol. 323, No. 2, p. 604-612.

Fong et al. "Tyrosine Phosphorylation of Sprouty2 Enhances its Interaction with c-Cbl and is Crucial for its Function", The journal of Biological Chemistry, 2003, vol. 278, No. 35, Issue of Aug. 29, pp. 33456-33464.

Farges et al. "Multicentre European study of preoperative biliary drainage for hilar cholangiocarcinoma", 2013, British Journal of Surgery, vol. 100, p. 274-283.

Farrell et al. "Risk of HAART Therapy in Hepatitis C", Hepatology, 2002, vol. 32, No. 3, p. 730-734.

Fausto et al. "Liver Regeneration", Hepatology, 2006, p. S45-S53.

Geier et al. "Principles of hepatic organic anion transporter regulation during cholestasis, inflammation and liver regeneration", Biochimica et Biophysica Acta, 2007, vol. 1773, p. 283-308.

Geier et al. "Cytokine-Independent Repression of Rodent Ntcp in Obstructive Cholestasis", 2005, Hepatology, vol. 41, No. 3, p. 470-477.

Heger M. et al. "Non-invasive Quantification of Triglyceride Content in Steatotic Rat Livers by 1H-MRS: When Water Meets (Too Much) Fat", Academic Radiology, 2011, vol. 18, No. 12, p. 1582-1592.

Hirschfield G. et al. "Efficacy of Obeticholic Acid in Patients With Primary Biliary Cirrhosis and Inadequate Response to Ursodeoxycholic Acid", Gastroenterology, 2015, vol. 148, p. 751-761.

Ho H. et al. "Fibroblast growth factor receptor 4 regulates proliferation, anti-apoptosis and alpha-fetoprotein secretion during hepatocellular carcinoma progression and represents a potential target for therapeutic intervention", Journal of Hepatology 50, 2009, vol. 50, p. 118-127.

Hoekstra, L. et al. "Bile salts predict liver regeneration in rabbit model of portal vein embolization", Journal of Surgical Research, 2012, vol. 178, p. 773-778.

Huang W. et al. "Nuclear Receptor-Dependent Bile Acid Signaling is Required for Normal Liver Regeneration", Science, 2006, vol. 312, No. 5771, p. 233-236.

Hubert C. et al. "Hepatic regeneration in a rat model is impaired by chemotherapy agents used in metastatic colorectal cancer", Science Direct, 2015, vol. 41, p. 1471-1478.

Inagaki T. et al. "Fibroblast growth factor 15 functions as an enterohepatic signal to regulate bile acid homeostasis", Cell Metabolism, 2005, vol. 2, p. 217-225.

Jung D. et al. "Role of liver-enriched transcription factors and nuclear receptors in regulating the human, mouse, and rat NTCP gene", Am J Physiol Gastrointest Liver Physiol, 2004, vol. 286: G752-G761.

Keppler "The Roles of MRP2, MRP3, OATP1B1, and OATP1B3 in Conjugated Hyperbilirubinemia", Drug Metab Dispos, 2014, vol. 42, p. 561-565.

Kloek J. et al. "Biliary drainage attenuates postischemic reperfusion injury in the cholestatic rat liver", Surgery, 2008, vol. 144, No. 1, p. 22-31.

Kloek J. et al. "Cholestasis enhances liver ischemia/reperfusion-induced coagulation activation in rats", Hepatology Research, 2010, vol. 40, p. 204-215.

Kokudo N. et al. "Proliferative Activity of Intrahepatic Colorectal Metastases After Preoperative Hemihepatic Portal Vein Embolization", Hepatology, 2001, p. 267-272.

Kong B. et al. "Fibroblast growth factor 15 deficiency impairs liver regeneration in mice", Am J Physiol Gastrointest Liver Physiol, 2014, vol. 306, p. G893-G902.

Landrier et al. "The nuclear receptor for bile acids, FXR, transactivates human organic solute transporter-α and -β genes", Am J Physiol Gastrointest Liver Physiol, 2006, vol. 290, No. 3, p. G476-G485.

Li S. et al. "Cytoplasmic Tyrosine Phosphatase Shp2 Coordinates Hepatic Regulation of Bile Acid and FGF15/19 Signaling to Repress Bile Acid Synthesis", Cell Metabolism, 2014, vol. 20, p. 320-332.

Lionarons et al. "Simple steatosis sensitizes cholestatic rats to liver injury and dysregulates bile salt synthesis and transport", Scientific Reports, 2016, vol. 6, p. 31829 (10 pages).

Liu Y. et al. "Hepatoprotection by the farnesoid X receptor agonist GW4064 in rat models of intra- and extrahepatic cholestasis", Journal of Clinical Invest., 2003, vol. 112, No. 11, p. 1678-1687.

Luo J. et al. "A nontumorigenic variant of FGF19 treats cholestatic liver diseases", Science Translational Medicine, 2014, vol. 6, Issue 247, p. 247ra100 (12 pages).

Marsman H. et al. "Hepatic regeneration and functional recovery following partial liver resection in an experimental model of hepatic steatosis treated with omega-3 fatty acids", British Journal of Surgery, 2013, vol. 100, p. 674-683.

Michalopoulos G. et al. "Liver Regeneration", Science, 1997, vol. 276, p. 60-66.

Mwaoka Y. et al. "Hypertrophy and Unconventional Cell Division of Hepatocytes Underlie Liver Regeneration", Current Biology, 2012, vol. 22, 1166-1175.

Modica S. et al. "Nuclear Bile Acid Receptor FXR Protects against Intestinal Tumorigenesis", Cancer Research, 2008, vol. 68, p. 9589-9594.

Modica S. et al. "Selective Activation of Nuclear Bile Acid Receptor FXR in the Intestine Protects Mice Against Cholestasis", Gastroenterology, 2012, vol. 142, p. 355-365.

Moschetta et al. 'The FXR-FGF19 Gut-Liver Axis as a Novel "Hepatostat"', Gastroenterology, 2015, vol. 149, No. 3, p. 537-540.

Naugler W. "Bile Acid Flux is Necessary for Normal Liver Regeneration", PLOS One, 2014, vol. 9, No. 5, p. e97426 (10 pages).

Naugler et al. "Fibroblast Growth Factor Signaling Controls Liver Size in Mice With Humanized Livers", Gastroenterology, 2015, vol. 149, No. 3, p. 728-740.

Neuschwander-Tetri et al. "Farnesoid X nuclear receptor ligand obeticholic acid for non-cirrhotic, non-alcoholic steatohepatitis (FLINT): a multicentre, randomised, placebo-controlled trial", Lancet, 2015, vol. 385, p. 956-965.

O'Grady J. et al. "Acute liver failure", Postgrad Med Journal, 2005, vol. 81, p. 148-154.

O'Grady J. et al. "Acute liver failure: redefining the syndromes ", The Lancet, 1993, vol. 342, p. 273-275.

Oldhafer et al. "ALPPS—Where Do We Stand, Where Do We Go?", Annals of Surgery, 2016, vol. 263, No. 5, p. 839-841.

Olthof et al. "IL-23 and IL-17A are not involved in hepatic/ischemia reperfusion injury in mouse and man", Journal of Clinical and Translational Research, 2015, vol. 1, No. 3, p. 180-189.

Olthof et al. "Obeticholic acid accelerates liver regeneration following portal vein embolization in a rabbit model", HPB, 2016, vol. 18 (Supplement 1), p. e289-290.

Padrissa-Altes S. et al. "Control of hepatocyte proliferation and survival by Fgf receptors is essential for liver regeneration in mice", Gut, 2015, vol. 64, p. 1444-1453.

Ramakers et al. "Assumption-free analysis of quantitative real-time polymerase chain reaction (PCR) data", Neuroscience Letters, 2003, vol. 339, p. 62-66.

Reddy S. et al. "Underlying Steatohepatitis, But Not Simple Hepatic Steatosis, Increases Morbidity After Liver Resection: A Case-Control Study", Hepatology, 2012, vol. 56, p. 2221-2230.

Reimers et al. "Reactive Oxygen and Nitrogen Species in Steatotic Hepatocytes: A Molecular Perspective on the Pathophysiology of Ischemia-Reperfusion Injury in the Fatty Liver", Antioxidants & Redox Signaling, 2013, vol. 21, No. 7, p. 1119-1142.

Roda "Semisynthetic Bile Acid FXR and TGR5 Agonists: Physicochemical Properties, Pharmacokinetics, and Metabolism in the Rat", The journal of Pharmacology and Experimental Therapeutics, 2014, vol. 350, p. 56-68.

(56) References Cited

OTHER PUBLICATIONS

Schaap F. et al. "High Expression of the Bile Salt-Homeostatic Hormone Fibroblast Growth Factor 19 in the Liver of Patients with Extrahepatic Cholestasis", Hepatology, 2009, vol. 49, No. 4, p. 1228-1235.

Shindoh J. et al. "Analysis of the Efficacy of Portal Vein Embolization for Patients with Extensive Liver Malignancy and Very Low Future Liver Remnant Volume, Including a Comparison with the Associating Liver Partition with Portal Vein Ligation for Staged Hepatectomy Approach", J Am Coll Surg, 2013, vol. 217, No. 1, p. 126-133.

Shirabe K. et al. "Human early liver regeneration after hepatectomy in patients with hepatocellular carcinoma: special references to age", Scandinavian Journal of Surgery, 2013, vol. 102, p. 101-105.

Simoneau E. et al. "Portal vein embolization and its effect on tumour progression for colorectal cancer liver metastases", BJS, 2015, vol. 102, p. 1240-1249.

Stedman S. et al. "Benefit of farnesoid X receptor inhibition in obstructive cholestasis", PNAS, 2006, vol. 103, No. 30, p. 11323-11328.

Uriarte et al. "Identification of fibroblast growth factor 15 as a novel mediator of liver regeneration and its application in the prevention of post-resection liver failure in mice", Gut, 2013, vol. 62, No. 6, p. 899-910.

Van Den Esschert et al. "Liver Regeneration After Portal Vein Embolization Using Absorbable and Permanent Embolization Materials in a Rabbit Model", Ann Surg, 2012, vol. 255, No. 2, p. 311-318.

Van Der Gaag et al. "Preoperative Biliary Drainage for Cancer of the Head of the Pancreas", The New England Journal of Medicine, 2010, vol. 362, No. 2, p. 129-137.

Van Der Loos et al. "Accurate Quantitation of Ki67-positive Proliferating Hepatocytes in Rabbit Liver by a Multicolor Immunohistochemical (IHC) Approach Analyzed with Automated Tissue and Cell Segmentation Software", Journal of Histochemistry & Cytochemistry, 2013, vol. 61, No. 1, p. 11-18.

Van Gulik T. et al. "Controversies in the Use of Portal Vein Embolization", Digestive Surgery, 2008, vol. 25, p. 436-444.

Wagner M. et al. Role of Farnesoid X Receptor in Determining Hepatic ABC Transporter Expression and Liver Injury in Bile Duct-Ligated Mice, Gastroenterology, 2003, vol. 125, p. 825-838.

Wang X. et al. "The Forkhead Box m1b transcription factor is essential for hepatocyte DNA replication and mitosis during mouse liver regeneration", PNAS, 2002, vol. 99, No. 26, p. 16881-16886.

Weerachayaphorn J. et al. "Deleterious effect of oltipraz on extrahepatic cholestasis in bile duct-ligated mice", Journal of Hepatology, 2014, vol. 60, p. 160-166.

West G. et al. "The origin of allometric scaling laws in biology from genomes to ecosystems: towards a quantitative unifying theory of biological structure and organization", The Journal of Experimental Biology, 2005, vol. 208, p. 1575-1592.

Wong A. et al. "FRS2$\alpha$ attenuates FGF receptor signaling by Grb2-mediated recruitment of the ubiquitin ligase Cb1", PNAS, 2002, vol. 99, No. 16, p. 6684-6689.

Yamanaka N. et al. "Dynamics of Normal and Injured Human Liver Regeneration After Hepatectomy as Assessed on the Basis of Computed Tomography and Liver Function", Hepatology, 1993, vol. 18, No. 1, p. 79-85.

Yokoyama Y. et al. "The adverse effects of preoperative cholangitis on the outcome of portal vein embolization and subsequent major hepatectomies", Surgery, 2014, p. 1190-1196.

Zhang, et al. "Promotion of Liver Regeneration/Repair by Farnesoid X Receptor in Both Liver and Intestine in Mice", Hepatology, 2012, vol. 56, No. 6, p. 2336-2343.

Zhou M. et al. "Engineered Fibroblast Growth Factor 19 Reduces Liver Injury and Resolves Sclerosing Cholangitis in Mdr2-Deficient Mice", Hepatology, 2015, vol. 63, No. 3, p. 914-929.

Zollner G. et al. "Role of nuclear receptors and hepatocyte-enriched transcription factors for Ntcp repression in biliary obstruction in mouse liver", Am J Physiol Gastrointest Liver Physiol, 2005, vol. 289, p. G798-G805.

Zollner G. et al. "Coordinated induction of bile acid detoxification and alternative elimination in mice: role of FXR-regulated organic solute transporter-$\alpha/\beta$ in the adaptive response to bile acids", Am J Physiol Gastrointest Liver Physiol, 2006, vol. 290, No. 5, p. G923-932.

Ali, A. H. et al. "Recent advances in the development of farnesoid X receptor agonists", Annals of Translational Medicine, 2015, vol. 3, No. 1, 16 pages.

Carr R. M. et al. "FXR Agonists as Therapeutic Agents for Non-alcoholic Fatty Liver Disease", Current Atherosclerosis Reports, 2015, vol. 17, pp. 1-14.

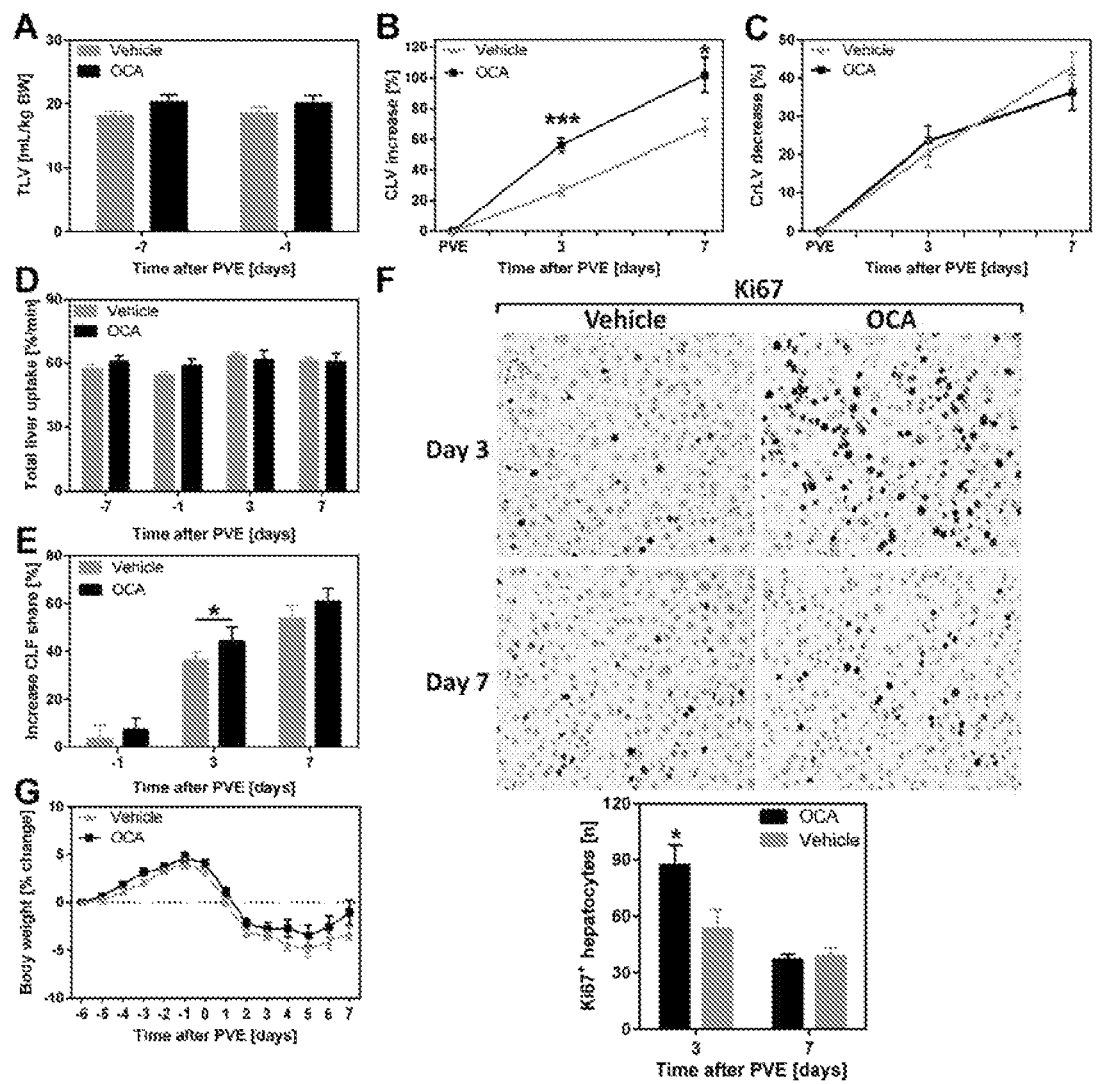
Figure 11A-G

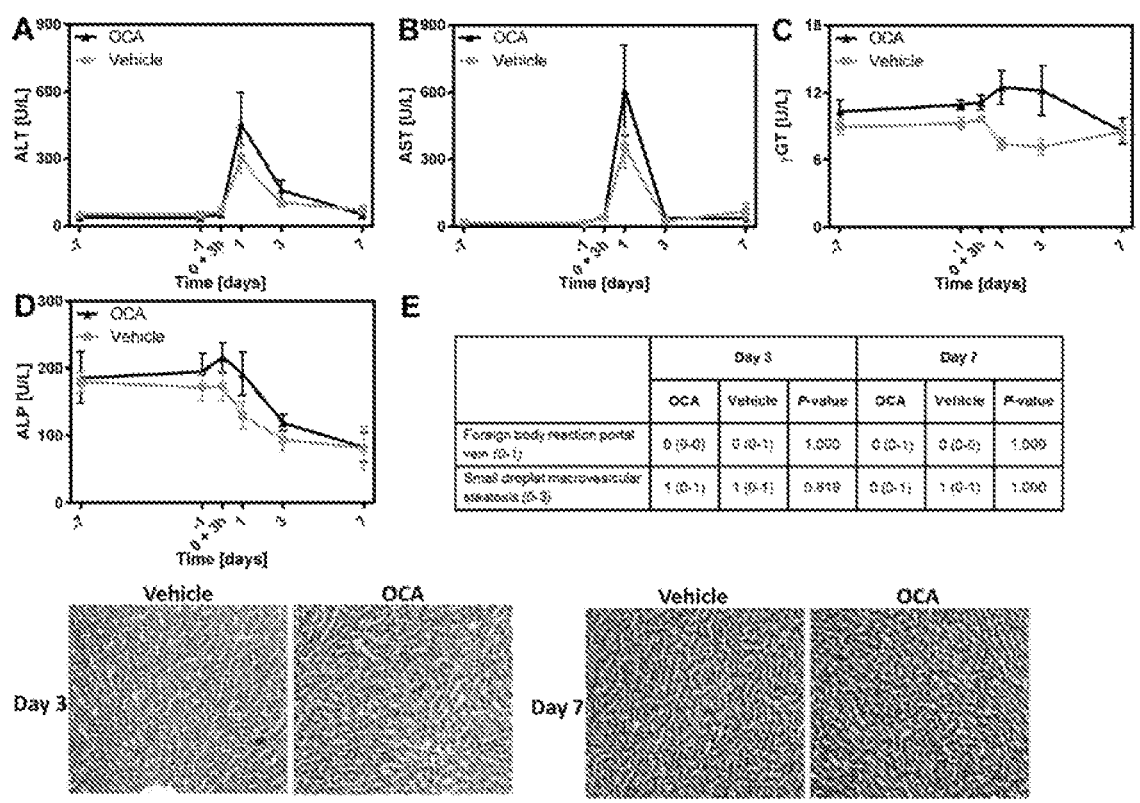
Figure 12A-E

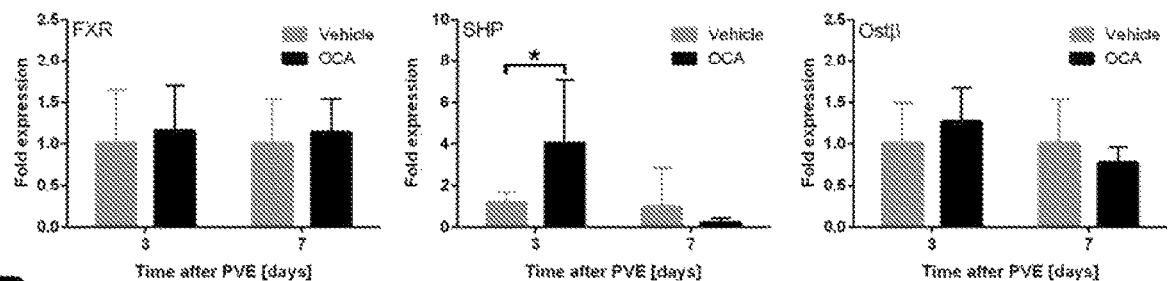
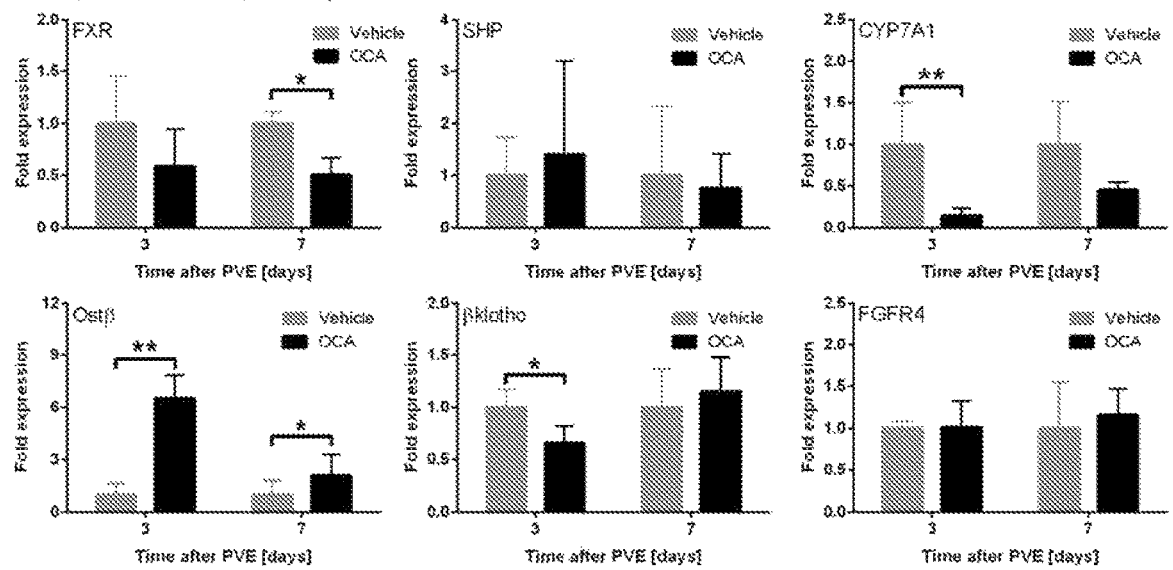
Figure 13A-B

METHODS OF PROMOTING HEPATIC REGENERATION

BACKGROUND

Liver failure occurs in a number of chronic and acute clinical conditions, including drug-induced hepatotoxicity, viral infections, vascular injury, autoimmune disease, and trauma. In addition, patients subject to genetic errors of metabolism may be at risk for developing liver failure. Symptoms of liver failure occurring as a result of these clinical conditions include, for example, acute hepatitis, chronic hepatitis, or cirrhosis.

Chronic liver disease is marked by the gradual destruction of liver tissue over time. Several liver diseases fall under this category, including cirrhosis and fibrosis, the latter of which is often the precursor of cirrhosis. Chronic hepatitis C virus infection and non-alcoholic steatohepatitis are two major causes of chronic liver disease. Once cirrhosis or fibrosis has occurred in the liver, it is generally considered irreversible. Conventional treatments currently focus on preventing any further progression of cirrhosis in the liver and mitigating the complications that can arise from cirrhosis. In more advanced stages of cirrhosis, the only known treatment is a liver transplant.

In acute liver disease, the liver is able to regenerate after being injured. If the disease progresses beyond the liver's capacity to regenerate new cells, the body's entire metabolism is severely affected. Loss of liver function may result in metabolic instability combined with disruption of essential bodily functions (i.e., energy supply, acid-base balance and thermoregulation). After large liver damage, liver tissue loses its regenerative and metabolic functions, and liver transplantation is a therapeutic strategy commonly used.

However, the clinical application of liver transplantation is limited by the availability of human hepatocytes, liver tissue and the number of liver cells that can be transplanted safely at one time.

A patient's ability to restore the pre-operative liver mass following major liver resection is well known. A variety of mediators are known to be hepatic mitogens, both in-vitro and in-vivo, but the precise mechanisms involved in liver regeneration remain to be defined (Michalopoulos, et al. Science, 1997, 276, 60-66). A significant problem with efforts to promote hepatic regeneration is that many therapeutic agents possess limited effectiveness in-vivo. The availability of pharmacological treatments to promote the regeneration of an adequate functional liver mass would therefore be a significant advance that could prevent many deaths from liver failure.

The ability to promote or increase hepatocyte proliferation in the clinical setting would have several important applications. It would allow previously unresectable hepatic malignancies to be resected by increasing the quantity of healthy hepatic tissue and preventing the patient's death from liver failure in the post-operative period due to inadequate remaining functional liver mass. Further, patients suffering from liver failure from toxic, metabolic, or viral causes may be spared death or a liver transplant if the native liver could be induced to regenerate at a rate that would restore adequate hepatic function prior to liver failure.

Despite ongoing research efforts, there remains a need for improved methods of promoting hepatic regeneration and repair. The development of therapeutic strategies that promote hepatocyte proliferation to treat liver damage caused by a range of hepatotoxic agents, diseases or pathological conditions is needed. The present invention addresses such needs.

BRIEF DESCRIPTION OF THE DRAWINGS

FIG. 11A is a bar graph showing TLV per kg body weight in the pretreatment phase.

FIG. 11B is a graph showing increase in CLV following PVE.

FIG. 11C is a graph showing decrease in CrLV following PVE.

FIG. 11D is a bar graph of total liver uptake of $^{99m}$Tc-mebrofenin determined by hepatobiliary scintigraphy.

FIG. 11E is a bar graph showing increase in the share of the caudal liver lobe to $^{99m}$Tc-mebrofenin uptake from baseline measurements at day −7.

FIG. 11F shows images of Ki67 stained liver sections at 100× magnification and quantification of Ki67-positive hepatocytes.

FIG. 11G is a graph showing percentage change in body weight relative to values at day −7.

FIG. 12A shows plasma ALT (alanine transaminase) levels before and after PVE.

FIG. 12B shows plasma AST (aspartate transaminase) levels before and after PVE.

FIG. 12C shows plasma γGT (gamma-glutamyl transferase) levels before and after PVE.

FIG. 12D shows plasma ALP (alkaline phosphatase) levels before and after PVE.

FIG. 12E shows quantitative scoring of H&E-stained sections of the caudal liver lobe.

FIG. 13A-B shows effect of obeticholic acid on ileal and hepatic gene expression.

FIG. 23 shows schematic overview of the study design.

SUMMARY OF THE INVENTION

Figure 1:
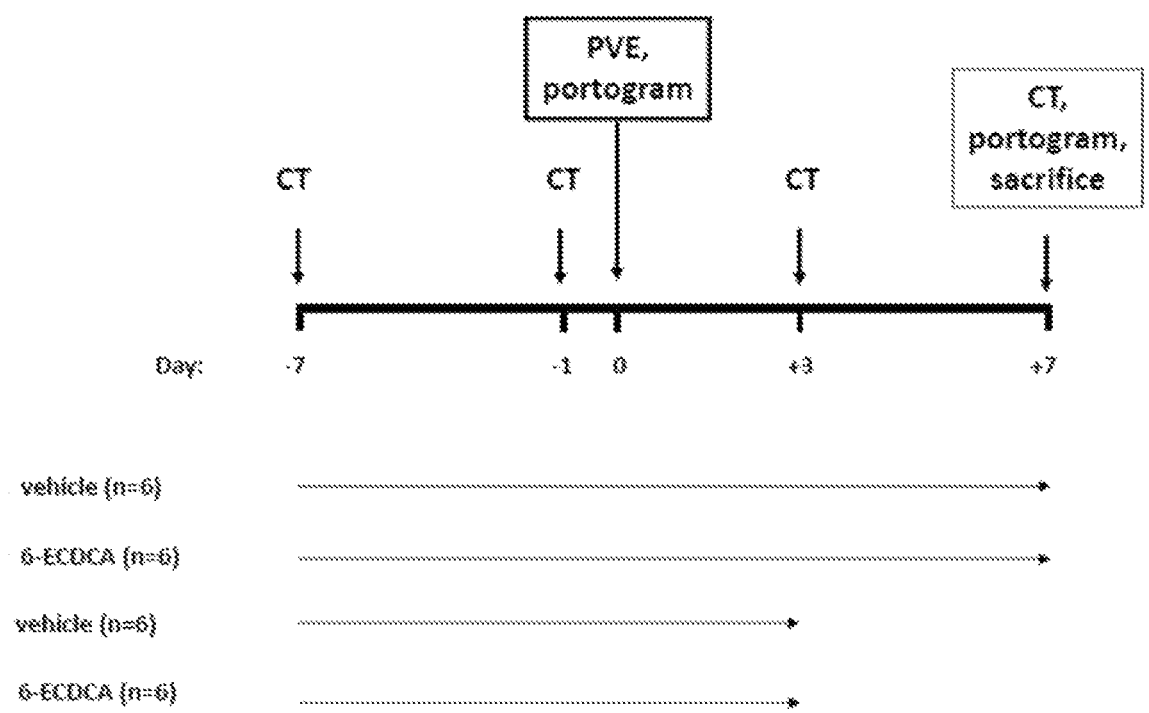
FIG. 1 is a chart depicting the study outline or an experimental approach and schedule for computed tomography (CT) and portography measurements, and portal vein embolization in rabbits (herein referred to as "PVE study rabbits").

An objective of the present invention is to provide methods of accelerating, promoting or increasing hepatic regeneration, and increasing liver mass. In one aspect, the present invention relates to a method of accelerating, promoting or increasing hepatic regeneration in a subject with reduced liver function, comprising administering to the subject a therapeutically effective amount of a compound of formula (A):

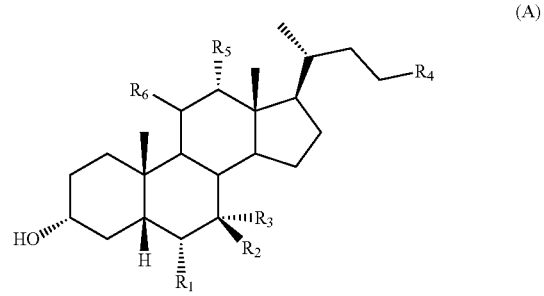

or a pharmaceutically acceptable salt thereof, wherein:

$R_1$ is hydrogen or $C_1$-$C_6$ alkyl;

$R_2$, $R_3$, $R_5$, and $R_6$ are each independently hydrogen or hydroxyl;

$R_4$ is $CO_2H$, $C(O)NH(CH_2)_mSO_3H$, $C(O)NH(CH_2)_nCO_2H$, or $OSO_3H$; and m and n are each independently 1, 2, or 3.

The present invention further relates to use of a compound of formula (A) or a pharmaceutically acceptable salt thereof, in the manufacture of a medicament for accelerating, promoting or increasing hepatic regeneration in a subject with reduced liver function, wherein $R_1$, $R_2$, $R_3$, $R_4$, $R_5$, $R_6$, m, and n are as defined herein.

The present invention also relates to a compound of formula (A) or a pharmaceutically acceptable salt thereof, for accelerating, promoting or increasing hepatic regeneration in a subject with reduced liver function, wherein $R_1$, $R_2$, $R_3$, $R_4$, $R_5$, $R_6$, m, and n are as defined herein.

In another aspect, the present invention relates to a method of increasing liver mass in a subject with reduced liver function, comprising administering to the subject a therapeutically effective amount of a compound of formula (A):

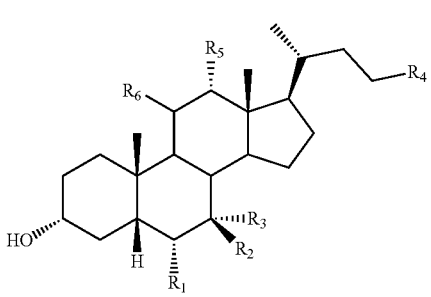

or a pharmaceutically acceptable salt thereof, wherein:
$R_1$ is hydrogen or $C_1$-$C_6$ alkyl;
$R_2$, $R_3$, $R_5$, and $R_6$ are each independently hydrogen or hydroxyl;
$R_4$ is $CO_2H$, $C(O)NH(CH_2)_mSO_3H$, $C(O)NH(CH_2)_nCO_2H$, or $OSO_3H$; and
m and n are each independently 1, 2, or 3.

The present invention further relates to use of a compound of formula (A) or a pharmaceutically acceptable salt thereof, in the manufacture of a medicament for increasing liver mass in a subject with reduced liver function, wherein $R_1$, $R_2$, $R_3$, $R_4$, $R_5$, $R_6$, m, and n are as defined herein.

The present invention also relates to a compound of formula (A) or a pharmaceutically acceptable salt thereof, for increasing liver mass in a subject with reduced liver function, wherein $R_1$, $R_2$, $R_3$, $R_4$, $R_5$, $R_6$, m, and n are as defined herein.

The invention further relates to a pharmaceutical composition comprising a compound of formula (A) or a pharmaceutically acceptable salt thereof, and a pharmaceutically acceptable carrier or excipient, for accelerating, promoting or increasing hepatic regeneration, or increasing liver mass in a subject with reduced liver function, wherein $R_1$, $R_2$, $R_3$, $R_4$, $R_5$, $R_6$, m, and n are as defined herein.

The invention further relates to a kit comprising a compound of formula (A) for use in methods of accelerating, promoting or increasing hepatic regeneration, or increasing liver mass in a subject with reduced liver function, wherein $R_1$, $R_2$, $R_3$, $R_4$, $R_5$, $R_6$, m, and n are as defined herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting.

Other features and advantages of the invention will be apparent from the following detailed description.

DETAILED DESCRIPTION

Definitions

Certain terms used in the specification and claims are collected here.

The term "liver disease" as used herein refers to a hepatic disorder. Generally, a liver disease may be caused by any condition that results in the disturbance of the morphological and/or functional integrity of a body's liver. The etiology and treatment of liver diseases are described, e.g., in Oxford Textbook of Medicine (Warrell, Oxford Textbook of Medicine, David A. Warrell, Timothy M. Cox, John D. Firth, Oxford University Press, USA; Fifth edition (Jul. 22, 2010)).

As used herein, the term "chronic liver disease" refers to a disease process of the liver that involves progressive destruction and regeneration of the liver parenchyma leading to fibrosis and cirrhosis. Chronic liver disease causes can be any condition that results in the gradual degradation and renewal of the tissue cells with a body's liver. This process usually results in fibrosis or cirrhosis and can be potentially fatal in cases of chronic liver failure. The classification of the sources of chronic liver diseases fall into five groupings: (i) viral causes such as hepatitis B and C or cytomegalovirus or Epstein Barr virus, (ii) metabolic causes such as Haemochromatosis, non-alcoholic fatty liver disease or Wilson's disease, (iii) autoimmune response causes such as autoimmune chronic hepatitis, primary biliary cirrhosis or primary sclerosing cholangitis, (iv) toxin-related causes such as alcoholic liver disease or nitrofurantoin, amiodarone, or methotrexate, and (v) other miscellaneous causes such as right heart failure. The main cause of chronic liver disease is overuse of alcohol, leading to cirrhosis and hepatitis. Therefore, the highest risk group is people who are prone to alcohol abuse. The symptoms associated with chronic liver disease depend on the level of degeneration within the liver.

The term "acute liver disease", as used herein, refers to the appearance of severe complications rapidly after the first signs of liver disease, such as jaundice, and indicates that the liver has sustained damage. The complications are, e.g., hepatic encephalopathy and impaired protein synthesis, as measured, for instance, by the levels of serum albumin and the prothrombin time in the blood. The 1993 classification defines hyperacute as within 1 week, acute as 8-28 days and subacute as 4-12 weeks (Williams, et al. Lancet, 1993, 342, 273). This reflects the fact that the pace of disease evolution strongly influences prognosis. Underlying etiology is another significant determinant of outcome (Grady, et al. Postgrad Med J, 2005, 81, 148). "Acute liver failure" occurs when the liver rapidly loses its ability to function. Acute liver failure is a complex multi-systemic illness that evolves quickly after a catastrophic insult to the liver leading to the development of encephalopathy. Whereas, more commonly, liver failure develops slowly over the course of years, in acute liver failure, liver failure develops in a matter of days.

As used herein "transplanted liver" refers a liver transplanted into a subject and also includes the so-called "partial liver transplant" which corresponds to a graft consisting of the part of the liver of a donor. Liver transplantation also refers to injection of hepatocytes (genetically modified or stimulated to proliferate or differentiate) into the portal vein. Portal vein embolization (PVE) can be used to increase future remnant liver volume in patients scheduled for major liver resection.

As used in the context of liver transplantation, the term "liver regeneration" refers to morphologic changes in which lost liver tissues are replaced by hepatocyte growth of a liver transplant or partial liver transplant, but also includes biochemical changes such as improvement, recovery, or normalization of hepatic functions. Specific subjects to be treated by the composition of the invention includes, for example, patients who received partial liver transplant after the liver had been wholly resected for treating hepatic failure caused by liver diseases such as hepatitis, hepatic cirrhosis of alcoholic, viral, drug or unknown cause, or hepatic cancer.

The phrases "accelerating hepatic regeneration", "promoting hepatic regeneration" and "increasing hepatic regeneration", as used herein, are demonstrated by a shorter period needed to reach the final liver mass or increased final liver mass (for example, as determined by computed tomography), or both, to an increase in the final mass and the rate of reaching that mass, as compared to an untreated control.

A "therapeutically effective amount" of a compound of formula (A) is an amount (quantity or concentration) of compound or compounds. The amount of the compound to be administered to a subject depends on the particular stage of liver damage, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, "subject" refers to a human or animal (in the case of an animal, more typically a mammal). In one aspect, the subject is a human.

The term "$C_1$-$C_6$ alkyl", as used herein, refers to a straight-chain or branched hydrocarbon moiety having 1, 2, 3, 4, 5, or 6 carbon atoms. "$C_1$-$C_4$ alkyl" refers to a straight-chain or branched hydrocarbon moiety having 1, 2, 3, or 4 carbon atoms. Examples of $C_1$-$C_6$ alkyl moieties include, but are not limited to, methyl, ethyl, n-propyl, isopropyl, n-butyl, isobutyl, sec-butyl, and t-butyl.

As used herein, the term "metabolite" refers to glucuronidated and sulphated derivatives of the compounds of formula (A), wherein one or more glucuronic acid or sulphate moieties are linked to the compound of the invention. Glucuronic acid moieties may be linked to the compounds through glycosidic bonds with the hydroxyl groups of the compounds (e.g., 3-hydroxyl, 7-hydroxyl, 11-hydroxyl, and/or 12-hydroxyl). Sulphated derivatives of the compounds may be formed through sulfation of the hydroxyl groups (e.g., 3-hydroxyl, 7-hydroxyl, 11-hydroxyl, and/or 12-hydroxyl). Examples of metabolites include, but are not limited to, 3-O-glucuronide, 7-O-glucuronide, 11-O-glucuronide, 12-O-glucuronide, 3-O-7-O-diglucuronide, 3-O-11-O-diglucuronide, 3-O-12-O-diglucuronide, 7-O-12-O-diglucuronide, and 3-O-7-O-12-O-triglucuronide, of the compounds described herein, and 3-sulphate, 7-sulphate, 11-sulphate, 12-sulphate, 3,7-bisulphate, 3,11-bisulphate, 3,12-bisulphate, 7,12-bisulphate, 3,7,11-tri sulphate, and 3,7,12-trisulphate, of the compounds described herein.

As used herein, "pharmaceutically acceptable salts" refer to derivatives of a compound of the invention wherein the parent compound is modified by forming acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier is "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, a "pharmaceutical composition" refers to a formulation containing a compound of formula (A) or a pharmaceutically acceptable salt thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it may be necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

"Combination therapy" (or "co-therapy") refers to the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Methods of the Invention

The present invention provides methods of accelerating, promoting or increasing hepatic regeneration, or increasing liver mass in a subject with reduced liver function, comprising administering to the subject a therapeutically effective amount of a compound of formula (A):

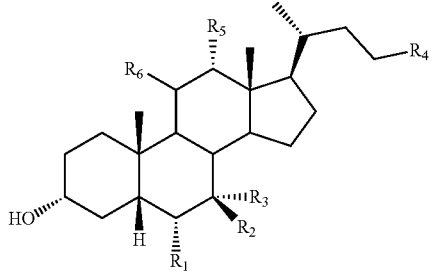

or a pharmaceutically acceptable salt thereof, wherein:
$R_1$ is hydrogen or $C_1$-$C_6$ alkyl;
$R_2$, $R_3$, $R_5$, and $R_6$ are each independently hydrogen or hydroxyl;

$R_4$ is $CO_2H$, $C(O)NH(CH_2)_mSO_3H$, $C(O)NH(CH_2)_nCO_2H$, or $OSO_3H$; and
m and n are each independently 1, 2, or 3.

In one embodiment, the method relates to promoting or increasing hepatic regeneration. In another embodiment, the method relates to promoting hepatic regeneration. In yet another embodiment, the method relates to increasing hepatic regeneration. In one embodiment, the method relates to accelerating hepatic regeneration. In another embodiment, the method relates to increasing liver mass.

In one embodiment, the compound used in the invention is a compound of formula (A), wherein $R_1$ is hydrogen. In one embodiment, the compound used in the invention is a compound of formula (A), wherein $R_1$ is unsubstituted $C_1$-$C_6$ alkyl. In a further embodiment, the compound used in the invention is a compound of formula (A), wherein $R_1$ is unsubstituted $C_1$-$C_3$ alkyl. In a further embodiment, the compound used in the invention is a compound of formula (A), wherein $R_1$ is selected from methyl, ethyl, and propyl. In a further embodiment, the compound used in the invention is a compound of formula (A), wherein $R_1$ is ethyl.

In one embodiment, the compound used in the invention is a compound of formula (A), wherein $R_2$ is hydrogen. In one embodiment, the compound used in the invention is a compound of formula (A), wherein $R_1$ is hydroxyl.

In one embodiment, the compound used in the invention is a compound of formula (A), wherein $R_3$ is hydrogen. In one embodiment, the compound used in the invention is a compound of formula (A), wherein $R_3$ is hydroxyl.

In one embodiment, the compound used in the invention is a compound of formula (A), wherein $R_4$ is $CO_2H$. In one embodiment, the compound used in the invention is a compound of formula (A), wherein $R_4$ is $C(O)NH(CH_2)_mSO_3H$. In one embodiment, the compound used in the invention is a compound of formula (A), wherein $R_4$ is $C(O)NH(CH_2)_nCO_2H$. In one embodiment, the compound used in the invention is a compound of formula (A), wherein $R_4$ is $OSO_3H$. In one embodiment, the compound used in the invention is a compound of formula (A), wherein $R_4$ is $CO_2H$ or $OSO_3H$.

In one embodiment, the compound used in the invention is a compound of formula (A), wherein $R_5$ is hydrogen. In one embodiment, the compound used in the invention is a compound of formula (A), wherein $R_5$ is hydroxyl.

In one embodiment, the compound used in the invention is a compound of formula (A), wherein $R_6$ is hydrogen. In one embodiment, the compound used in the invention is a compound of formula (A), wherein $R_6$ is hydroxyl. In one embodiment, the compound used in the invention is a compound of formula (A), wherein $R_6$ is α-hydroxyl. In one embodiment, the compound used in the invention is a compound of formula (A), wherein $R_6$ is β-hydroxyl.

In one embodiment, the compound used in the invention is a compound of formula (A), wherein $R_1$ is methyl, ethyl or propyl, and $R_5$ is hydrogen. In one embodiment, the compound used in the invention is a compound of formula (A), wherein $R_1$ is methyl, ethyl or propyl, and $R_6$ is hydrogen. In one embodiment, the compound used in the invention is a compound of formula (A), wherein $R_1$ is methyl, ethyl or propyl, and $R_5$ and $R_6$ are each hydrogen.

In one embodiment, the compound used in the invention is a compound of formula (A), wherein $R_2$ is hydrogen, and $R_3$ is hydroxyl.

In one embodiment, the compound used in the invention is a compound of formula (A), wherein m is 1. In one embodiment, the compound used in the invention is a compound of formula (A), wherein m is 2. In one embodiment, the compound used in the invention is a compound of formula (A), wherein m is 3.

In one embodiment, the compound used in the invention is a compound of formula (A), wherein n is 1. In one embodiment, the compound used in the invention is a compound of formula (A), wherein n is 2. In one embodiment, the compound used in the invention is a compound of formula (A), wherein n is 3.

In one embodiment, the compound used in the invention is a compound of formula (A), wherein the compound is

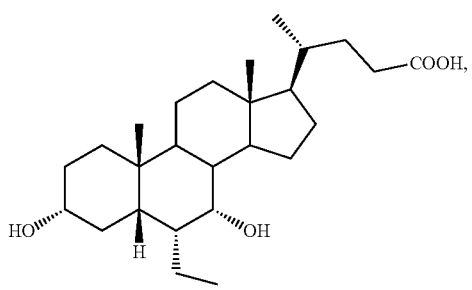

(1)

or a pharmaceutically acceptable salt thereof.

In one embodiment, the compound used in the invention is a compound of formula (A), wherein the compound is

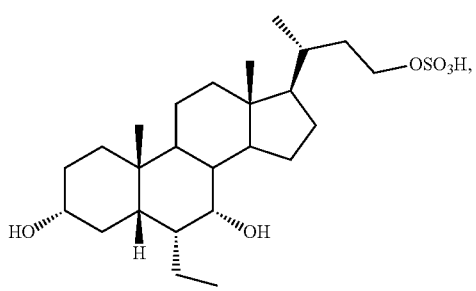

(2)

or a pharmaceutically acceptable salt thereof.

In one embodiment, the compound used in the invention is a compound of formula (A), wherein the compound is a pharmaceutically acceptable salt.

In one embodiment, the compound used in the invention is a compound of formula (A), wherein the salt is a sodium or triethylammonium salt.

In one embodiment, the compound used in the invention is

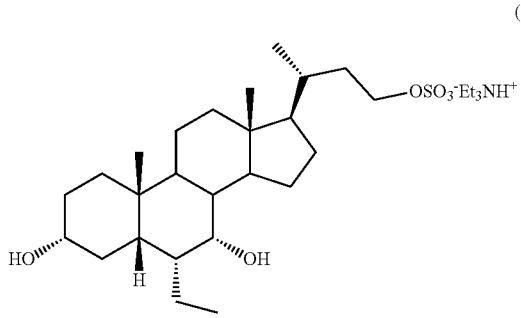

(3)

In another embodiment, the compound used in the invention is

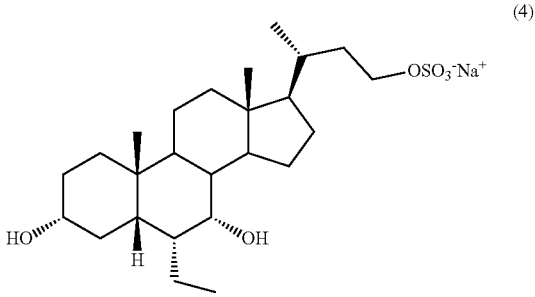

(4)

In yet another embodiment, the compounds of formula (A) are FXR agonists.

Liver regeneration is severely impaired in patients with parenchymal pathology caused by, e.g., chemotherapy, steatosis, or cholestasis [DeMeijer 2010; Farges 2013; Hubert 2015].

The risks of performing major liver resection in patients with obstructive cholestasis in particular were recognized decades ago [Dixon 1983] and have shaped the current surgical management of jaundiced patients with a biliary malignancy. The poor regenerative capacity of cholestatic livers has spurred the introduction of invasive procedures such as preoperative biliary drainage (van der Gaag, et al. *N Engl J Med* 2010, 362(2):129-37), portal vein embolization (PVE) [VanGulik 2008], and ALPPS (Oldhafer, et al. *Ann Surg.* 2016, 263(5):839-41) to relieve cholestasis, or increase liver size prior to resection.

In certain embodiments, the compound of formula (A) is for use in regenerating damaged liver, increasing the mass of a damaged liver or improving function of the damaged liver, or a combination thereof.

The enhanced liver regeneration and/or increase in liver mass and/or improvement in function may be desired where a liver or liver section is implanted to a subject to replace the subject's damaged or malfunctioning liver. In one embodiment, the subject has a transplanted liver. In one embodiment, the subject has a resected liver. In one embodiment, the reduced liver function is the result of surgical operation, disease, pathological condition, or injury. In another embodiment, the reduced liver function is the result of surgical operation. In one embodiment, the surgical operation is hepatic arterial embolization or portal venous manipulations. In one embodiment, the surgical operation is transarterial chemoembolization (TACE). In one embodiment, the surgical operation is partial hepatectomy. In one embodiment, the compound is administered prior to or after the surgical operation, or in combination.

In order to promote hepatic regeneration or increase mass of a transplanted liver or liver section, the compound of formula (A) may be applied directly on the liver to be implanted while it is still ex-vivo, immediately during the operation to the liver recipient and/or several days post operation. Where liver regeneration is required due to planned removal of a part of the liver by surgery (for example due to tumor in the liver), or due to hepatitis, the period of administration can be divided to pre-operation and post-operation administration period. For example, where the administration is for 4-5 days it is possible to administer the compound of formula (A) for 1-2 days prior to the operation and 3-4 additional days after the operation.

The conditions that require liver regeneration include a situation where a part of the liver is removed due to surgery, where liver is damaged due to trauma, or where the liver is damaged due to a disease process (without being removed, e.g. hepatitis) that caused significant degree of acute liver dysfunction.

In one embodiment, the disease or condition that may be the cause for damage of the liver is selected from acute liver damage induced by exposure to alcohol, e.g. steatosis, alcoholic hepatitis or cirrhosis; acute viral hepatitis, such as hepatitis type A; a metabolic disease resulting in abnormal storage of copper, such as Wilson's disease, or iron (hemochromatosis); acute liver damage caused by exposure to drugs or toxins, acute hepatitis caused by autoimmune processes, such as autoimmune hepatitis, or acute liver damage caused by obesity or other causes of acute steatohepatitis.

In a separate embodiment, the disease or condition that may be the cause for damage of the liver is selected from chronic liver damage induced by hepatitis B or C virus infections or by alcohol. Chronic hepatitis B, cirrhosis, but also nonalcoholic fatty liver disease (NAFLD) are included. NAFLD is a term chosen to describe a clinical and pathological syndrome that spans a spectrum from simple steatosis to non-alcoholic steatohepatitis (NASH).

In one embodiment, the reduced liver function is the result of a disease or pathological condition selected from cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, liver transplant associated graft versus host disease, congenital hepatic fibrosis, choledocholithiasis, granulomatous liver disease, Sjogren's syndrome, sarcoidosis, Wilson's disease, Gaucher's disease, hemochromatosis, and alpha 1-antitrypsin deficiency.

The liver regeneration should be functional resulting in an improvement of liver functions evident by higher levels in the serum of proteins that are produced by the liver, such as various coagulation factors, as compared to untreated control. In particular, liver function or integrity may be assessed by measuring any of a number of parameters as is well known in the art; for example, prolonged serum prothrombin time (blood coagulation) is a sign of damaged liver; albumin levels are decreased in chronic liver disease; alkaline phosphatase levels in plasma rise with large bile duct obstruction, intrahepatic cholestasis or infiltrative diseases of the liver; increased total bilirubin may be a sign of problems in the liver; gamma glutamyl transpeptidase (GGT) may be elevated with even minor, subclinical levels of liver dysfunction; 5' nucleotidase levels reflect cholestasis or damage to the intra or extrahepatic biliary system; or liver glucose production is reduced in a damaged liver.

Pharmaceutical Compositions

A "pharmaceutical composition" is a formulation containing one or more compounds of formula (A) in a form suitable for administration to a subject. In one embodiment, the pharmaceutical composition is in bulk or in unit dosage form. It can be advantageous to formulate compositions in dosage unit form for ease of administration and uniformity of dosage. The specification for the dosage unit forms are dictated by and directly dependent on the unique characteristics of the active reagent and the particular therapeutic effect to be achieved.

Possible formulations include those suitable for oral, sublingual, buccal, parenteral (e.g., subcutaneous, intramuscular, or intravenous), rectal, topical including transdermal, intranasal and inhalation administration. Most suitable means of administration for a particular patient will depend on the nature and severity of the disease being treated or the nature of the therapy being used and on the nature of the active compound, but where possible, oral administration may be used for the prevention and treatment of FXR mediated diseases and conditions. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastilles comprising the active compound in an inert base, such as gelatin and glycerin or sucrose acacia.

Formulations suitable for parenteral administration typically comprise sterile aqueous solutions containing a predetermined concentration of the active compound; the solution may be isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions may be administered intravenously, they may also be administered by subcutaneous or intramuscular injection.

Formulations suitable for rectal administration may be provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent. Suitable formulations for administration by inhalation include fine particle dusts or mists which may be generated by means of various types of metered dose pressurized aerosols, nebulizers, or insufflators.

For pulmonary administration via the mouth, the particle size of the powder or droplets is typically in the range 0.5-10 μm or 1-5 μm, to ensure delivery into the bronchial tree. For nasal administration, a particle size in the range 10-500 μm may be used to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 μm, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents.

Nebulizers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulizers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation.

In a further embodiment, the present invention provides a pharmaceutical composition comprising, as active ingredient, a compound of the invention together, and/or in admixture, with at least one pharmaceutical carrier or diluent. These pharmaceutical compositions may be used to increase hepatic regeneration.

The carrier is pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

EXAMPLES

Example 1. Synthesis of a Compound of Formula (A)

Compounds of formula (A) may be readily prepared by those skilled in the art. In particular, compounds of the invention may be prepared according to the published procedures in U.S. Pat. Nos. 7,786,102, 7,994,352, and 7,932,244.

Example 2. Synthesis of Compound 1

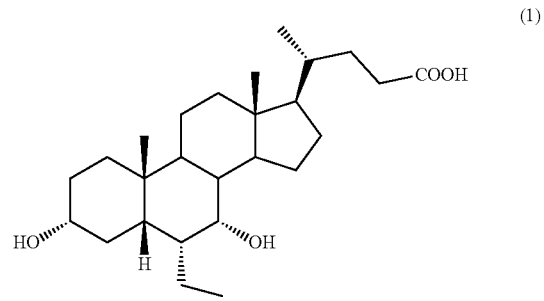

Preparation of methyl 3α-hydroxy-7-keto-5β-cholanate.

17.0 kg of 3α-hydroxy-7-keto-5β-cholanic acid, 68 kg of methanol and 0.17 kg of methansulphonic acid were charged into a reactor. The reaction mixture was then heated to 30-60° C. for 1 hour and 25.5 kg of demineralised water was added. The mixture obtained was then stirred, cooled to 20-25° C. until a good precipitation was obtained, then cooled further to 0-15° C. The precipitate was filtered and washed with a mixture of water and methanol and further dried in an oven at about 40° C. 15 kg of methyl 3α-hydroxy-7-keto-5β-cholanate was thus obtained. The stoichiometric yield was 85.2%.

Preparation of methyl 3α-trimethyl siloxy-7-keto-5β-cholanate.

15.0 kg of methyl 3α-hydroxy-7-keto-5β-cholanate, 45 kg of toluene, 7.5 kg of triethylamine, and 7.5 kg of trimethylchlorosilane were charged into a reactor. The mixture was heated to 70-80° C. and was kept under stirring at that temperature for about 1 hour, then 37.5 kg of water was added and the mixture was stirred at 15-20° C. The lower aqueous phase was then separated and eliminated. The organic phase was concentrated until an oily residue was obtained, to which 15 kg of tetrahydrofuran was added. The solution thus obtained containing methyl 3α-trimethylsiloxy-7-keto-5β-cholanate was used in the following step.

Preparation of methyl 3α,7α-di-trimethylsililoxy-5β-cholanate.

30 kg of tetrahydrofuran was loaded in a reaction vessel, then the mixture was brought to a temperature between −90° and −60° C. 9.8 kg of 100% lithium diisopropylamide and 9.3 kg of trimethylchlorosilane were added, and the whole solution of tetrahydrofuran prepared in (b) and containing methyl 3α-trimethylsiloxy-7-keto-5β-cholanate was poured. The mixture was then stirred for about 1 hour at a temperature between −60 and −90° C. for 1 hour. A solution of 4.50 kg of sodium bicarbonate and 60 kg of water was then poured and the mixture was stirred at 0-10° C., and the lower aqueous phase was separated and eliminated. The lower phase was then concentrated until an oily residue was obtained, to which 45.0 kg of methylene chloride was added. The solution of methyl 3α,7α-di-trimethylsililoxy-5β-cholanate thus obtained was sent to the next stage.

Preparation of methyl 3α-hydroxy-6-ethylidene-7-keto-5β-cholanate. The entire solution of methyl 3α,7α-di-trimethylsililoxy-5β-cholanate in methylene chloride coming from the preceding step was charged into a reactor and cooled to between −90 and −60° C. 1.97 kg of acetaldehyde and 5.5 kg of boron trifluoride etherate were then added. The reaction mixture was kept under stirring at the above temperature for 2-4 hours, after which it was heated to 30-35°

C. and kept at that temperature for about 2-4 hours. Then 60 kg of water was added. The mixture obtained was stirred and the aqueous phase was separated. The solution thus obtained containing methyl 3α-hydroxy-6-ethylidene-7-keto-5β-cholanate was used in the next step.

Preparation of 3α-hydroxy-6-ethylidene-7-keto-5β-cholanic acid.

The solution of methyl 3α-hydroxy-6-ethylidene-7-keto-5β-cholanate in methylene chloride obtained in the previous step was charged into a reactor. The solvent was then removed by distillation until an oily residue was obtained, to which 15 kg of methanol was added. The reaction mixture was then heated to 45-50° C. and 7.5 kg of 30% sodium hydroxide was added, and the reaction mixture was kept at the above temperature for about 1 hour. Then 30 kg of water was added, followed by 45.0 kg of methylene chloride and 7.5 kg of 85% phosphoric acid. The lower organic phase was separated and the aqueous phase was eliminated subsequently. The solvent was removed from the organic phase by distillation until a pasty residue was obtained. About 37.5 kg of ethyl acetate was added to the residue and the mixture was heated to 65-75° C., then cooled to 10-35° C. The precipitate was obtained, filtered and washed with ethyl acetate, and was dried. 8.0 kg of 3α-hydroxy-6-ethyliden-7-keto-5β-cholanic acid was obtained, with a stoichiometric yield of 51.8% calculated on methyl 3α-hydroxy-7-keto-5β-cholanate.

Preparation of 3α-hydroxy-6β-ethyl-7-keto-5β-cholanic acid.

8.0 kg of 3α-hydroxy-6-ethylidene-7-keto-5β-cholanic acid, 48.0 kg of water, 5.1 kg of 30% sodium hydroxide, 0.80 kg of 5% palladium/carbon were charged into a reactor. The reaction mixture was hydrogenated at a pressure between 1 and 3 atmospheres, until the hydrogen absorption was no longer noted.

Preparation of 3α-hydroxy-6α-ethyl-7-keto-5β-cholanic acid.

At the end of the reaction directly above, the mixture was heated to 95-105° C. and was kept at that temperature for a few hours to allow the 3α-hydroxy-6β-ethyl-7-keto-5β-cholanic acid to convert into the corresponding epimer of the desired 3α-hydroxy-6α-ethyl-7-keto-5β-cholanic acid. The suspension was filtered, and the catalyst was recovered. 5.1 kg of 85% phosphoric acid 9.6 kg of ethyl acetate were added to the filtered solution and the reaction mixture was heated to a temperature between 40 and 70° C. It was cooled to a temperature between 0 and 30° C. and the precipitate was recovered by filtration. After washing with ethyl acetate, the precipitate was dried in an oven at 65° C. 5.0 kg of 3α-hydroxy-6α-ethyl-7-keto-5β-cholanic acid was obtained. Stoichiometric yield: 62.2%. m.p. 185-188° C.

Preparation of 3α,7α-dihydroxy-6α-ethyl-5β-cholanic acid (Compound 1).

5.0 kg of 3α-hydroxy-6α-ethyl-7-keto-5β-cholanic acid, 5.0 kg of water, 2.50 kg of sodium hydroxide were loaded in a reactor. The mixture was then heated to 70-105° C. and a mixture of sodium borohydride dissolved in 2.50 kg of water was poured, the mixture was then kept warm for 1 hour, cooled to room temperature, and 10.0 kg of demineralised water, 15.0 kg of methylene chloride and 3.00 kg of 85% phosphoric acid were added. The mixture was stirred, the lower organic phase was separated and the aqueous phase was removed. Crystallization of the crude product was obtained by cooling the organic solution. This product was dissolved in 50 kg of demineralised water and 1.10 kg of 30% ammonia. The mixture was then stirred until a complete solution was obtained. The mixture was kept at 20-50° C., and 1.50 kg of phosphoric acid was poured. The precipitated mixture was stirred at a temperature between 20 and 50° C., then the precipitate was recovered by filtration, washed with water and dried. 4.50 kg of 3α,7α-di-hydroxy-6α-ethyl-5β-cholanic acid (Compound 1). Stoichiometric yield: 89.6%.

Example 3. Syntheses of Compounds 2, 3 and 4

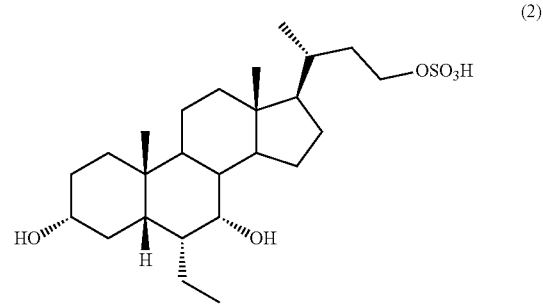

(2)

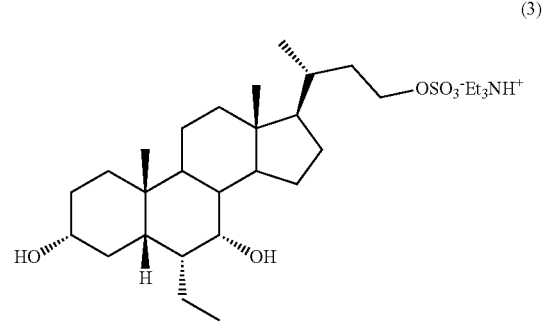

(3)

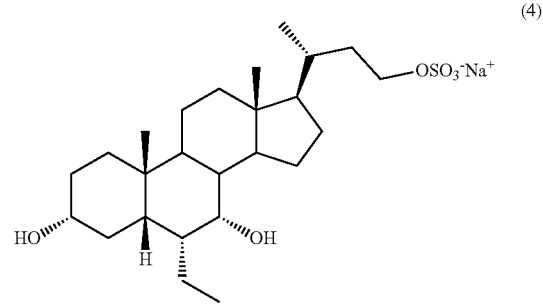

(4)

Preparation of 3α-tetrahydropyranyloxy-7-keto-5β-cholan-24-oic Acid (2A).

3,4-dihydro-2H-pyrane (1.74 ml, 19 mmol) in dioxane (12 ml) was dropped slowly to a solution of p-toluenesulfonic acid (115 mg, 0.6 ml) and 6α-ethyl-7-ketolithocholic acid (5.0 g, 12 mmol) in dioxane (55 ml). The reaction mixture was stirred at room temperature for 2 hours. Water (40 ml) was then added, and the mixture was partially concentrated under vacuum and extracted with EtOAc (4 times/25 ml). The combined organic fractions were washed with brine (1 times/50 ml), dried over anhydrous Na2SO4 and evaporated under vacuum to afford 6 g of compound 2A. The crude derivative was used for the next step without further purification.

Preparation of 3α-tetrahydropyranyloxy-6α-ethyl-7-keto-24-nor-5β-cholan-23-iodide (3A).

Under irradiation with a 300 W tungsten lamp, iodine (5 g, 20 mmol) in $CCl_4$ (75 ml) was added dropwise to a solution of 2A (5.5 g, 11 mmol) and lead tetra-acetate (4.9 g, 11 mmol) in CCl$_4$ (200 ml). The reaction mixture was stirred until the color was permanent (18 h). The mixture was cooled and filtered on Celite®. The organic phase was washed with a 5% Na$_2$S$_2$O$_3$ solution, 5% NaOH, brine (15 ml), dried over anhydrous Na$_2$SO$_4$ and evaporated under vacuum. The residue was purified by silica gel flash chromatography using a mixture of light petroleum/EtOAc 95/5 as mobile phase to give 4.6 g of compound 3A (40% yield).

Preparation of 3α-hydroxy-6α-ethyl-7-keto-24-nor-5β-cholan-23-iodide (4A).

Compound 3A (2.2 g, 3.8 mmol) was stirred in a solution of HCl 37% in THF (50 ml) overnight at room temperature. The reaction mixture was washed with a saturated solution of NaHCO$_3$ (20 ml), H$_2$O (20 ml), and brine (20 ml), dried over Na$_2$SO$_4$, and evaporated under vacuum to afford 1.4 g of compound 4A (80% yield). The crude derivative was used for the next step without further purification.

Preparation of 3α-tert-Buthyldimethylsilyloxy-6α-ethyl-7-keto-24-nor-5β-cholan-23-iodide (5A).

To a solution of 4A (1.4 g, 2.8 mmol) in CH$_2$Cl$_2$ (30 ml), tert-butyldimethylsilylchloride (496 mg, 3.22 mmol) and imidazole (230 mg, 3.36 mmol) were added and the mixture was stirred overnight at room temperature. The reaction mixture was washed with a saturated solution of NaHCO$_3$ (30 ml), brine (30 ml), and dried over anhydrous Na$_2$SO$_4$. The organic phase was evaporated under vacuum to afford 1.5 g of compound 5A (87% yield). The crude derivative was used for the next step without further purification.

Preparation of 3α-tert-butyldimethylsilyloxy-6α-ethyl-7-keto-24-nor-5β-cholan-23-ole (6A).

To a solution of 5A (1.2 g, 1.96 mmol) in acetone (12 ml), Ag$_2$CO$_3$ (1.1 g, 3.9 mmol) was added. The reaction mixture was refluxed overnight and then cooled to r.t., filtered on Celite® washed with acetone and the combined organic phases were concentrated to yield 1 g of compound 6A. The crude derivative was used for the next step without further purification.

Preparation of 3α-tert-Buthyldimethylsilyloxy-7α-hydroxy-6α-ethyl-24-nor-5β-cholan-23-ole (7A).

To a solution of 6A (1 g, 1.96 mmol) in a mixture of THF (50 ml) and H$_2$O (12.5 ml), NaBH$_4$ (740 mg, 19.6 mmol) was added and the mixture was stirred at room temperature for 1 hours and 30 minutes. The reaction solution was partially concentrated under vacuum and extracted with CHCl$_3$ (3 times/20 ml). The combined organic layers were washed with brine (1 time/50 ml), dried over anhydrous Na$_2$SO$_4$, and evaporated under vacuum. The crude residue was purified by silica gel flash chromatography using a mixture of CH$_2$Cl$_2$:MeOH 99:1 as mobile phase to give 0.8 g of 7A (81% yield).

Preparation of 3α-tert-butyldimethylsilyloxy-7α-hydroxy-6α-ethyl-24-nor-5β-cholan-23-sulphate triethyl ammonium salt (Compound 2).

To a solution of 7A (0.5 g, 0.99 mmol) in THF (7 ml) cooled at −3° C., Et$_3$N (0.3 ml, 2.1 mmol) was added and the resulting mixture was stirred for 10 min. ClSO$_3$H (0.1 ml, 1.5 mmol) was added and the mixture was stirred overnight at room temperature. Water (10 ml) was then added and the mixture was extracted with CH$_2$Cl$_2$ (3 times/15 ml), dried over anhydrous Na$_2$SO$_4$, and evaporated under vacuum. The crude sulphate derivative was used for the next step without further purification.

Preparation of 3α,7α,23-trihydroxy-6α-ethyl-24-nor-5β-cholan-23-sulphate triethyl ammonium salt (Compound 3).

To a solution of Compound 2 (0.5 g, 0.77 mmol) in acetone (8 ml), PdCl$_2$(CH$_3$CN)$_2$ (10 mg, 0.05 eq) was added and the mixture was stirred at room temperature for 3 hours. The reaction mixture was filtered, concentrated under vacuum and purified by medium pressure Lichroprep RP-8 using a MeOH/H$_2$O 8/2 mixture as mobile phase to afford 0.115 g of Compound 3 (mp 118-121° C.).

Preparation of 3α,7α,23-trihydroxy-6α-ethyl-24-nor-5β-cholan-23-sulphate sodium salt (Compound 4).

To a solution of Compound 2 (0.4 g, 0.72 mmol) in a mixture of acetone (4 ml) and H$_2$O (0.08 ml), PdCl$_2$(CH$_3$CN)$_2$ (10 mg, 0.05 eq) was added and the resulting mixture was stirred at room temperature for 3 hours. The reaction mixture was filtered over Celite® and concentrated under vacuum. The resulting residue was treated with a methanolic solution of 10% NaOH for 2 h. The resulting mixture was concentrated under vacuum and submitted to liquid medium pressure purification using a mixture of CH$_3$OH/H$_2$O (7:3) as mobile phase to afford 0.09 g of Compound 4 (25% yield).

Example 4. Effect of Compound 1 (also Referred to as 6-ECDCA) on Portal Vein Embolization (PVE) in Rabbits Background Complete resection of hepatic tumors is a surgical operation for curative treatment of malignant liver tumors. The remnant liver, however, may be too small to meet the demands of proper liver function and volume. For this reason, the livers in these patients are considered unresectable. Various procedures have been developed to increase the size and function of the future remnant liver (FRL) preoperatively. One procedure to increase the FRL in unresectable patients is portal vein embolization (PVE).

PVE is a clinical procedure that increases hepatic regeneration in the section of the liver in advance of a planned hepatic resection of the other section. During the procedure, a needle is inserted percutaneously into the liver and into the blood vessel on the section of the liver where the greatest part of the tumor is being supplied. Microspheres are infused into the portal vein supplying blood flow to the embolizing area resulting in cutting off the blood flow. This blockade of the embolized lobe prompts the non-embolized lobe to grow, in effect tricking the liver to regenerate. The growth has the effect of enlarging the remaining liver segments on which the patient will depend on after surgery. Patients whose tumors were previously deemed inoperable due to the small amount of liver that would remain, can now undergo surgery to remove the tumor. After several weeks, the non-embolized side of the liver should regenerate to a level where surgery is a viable option.

The results of the in-vivo animal model below demonstrated that 6-ECDCA accelerates liver regeneration and increases liver mass.

Materials and Methods

Animal Study

Female New Zealand White rabbits with a mean weight of 3.0±0.5 kg were acclimatized for 1 week under standardized laboratory conditions in a temperature-controlled room. The animals were individually housed, had free access to standard laboratory food and water, and were subjected to a 12-h light/dark cycle per day. The rabbits were divided into two groups receiving 6-ECDCA and two control groups receiving vehicle. Specifically, the PVE study rabbits were divided into following groups:

Group 1: Normal diet (6-ECDCA 10 mg/kg/day, oral gavage) (N=6), animals sacrificed at day 7, post PVE.
Group 2: Normal diet (Vehicle) (N=6), animals sacrificed at day 7 post PVE.

Group 3: Normal diet (6-ECDCA 10 mg/kg/day, oral gavage) (N=6), animals sacrificed at day 3, post PVE.

Group 4: Normal diet (Vehicle) (N=6), animals sacrificed at day 3, post PVE.

FIG. 1 describes the study outline and schedule for computed tomography (CT) and portography measurements, and portal vein embolization in rabbits.

Portal Vein Embolization

The rabbit liver consists of four liver lobes, three of which are positioned cranially, with the fourth located caudally. In the rabbit PVE model the cranial liver lobes, which account for approximately 80% of the total liver volume, were embolized. The rabbit was placed in a supine position after subcutaneous injection of 0.03 mg/kg buprenorphine and 0.02 mg/kg enrofloxacin. Rabbits were given enrofloxacin 0.02 mg/kg subcutaneously once a day for 3d postoperatively. Animals were anesthetized by intramuscular injection of 25.0 mg/kg ketamine and 0.2 mg/kg dexmedetomidine. Isoflurane 1%-2% with $O_2$/air (1:0.7 L/min) was used to maintain anesthesia. Heart rate and arterial oxygen saturation were measured by pulse oximetry continuously throughout the procedure.

To identify the individual portal branches, portography was performed. After passing the portal branch to the caudal liver lobe, a microcatheter was positioned into the main portal branch supplying the cranial liver lobes. Animals received an initial mixture of contrast (Visipaque) and 90-180 μm polyvinyl alcohol (PVA) particles, followed by injection of 300-500 μm PVA particles until cessation of flow and placement of three platinum coils (6 mm). Portography directly after PVE confirmed total occlusion of the cranial portal blood flow in the embolization groups. The hypertrophy and atrophy responses of the caudal and cranial lobes were measured using CT volumetry before embolization and on day 3 and 7 post-embolization.

CT Volumetry

Multiphasic CT scans were performed using a 64-slice CT scan (Brilliance 64-channel; Philips, Eindhoven, The Netherlands). Rabbits were placed in supine position. After a blank series, a contrast enhanced scan was performed 15 s (arterial phase), 30 s (portal phase), and 45 s (venous phase) after contrast injection (4 mL Visipaque), followed by 3 mL NaCl. 3D-reconstructions of the liver were made using reconstructed 2 mm axial slices. The total liver and the cranial and caudal liver lobes were manually delineated and total liver volume (TLV) and the caudal liver volume (CLV) and cranial liver volume (CrLV) were calculated.

CLV before PVE were expressed as percentage of TLV using the formula:

$$\%CLV_{pre-PVE} = \frac{CLV_{pre-PVE}}{TLV_{pre-PVE}} \times 100\%$$

After PVE, % CLV were calculated using the formula:

$$\%CLV_{past-PVE} = \frac{CLV_{past-PVE}}{TLV_{pre-PVE}} \times 100\%$$

Increase in CLV was calculated using the formula:

$$\text{increase } CLV = \frac{(CLV_{past-PVE} - CLV_{pre-PVE})}{CLV_{pre-PVE}} \times 100\%$$

CrLV was calculated accordingly.

Statistical Analysis

Statistical analysis was performed with Statistical Package for Social Sciences (SPSS 18.0; SPSS, Chicago, Ill.) and GraphPad Prism (GraphPad Software, San Diego, Calif.). CT volumetry data were compared using a mixed-model analysis based on ranked data. Continuous nonparametric data were compared by the Mann-Whitney U test. The Wilcoxon signed rank test was used for nonparametric continuous data for different time points within groups. Correlation between variables was tested using the Pearson r correlation coefficient. All statistical tests were 2-tailed and differences were considered significant at a P value of ≤0.05. Data were expressed as means±SD, unless stated otherwise.

The following measurements were carried out: (1) body weight, (2) computed tomography of the embolized and non-embolized lobes, (3) expression of cell cycle-related and bile salt homeostasis-related transcripts in the liver, (4) expression of ileal transcripts, and (5) serum total bile salt concentration.

Body Weight Measurements

Figure 2:
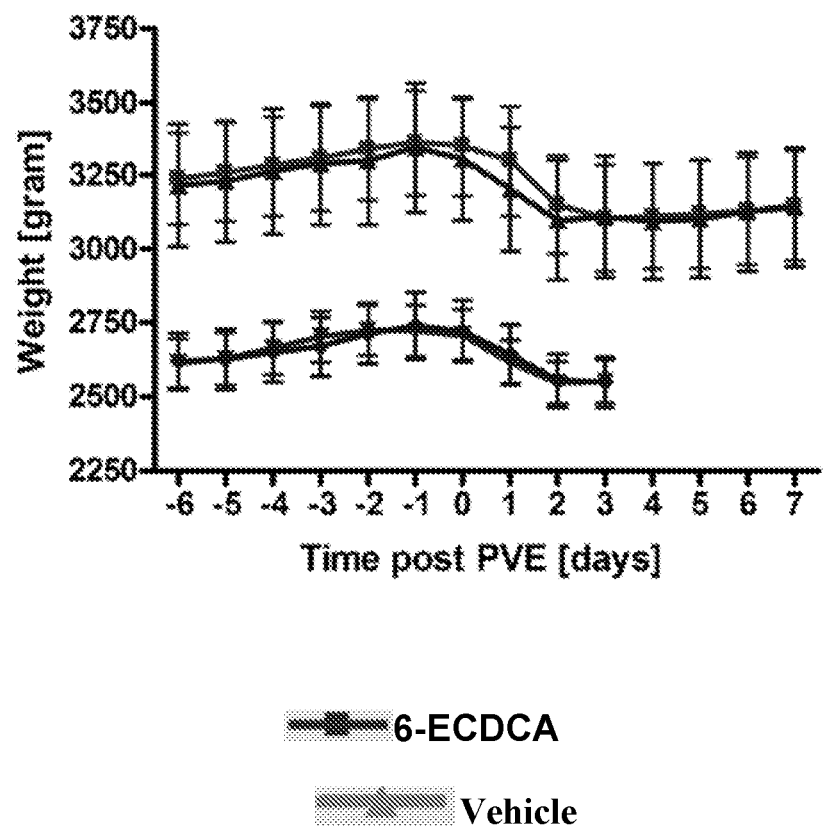
FIG. 2 is a graph indicating the body weight (grams) of the PVE study rabbits versus time (days).

The overall weight of each rabbit was measured on each day of the study and this data is provided on FIG. 2. The data indicates that the difference between the weights of the animals treated with 6-ECDCA or vehicle is not statistically significant.

Computed Tomography

Figure 3:
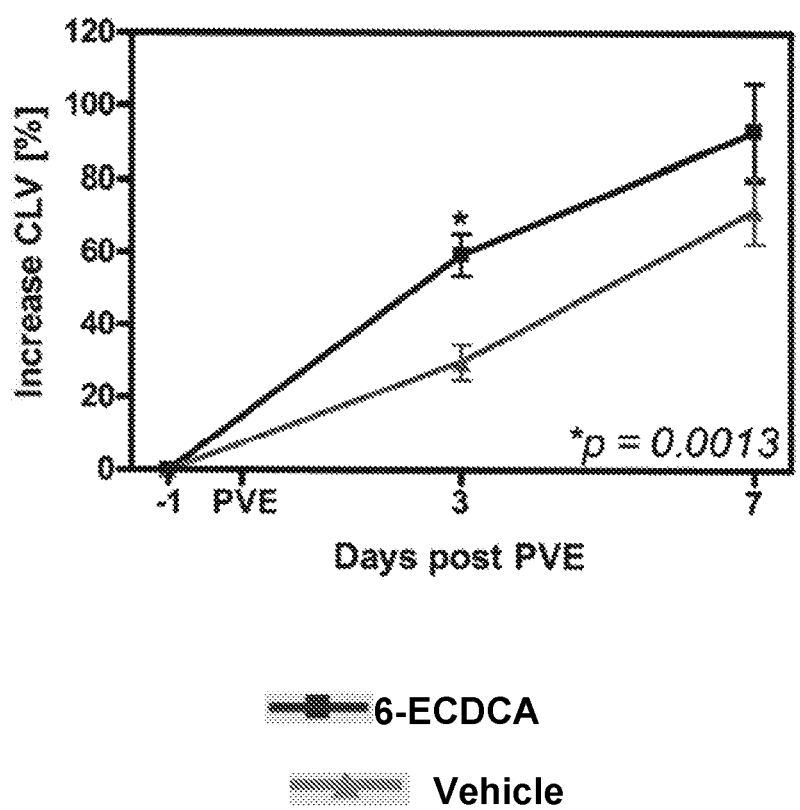
FIG. 3 is a graph indicating the increase in caudal liver volume (CLV, %) of the non-embolized lobe of the PVE study rabbits (n=11 per group) versus time (days).
Figure 4:
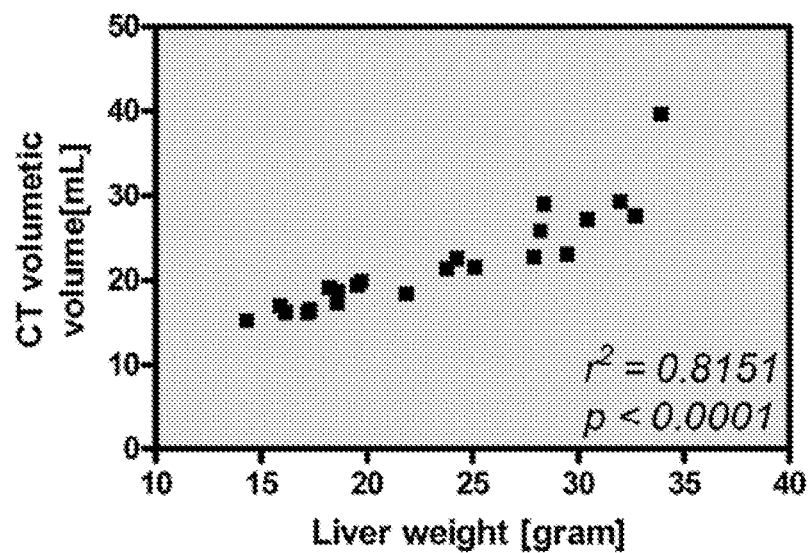
FIG. 4 is a graph indicating the computed tomographic volume (CT, mL) versus liver weight (grams).
Figure 5:
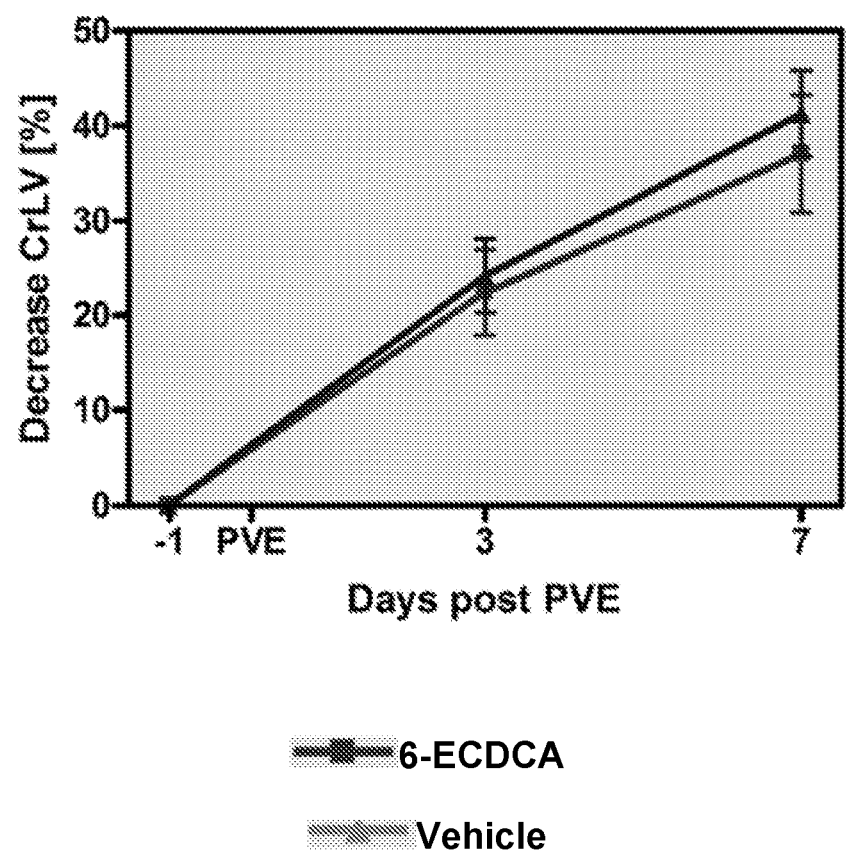
FIG. 5 is a graph indicating the decrease in cranial liver lobe volume (CrLV, %) levels of the embolized lobe of the PVE study rabbits (n=11 per group) versus time (days).
Figure 6A:
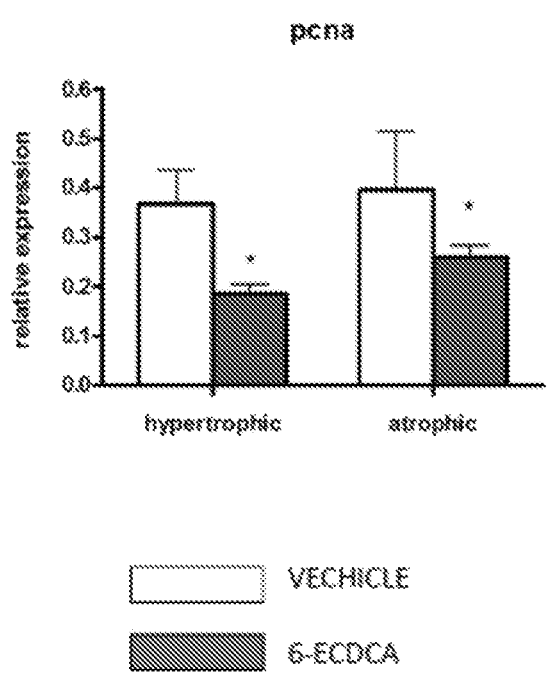
FIG. 6A is a bar graph indicating the relative expression of proliferating cell nuclear antigen (PCNA) in the hypertrophic and atrophic liver sections of the PVE study rabbits 7 days after PVE.
Figure 6B:
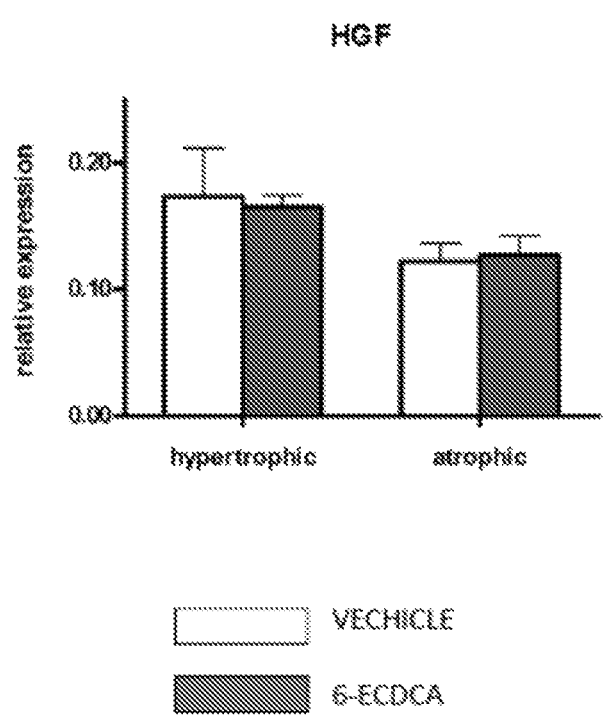
FIG. 6B is a bar graph indicating the relative expression of hepatocyte growth factor (HGF) in the hypertrophic and atrophic liver sections of the PVE study rabbits 7 days after PVE.
Figure 6C:
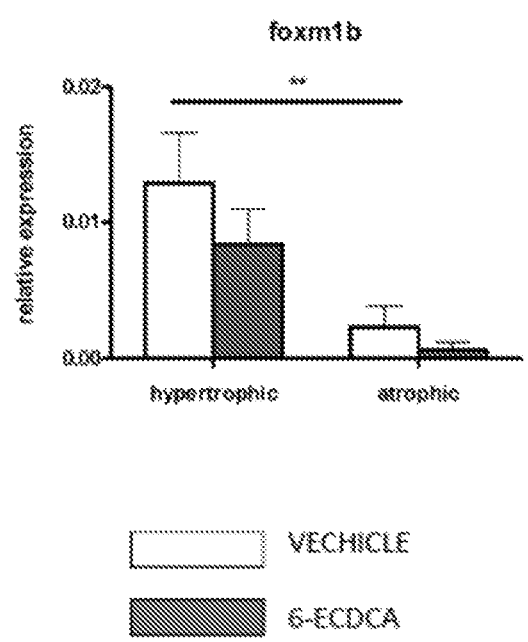
FIG. 6C is a bar graph indicating the relative expression of forkhead box m1b (Foxm1b) in the hypertrophic and atrophic liver sections of the PVE study rabbits 7 days after PVE.
Figure 6D:
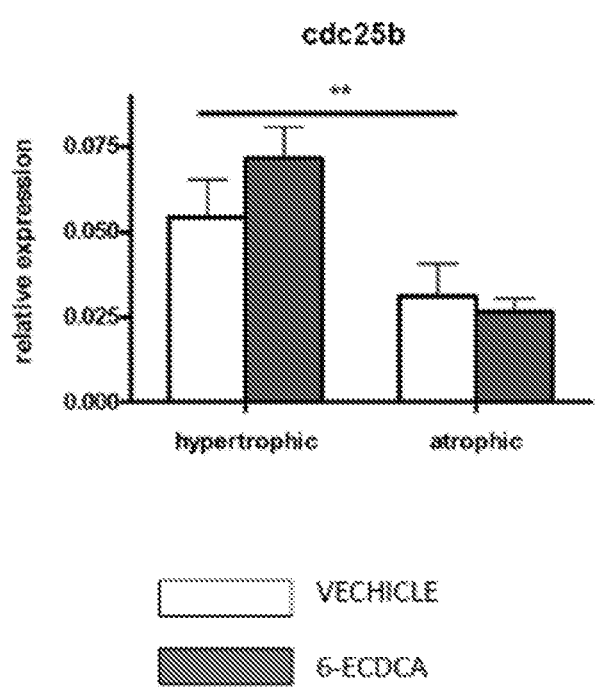
FIG. 6D is bar graph indicating the relative expression of the cell division cycle 25B (Cdc25b) in the hypertrophic and atrophic liver sections of the PVE study rabbits 7 days after PVE.
Figure 6E:
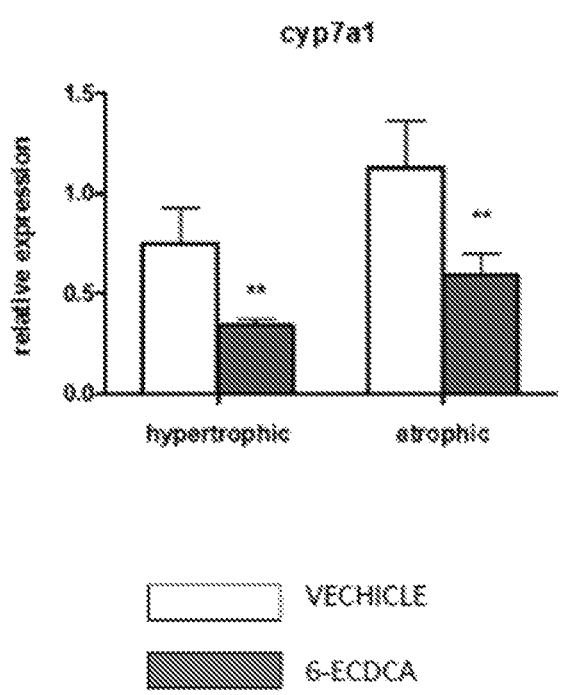
FIG. 6E is a bar graph indicating the relative expression of cholesterol 7 α-hydroxylase (Cyp7a1) in the hypertrophic and atrophic liver sections of the PVE study rabbits 7 days after PVE.
Figure 6F:
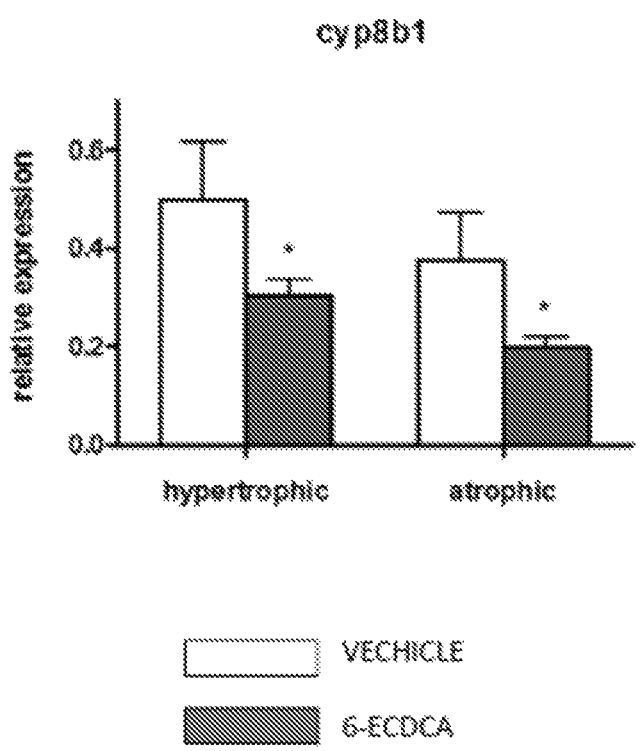
FIG. 6F is a bar graph indicating the relative expression of sterol 12 α-hydroxylase (Cyp8b1) in the hypertrophic and atrophic liver sections of the PVE study rabbits.
Figure 6G:
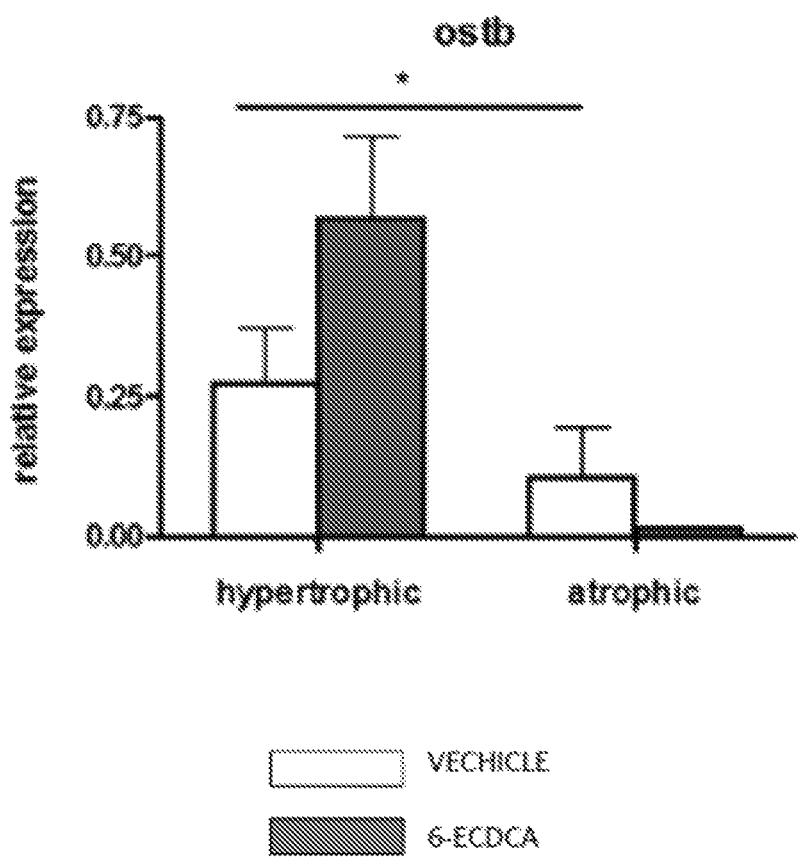
FIG. 6G is a bar graph indicating the relative expression of organic solute transporter beta (OSTB) in the hypertrophic and atrophic liver sections of the PVE study rabbits.
Figure 6H:
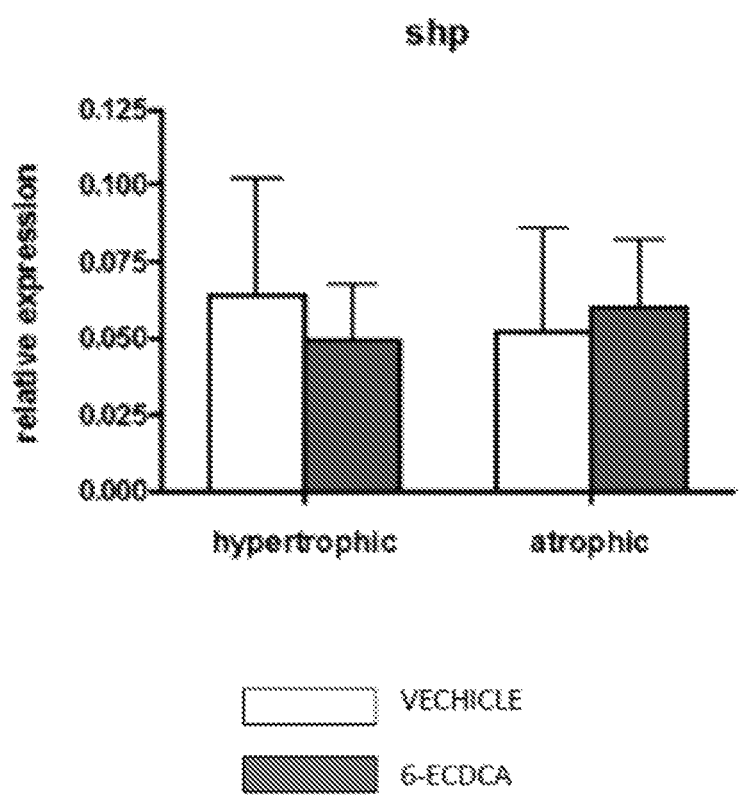
FIG. 6H is a bar graph indicating the relative expression of small heterodimer partner (SHP) in the hypertrophic and atrophic liver sections of the PVE study rabbits.
Figure 7A:
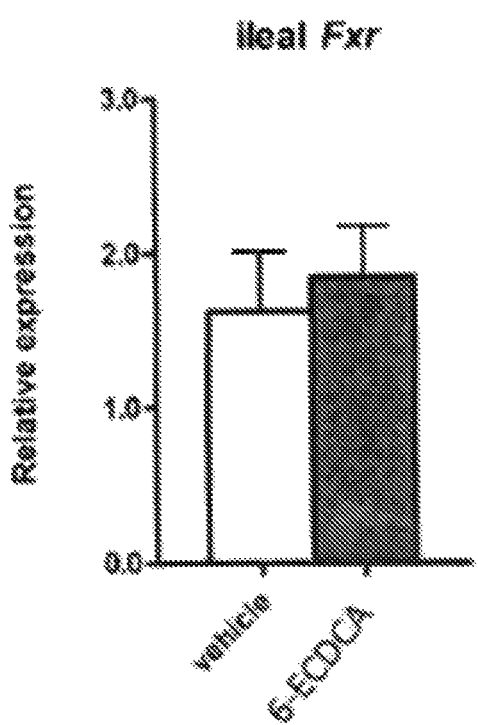
FIG. 7A is a bar graph indicating the relative expression of farnesoid X receptor (FXR) in the ileum of the PVE study rabbits.
Figure 7B:
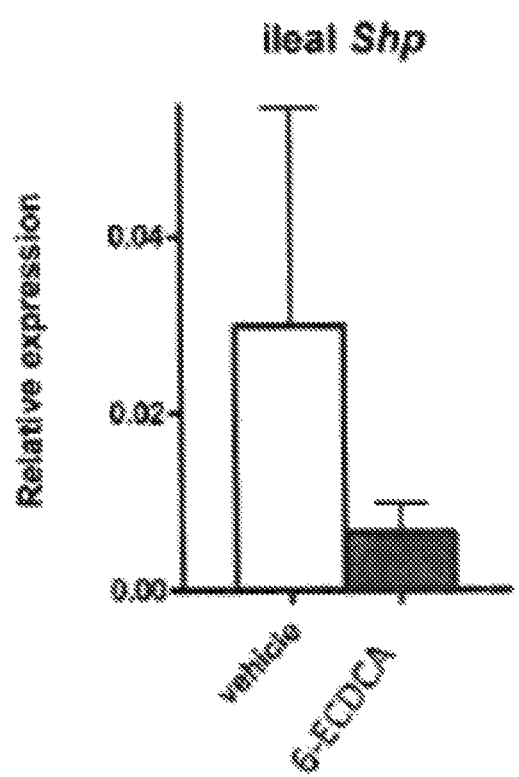
FIG. 7B is a bar graph indicating the relative expression of small heterodimer partner (SHP) in the ileum of the PVE study rabbits.
Figure 7C:
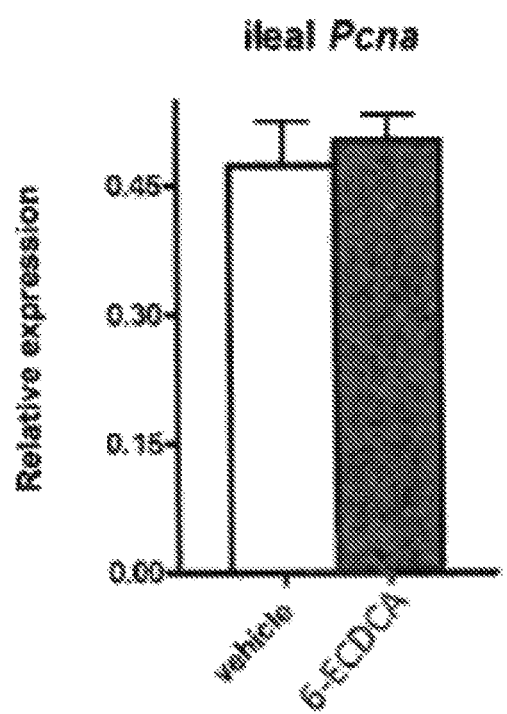
FIG. 7C is a bar graph indicating the relative expression of proliferating cell nuclear antigen (PCNA) in the ileum of the PVE study rabbits.
Figure 7D:
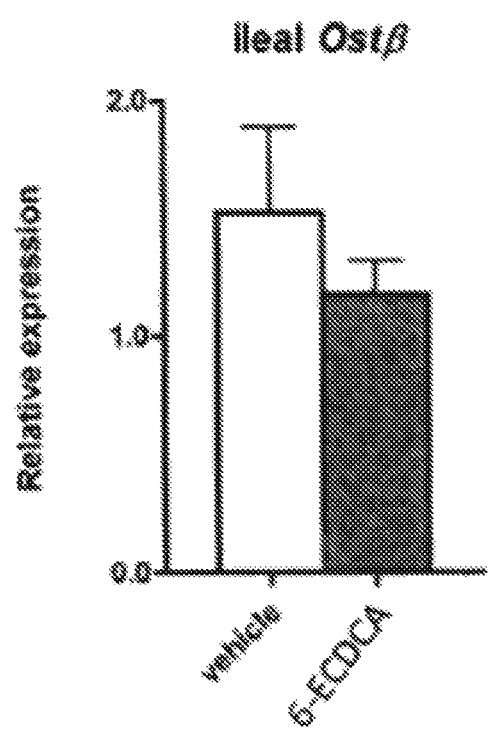
FIG. 7D is a bar graph indicating the relative expression of organic solute transporter beta (OSTB) in the ileum of the PVE study rabbits.
Figure 7E:
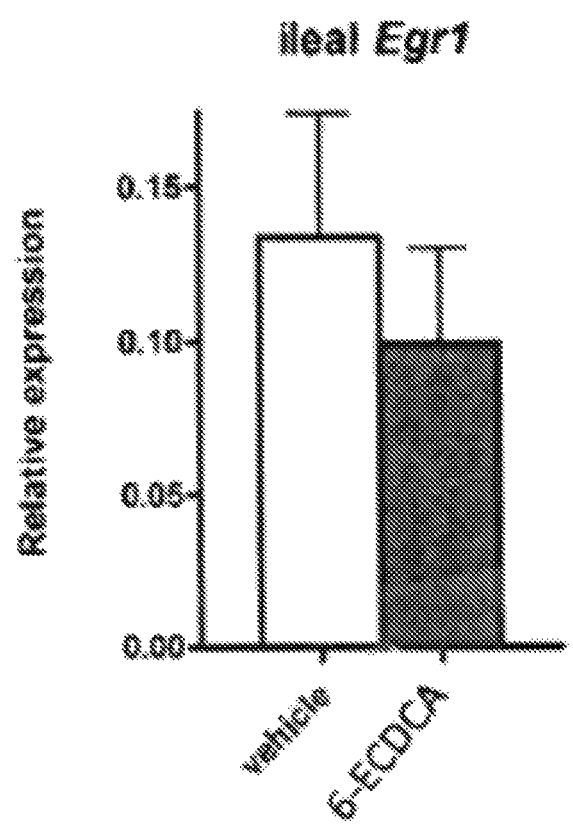
FIG. 7E is a bar graph indicating the relative expression of early growth response protein 1 ($EGR_1$) in the ileum of the PVE study rabbits.
Figure 7F:
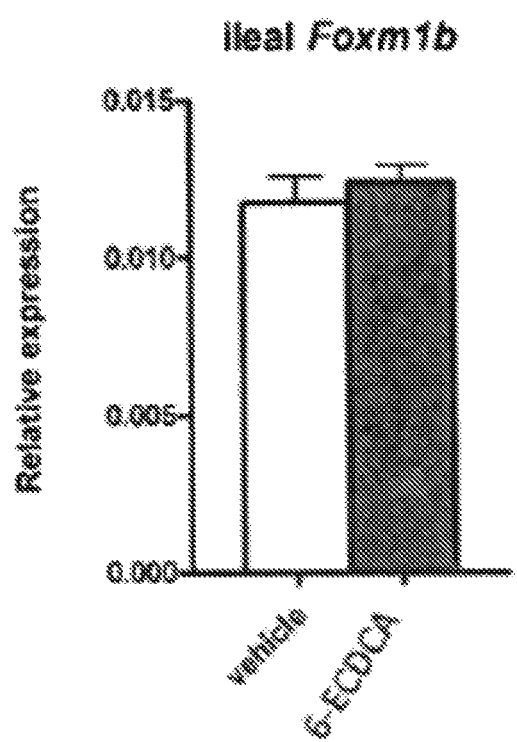
FIG. 7F is a bar graph indicating the relative expression of forkhead box m1b (Foxm1b) in the ileum of the PVE study rabbits.
Figure 7G:
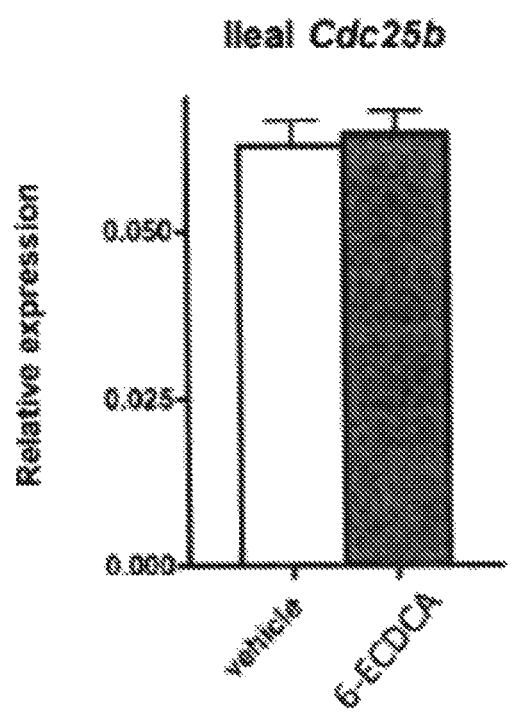
FIG. 7G is a bar graph indicating the relative expression of cell division cycle 25b (cdc25b) in the ileum of the PVE study rabbits.

Computed tomography measurements were performed at baseline, at day 6, and at days 3 and 7 post embolization. FIG. 3 is a graph indicating the increase in caudal liver volume (CLV; %) of the embolized lobe versus time. The data in FIG. 3 demonstrate that 6-ECDCA accelerates hypertrophy of the non-embolized lobe. FIG. 5 is a graph indicating the decrease in cranial liver lobe volume (CrLV, %) levels of the embolized lobe of the PVE study rabbits versus time. The data in FIG. 5 indicate that 6-ECDCA does not affect atrophy of the embolized lobe.

Expression of Cell Cycle-Related and BA Homeostasis-Related Transcripts in the Liver FIGS. 6A-6D describe the effect of 6-ECDCA on the relative expression of cell cycle-related transcripts in the hypertrophic and atrophic sections of the liver at day 7 post embolization. FIGS. 6E-6H describe the effect of 6-ECDCA on the relative expression of bile salt homeostasis-related transcripts in the hypertrophic and atrophic sections of the liver at day 7 post embolization.

Expression of Ileal Transcripts

FIGS. 7A-7G describe the effect of 6-ECDCA on ileal transcripts at day 7 post embolization.

Serum Bile Concentration

Figure 8:
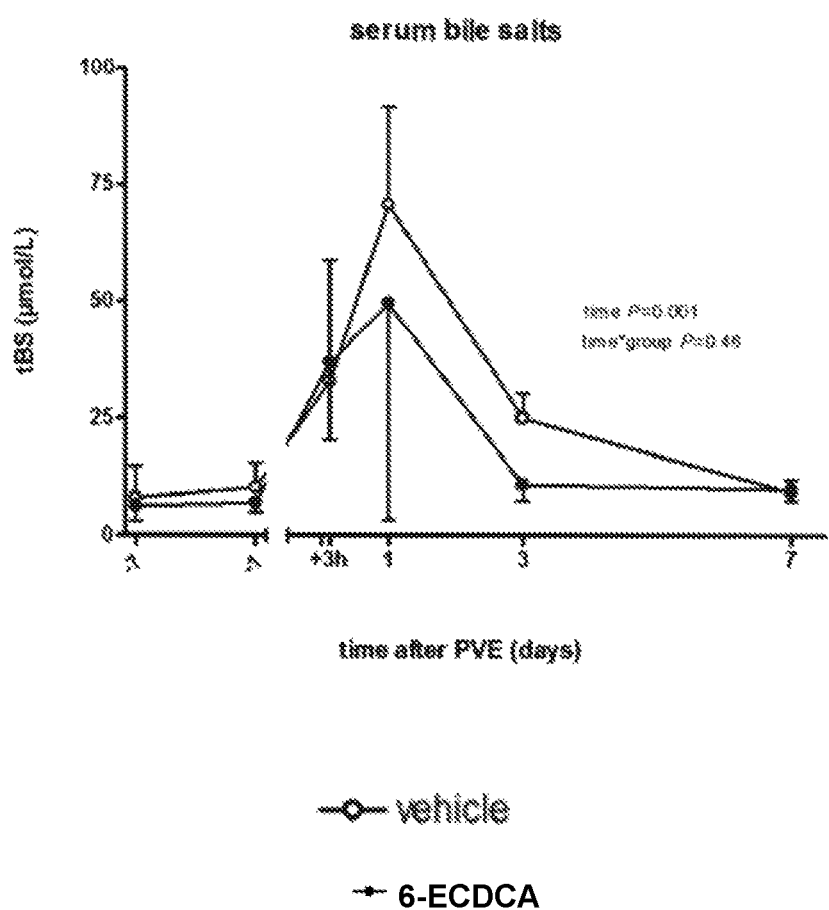
FIG. 8 is a graph indicating the total concentration of serum bile salts (μmol/L) in the PVE study rabbits (n=5 per group) versus time (hours and days).

Serum bile salt concentration was determined at baseline, at 3 h, and at days 1, 3, and 7 post PVE. Total serum bile salts were assayed by an enzymatic method as per manufacturer's instructions (Diazyme Laboratories, Poway, Calif.). FIG. 8 is a graph indicating the total concentration of serum bile salts (μmol/L) in the PVE study rabbits (n=5 per group) versus time (days). Previously, plasma bile salts were examined as predictive factors for the regenerative response following PVE. It was demonstrated that plasma bile salt levels early after PVE strongly correlated with the regenerative response in a rabbit model of PVE (Hoekstra, et al. J. Surgical Research, 2012, 178, 773-778).

In contrast, the data in FIG. 8 indicate that the concentration of the serum bile salts in animals treated with 6-ECDCA was relatively lower at day 1 post PVE compared to control even though 6-ECDCA was shown to accelerate hypertrophy on the non-embolized lobe (see FIG. 3) relative to control.

Example 5. Effect of Compound 1 (also Referred to as 6-ECDCA or OCA or Obeticholic Acid) on Portal Vein Embolization (PVE) in Rabbits Portal vein embolization (PVE) is used to increase future remnant liver volume in patients scheduled for major liver resection. The bile salt-activated transcription factor farnesoid X receptor (FXR) is a key mediator of proliferative bile salt signaling, an event implicated in the early phase of compensatory liver growth following partial hepatectomy. The aim of this study was to evaluate the effect of a potent FXR agonist (obeticholic acid, OCA) on PVE-induced liver growth. Liver growth was assessed by CT scanning, hepatobiliary scintigraphy and image analysis, and by immunohistochemistry for the proliferative marker Ki67. Liver injury was examined by measurement of plasma transaminases and assessment of liver histology.

Thirty six rabbits were randomized between daily oral gavage with OCA (10 mg/kg) or vehicle starting 7 days before PVE and continued until 7 days post-PVE. PVE of the cranial liver lobes was performed using polyvinyl alcohol particles and coils at day 0. Caudal liver volume (CLV) was analyzed by CT volumetry at days −7, −1, +3 and +7. Liver function (i.e. mebrofenin uptake) was quantified in subgroups of animals using hepatobiliary scintigraphy. Additional parameters analyzed were plasma transaminase levels, histological scoring of H&E- and Ki67-stained liver sections, and FXR target gene expression.

Materials and Methods

Animals

The animal ethics and welfare committee of the Academic Medical Center approved all experimental protocols (BEX35AC and BEX35AD). Thirty six New Zealand White rabbits (Charles River, Gennat, France) with a mean weight of 2941(±267) gram were allowed to acclimatize for 1 week before inclusion in the experiments. Rabbits were housed in groups in a temperature-controlled room with a 12 h light/dark cycle and ad libitum access to water and standard chow.

Experimental Design

Six groups of six rabbits were planned for PVE. Animals were randomly allocated to either daily obeticholic acid (Intercept Pharmaceuticals) treatment (10 mg/kg in 1% methyl cellulose) or vehicle (1% methyl cellulose, Sigma Aldrich, Zwijndrecht, the Netherlands) via oral gavage (1.5 mL for a 3 kg animal). Treatment was started 7 days before PVE, and continued until sacrifice at 3 or 7 days after PVE.

Portal Vein Embolization

Animals were anesthetized by subcutaneous injection of ketamine (25 mg/kg, Nimatek, Eurovet, Bladel, The Netherlands) and medetomidine (0.2 mg/kg, Dexdomitor, Orion, Espoo, Finland). Isoflurane 2% (Forene; Abbott Laboratories, Kent, United Kingdom) mixed with $O_2$/air (1:1, 3 L/min) was used to maintain anesthesia. Preoperative analgesia consisted of buprenorphine (0.03 mg/kg, Temgesic, Reckitt Benckiser Healthcare, Hull, United Kingdom). Antibiotic prophylaxis consisted of subcutaneous injection Baytril (0.2 mg/kg body weight, Bayer Healthcare, Berlin, Germany).

PVE was performed as described previously (van den Esschert J W, et al. *Ann Surg* 2012; 255(2):311-8). Following a midline laparotomy, a branch of the inferior mesenteric vein was cannulated using a 18G catheter (Hospira Venisystems, Lake Forest, Ill., US). Under digital subtraction portography a Renegade 3F microcatheter (Boston Scientific, Natick, Mass.) with a Transend-ex 0.36 mm×182-cm guide wire (Boston Scientific) was positioned in the main portal branch to the cranial liver lobes. Polyvinyl alcohol particles (90-180 µm and 300-500 µm in diameter, Cook, Bloomington, Ind.) and 2 fibered platinum coils (4.0 and 6.0 mm; Boston Scientific) were infused through the catheter to occlude the portal branches to the cranial lobes. PVE was confirmed by portography, and the mesenteric vein was closed using a ligature. The abdomen was closed in two layers. Baytril was administered daily for 3 days following PVE.

CT Volumetry

Multiphase CT-scans (Brilliance 64, Philips, Eindhoven, The Netherlands) were performed at day −7, −1, +3, and +7. Animals (n=18 per treatment group) were anesthetized and a 22G catheter was placed in the lateral ear vein. A baseline scan was made and 3 mL of contrast solution (Visipaque, GE Healthcara, Waukesha, Wis.) was injected. Arterial, portal and venous phase scans were made after 15, 30, 45 seconds respectively. Volumetric analysis was performed on 3D reconstruction of 5-mm axial slices using manual delineation. Caudal liver volume (CLV) and total liver volume (TLV) were determined and increase in CLV was determined using the following formula:

$$\% \text{ increase } CLV = \frac{(CLV_{day\ x} - CLV_{baseline})}{CLV_{baseline}} \times 100\%$$

The same formula was used to calculate the decrease in cranial liver volume (CrLV; CrLV=TLV−CLV). Increase in CLV and decrease in CrLV was calculated using day −1 values as baseline. Note that for graphical purposes, changes in CLV and CrLV are displayed starting at day 0 (time point of PVE). Regeneration rate was calculated using the formula:

$$\text{Regeneration rate (\%/day)} = \frac{\text{increase } CLV_{day\ x}}{\text{day } x}$$

Figure 9:
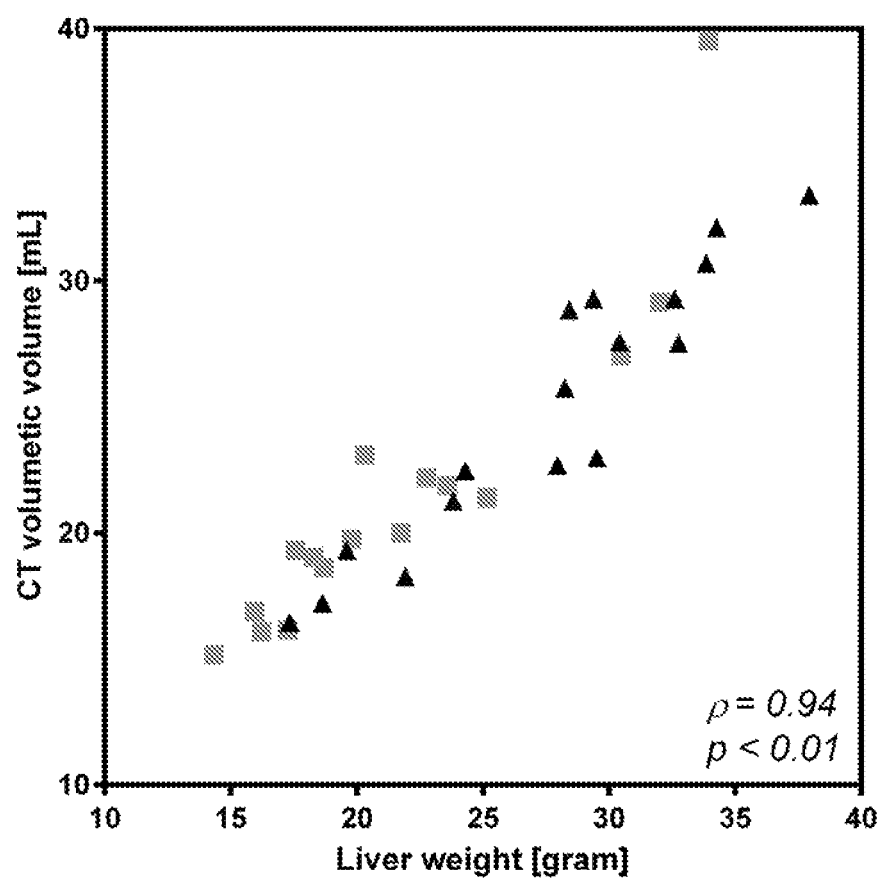
FIG. 9 is a graph of CLV determined by CT volumetry correlated to caudal liver lobe weight at sacrifice.

In order to validate CT volumetric data, the volumetric measurements at sacrifice were correlated to the actual liver weight (precision scale, Sartorius, Gottingen, Germany) at sacrifice (FIG. 9; gray squares represent animals from the control group, black triangles represent animals treated with OCA; correlation was tested using Spearman's rank correlation coefficient).

Hepatobiliary Scintigraphy

Figure 10:
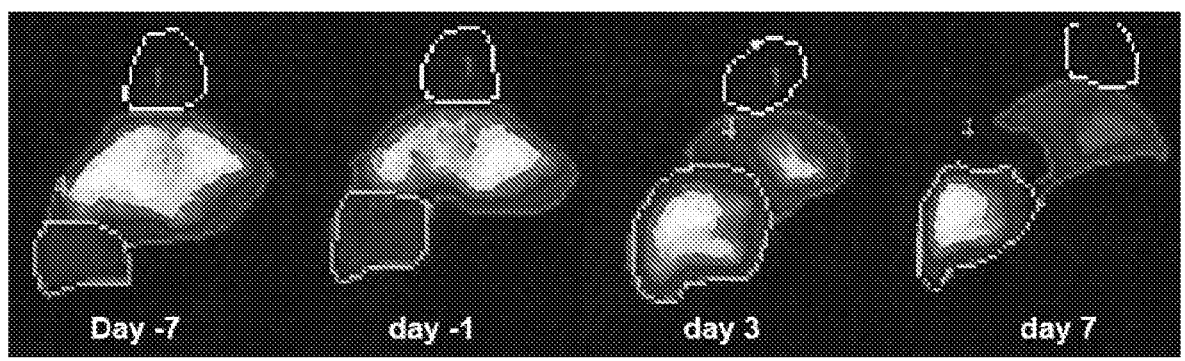
FIG. 10 shows hepatobiliary scintigraphic images of a single rabbit at all sequential scans.

Liver function was assessed using hepatobiliary scintigraphy (HBS) with $^{99m}$Tc-labeled (2,4,6 trimethyl-3-bromo) iminodiacetic acid ($^{99m}$Tc-mebrofenin, Bridatec, GE Healthcare, Eindhoven, the Netherlands) at days −7, −1, +3 and +7. Rabbits (n=6 per treatment group) were anesthetized and positioned on an imaging table with the liver and heart positioned under a large field-of-view single photon emission computed tomography (SPECT/CT) camera (Siemens Symbia T16). Regions of interest were drawn around the left ventricle for blood pool readings, around the entire liver for total liver uptake, and around the caudal liver lobe (FIG. 10; the yellow region of interest (ROI) delineates the left ventricle, the red ROI the total liver and the pink ROI the caudal liver lobe; a marked decrease in cranial liver lobe activity and increase in caudal liver lobe activity was seen following portal vein embolization.). Per rabbit, a dose of 50 MBq $^{99m}$Tc-mebrofenin was administered via a lateral ear vein directly before the start of acquisition.

The geometric mean dataset of the anterior and posterior cameras was used for analysis. Hepatic $^{99m}$Tc-mebrofenin uptake rate was calculated as an increase of $^{99m}$Tc-mebrofenin uptake over two minutes, corrected for perfusion. Total liver uptake was represented by the total hepatic $^{99m}$Tc-mebrofenin uptake rate, and calculated as a percentage of the injected dose per minute. The fractional $^{99m}$Tc-mebrofenin uptake rate was calculated for the caudal liver lobe, based of distribution of segmental activity and was corrected for baseline measurements at t=−7 days.

Histology

Liver tissue (left lateral and caudal lobes) was fixed in buffered formalin for 48 h, and subsequently dehydrated and embedded in paraffin. Four-micron sections of liver tissue were cut and stained with standard hematoxylin and eosin stain. Sections were scored for lobular and portal inflammation according to Table 1. Additionally, liver sections were stained with Ki67 antibodies to quantify hepatocyte proliferation, and hematoxylin counterstain as described in detail previously (van der Loos C M, et al. *J Histochern Cytochern* 2013; 61(1):11-8; Marsman H A, et al. *Br J Surg* 2013; 100(5):674-83). Ki67-positive hepatocytes were counted in a total of five high power fields per animal, by a hepatopathologist (JV) blinded to the group allocation. Liver histology was assessed at day 3 and 7 for n=6 per treatment group.

TABLE 1

| | Scoring | | | |
|---|---|---|---|---|
| Lobular inflammation | 0—None | 1—Mild | 2—Moderate | 3—Severe |
| Intralobular inflammation | 1—<2 foci | 2—2 to 5 foci | 3—>5 foci | |
| Sinuoidal dilatation | 0—None | 1—Mild | 2—Moderate | 3—Severe |
| Foreign body reaction in portal veins. | 0—No | 1—Yes | | |
| Small droplet microvesicular steatosis | 0—None | 1—Mild | 2—Moderate | 3—Severe |

Clinical Chemistry

Serum alanine transaminase (ALT), amino aspartate aminotransferase (AST), gamma-glutamyl transferase (γGT), and alkaline phosphatase (ALP) were determined by the Department of Clinical Chemistry (Academic Medical Center, Amsterdam, The Netherlands) using a Cobas 8000 modular analyzer (Roche, Basel, Switzerland) on samples obtained from 12 animals per treatment group.

PCR (Polymerase Chain Reaction)

Total RNA was isolated from terminal ileum and (non) embolized liver lobes using Tri Reagent (Ambion). Following treatment with DNAseI (Promega, Leiden, the Netherlands), 750 ng total RNA was converted to cDNA using the iSCRIPT cDNA synthesis kit (BioRad, Veenendaal, the Netherlands). Quantitative RT-PCR (real-time polymerase chain reaction) was performed on an IQ5 Cycler using SYBR Green chemistry (SYBR Green MasterMix, BioRad) and cDNA equivalent to 7.5 ng total RNA as template. Expression levels were calculated using LinReg software (Ramakers C, et al. *Neurosci Lett* 2003; 339(1):62-6) and normalized to the geometric mean of Rplp0, Hprt and Gapdh. Primer sequences are provided in Table 2. Predicted product size was checked by agarose gel electrophoresis. PCR analysis was performed using tissue obtained at day 3 and 7 for n=6 per treatment group.

TABLE 2

Primer sequences

| | Forward | Reverse |
|---|---|---|
| Rplp0 | CCTCGTGAGAGTGACATCGT | CGCCCACGATGAAGCATTTT |
| Hprt | GACCAGTCAACAGGGGACAT | ATCCAACAAAGTCTGGCCTGT |
| Gapdh | CCACTACATGGTCTACATGTTCC | TCACCCCACTTGATGTTGGC |
| Fxr | ACAAGTGACGTCGACAACGA | AGGTCTGAAACCCTGGCAAC |
| Slc51b | TGGGAACAGGAGCCAGAAAC | CGTCAGGGCAAGGATGGAAT |
| Shp | GCCCCAAGGAATACGCCTAC | CCGGAATGGACTTGAGGGTG |
| Fgfr4 | GAAAACCAGCAATGGCCGC | GAGCCCCCAAGTGTGAAGAT |
| Klb | GAGAACGGCTGGTTCACAGA | TCGAAGCCATCCAGGAGAGA |
| Cyp7a1 | ATATGATGAGGAGCTCTGAAGC | GGGACTCCTTGATGATGCTGT |

Statistical Analysis

Differences in non-parametric data between groups were tested using Mann-Whitney U-tests or Kruskal-Wallis tests. Effects of OCA on CLV increase or CrLV decrease were analyzed using Mann-Whitney U-tests on values obtained by area under the curve analysis. Differences between plasma laboratory values were analyzes using repeated measurements ANOVA. Correlations were tested using Spearman's rank correlation coefficient. All statistical analysis was performed using Graphpad Prism 6.0 (Graphpad Inc, La Jolla, Calif.).

Results: Obeticholic acid accelerates liver regeneration following portal vein embolization Animals were pre-treated with the FXR agonist obeticholic acid (OCA) for 7 days before undergoing embolization of the cranial liver lobes. Volume of the total (TLV), caudal (CLV, regenerating after PVE) and cranial lobes (CrLV, atrophying after PVE) was assessed during the course of the experiment. Animals were sacrificed at three and seven days after PVE.

Seven days of OCA pretreatment was chosen to ensure adequate tissue levels of OCA at the time of PVE.[24] In mice, diet enriched with cholic acid induced spontaneous liver growth in an FXR dependent manner (Huang W, et al. *Science* 2006; 312(5771):233-6). Therefore, it was first assessed whether liver growth was induced by OCA by analyzing TLV (volume of the total) in the pre-treatment period (day −7 until day −1) (Huang W, et al. *Science* 2006; 312(5771):233-6). At both time points, TLV, corrected for body weight, was similar between groups, and similar between the time points in both groups (FIG. 11A; data were analyzed with Wilcoxon matched-pairs signed rank and Mann-Whitney U-tests. N=17 per group). Thus, OCA did not induce spontaneous liver growth.

Next, the effect of OCA on PVE-induced liver growth was examined. The PVE procedure was tolerated well, although 2 animals died before the end of the experiments due to a technical complication during induction of anesthesia and mesenteric vein cannulation. Accordingly, volumetric data was available for 34 rabbits up to 3 days after PVE, while data from 22 animals was available for liver volume assessment 7 days after PVE.

Liver hypertrophy of the caudal lobe was assessed 3 and 7 days after PVE and expressed as percent increase from day −1 values. At 3 days after PVE, the volume of the caudal non-embolized liver had increased 2.2-fold in the OCA group, compared to the vehicle controls (FIG. 11B, 56.1±20.3% vs. 26.1±15.4%, P<0.001; values represent percentage increase relative to volume at day −1; data were analyzed using Mann-Whitney U-tests on area under the curve values at individual time points. N=17 per group until day 3 and N=11 per group at day 7). At day 7 after PVE, the increase in caudal liver volume remained 1.5-fold higher in OCA-treated animals (102.0±38.2 vs. 67.6±17.7%, P=0.02), indicating that OCA accelerates liver regeneration in the first seven days. The decrease in liver volume of the embolized segments was similar between the two groups (FIG. 11C; values represent percentage decrease relative to volume at day −1; data were analyzed using Mann-Whitney U-tests on area under the curve values at individual time points. N=17 per group until day 3 and N=11 per group at day 7). Without being bound by theory, these data suggest that OCA has direct effects on regeneration and does not affect atrophy of the embolized cranial lobes.

The volume gain induced by OCA is only relevant when actual liver function is also increased. This was assessed by quantifying mebrofenin uptake, a marker for liver function routinely used in clinic-surgical practice. Total liver uptake of mebrofenin was similar at days −1 remained stable in both groups (FIG. 11D; data were analyzed using repeated measurements ANOVA. N=6 per group). The contribution of the non-embolized caudal liver lobe (CLF share) to total liver mebrofenin uptake increased in both groups 3 and 7 days after PVE. However, the increase was greater in OCA-treated animals 3 days after PVE (44.5±5.4% vs. 36.0±3.7%, P=0.02), indicating that OCA promotes increase of functional capacity of the non-embolized liver lobe (FIG. 11E; data were analyzed using repeated measurements ANOVA. N=5-6 per group). In order to examine whether increased volume gain in OCA treated animals reflect hypertrophy or hyperplasia, liver sections were stained for the proliferation marker Ki67, which is not expressed in quiescent hepatocytes. Increased numbers of Ki67-positive hepatocytes were apparent in the OCA group at day +3, with similar numbers in the groups at day +7. (FIG. 11F; data were analyzed using Mann-Whitney U-tests). Increased hepatocellular proliferation thus underlies augmented liver growth in OCA treated animals at day 3 after PVE.

To exclude changes in body weight as a confounding factor in the liver volume calculations, body weight of the animals was measured daily. Body weight decreased after PVE in both groups to a similar extent (FIG. 11G; data were analyzed using repeated measurements ANOVA. N=17 per group). Body weight gain prior to PVE was similar in both groups, indicating that OCA was tolerated well.

In FIGS. 9A-G, * indicates p<0.05,  indicated P<0.01, and * indicated P<0.001 between groups. Abbreviations: OCA, obeticholic acid; TLV, total liver volume; CLV, caudal liver volume; CrLV, cranial liver volume; TLF, total liver function; CLF, caudal liver function.

Summary

Three days after PVE, the increase of CLV in the OCA group was 2.2-fold greater than in controls (56.1±20.3% vs. 26.1±15.4, P<0.001), and this increase remained significantly higher 7 days after PVE (+1.5 fold, P=0.02). The increase in caudal liver function at day +3 was greater in OCA treated animals (+1.2 fold, P=0.02). The number of Ki67-positive hepatocytes was 1.6-fold higher in OCA-treated animals 3 days after PVE (P<0.05). Plasma transaminase levels in the OCA- and vehicle-treated animals were similar and the histological scoring of H&E sections was also similar in both groups. Transcript analysis demonstrated both ileal and hepatic FXR activation.

OCA accelerated liver regeneration after PVE in a rabbit model. OCA treatment could therefore increase the efficacy of PVE and, thereby, prevent liver failure after major liver resection and increase resectability.

This study shows that OCA accelerates volume gain of the non-embolized segment over the first 3 days after PVE through a hyperplastic action. OCA has potential as pharmacologic intervention to enhance liver regeneration.

Obeticholic Acid is not Associated with Notable Hepatocellular and Biliary Injury.

In order to examine whether OCA treatment results in liver injury, transaminase levels were measured during the course of the experiment. PVE induced a transient elevation of ALT and AST, with levels peaking at day +1 in both groups, and returning to baseline values afterwards (FIG. 12A-B). Levels were similar between groups throughout the measurements (FIG. 12A-B). γGT and ALP also remained stable in both groups prior to PVE. After PVE γGT and ALP were slightly higher in OCA treated animals, however levels did not increase above baseline after PVE in both groups. (FIG. 12C, D). These results show that OCA did not cause hepatocellular injury or cholestasis. In FIGS. 12A-D data are presented as mean (±SEM) for n=5-11 per group. Differences between groups were tested using two-way ANOVA. * indicates P<0.05, ** indicates P<0.01.

In order to examine potential effects of OCA on liver histology, H&E stained sections of the caudal lobe were scored in a blinded fashion. Mild portal and lobular inflammation and mild sinusoidal dilatation were observed in all animals with no differences between groups (FIG. 12E; data are presented as median (range) for n=5-6 per group; representative liver sections of both groups at day 3 and 7 with H&E staining at 100× magnification). A foreign body reaction caused by backflow of some embolic material in the caudal lobe was observed in a total of four animals, two in the control group sacrificed at day 3, one in the OCA group sacrificed at day 3 and one in the OCA group sacrificed at day 7. This was not different between groups and the backflow of embolic material did not appear to affect liver hypertrophy. Small droplet macrovesicular steatosis was observed in both groups at day 3 and 7, with no differences between groups, which is consistent with previous observations of mild steatosis in a mouse model of partial hepatectomy (Dai G, et al. *Hepatology* 2008; 47(4):1277-87).

OCA Activates Ileal and Hepatic FXR

In order to assess transcriptional effects of OCA, FXR target gene expression was analyzed in terminal ileum and liver harvested at 3 and 7 days after PVE. FXR is expressed in both terminal ileum and the liver, and it is conceivable that both contribute to liver regeneration in the rabbit (Borude, et al. *Hepatology* 2012; 56(6):2344-52; Zhang, et al. *Hepatology* 2012; 56(6):2336-43).

OCA had no effect on ileal expression of Fxr per se, but resulted in induction of ileal Shp at day +3 (FIG. 13A; animals were pre-treated with obeticholic acid (OCA) for 7 days and underwent embolization of the cranial liver lobes. Terminal ileum (panel A) and caudal liver (panel B) was harvested at sacrifice at three and seven days after PVE. Gene expression was analyzed by RTqPCR. Data are expressed as fold expression compared to the vehicle group. Data are presented as mean (±SEM) for n=5-6 per group. * indicates P<0.05 and ** indicates P<0.01 between groups). This is in line with Shp being a target gene of Fxr. Ileal expression of Ostβ, reported to be regulated by Fxr in rodents and humans (Landrier, et al. *Am J Physiol Gastro-*

*intest Liver Physiol* 2006; 290(3):G476-85; Zollner, et al. *Am J Physiol Gastrointest Liver Physiol* 2006; 290(5):G923-32), was however not affected by OCA. Hepatic expression of the bile salt synthetic enzyme Cyp7a1 was strongly suppressed in OCA treated animals at day +3 (FIG. 13B). This occurred without transcriptional induction of the repressor Shp, suggesting that Shp independent Fgf19 signaling may be responsible for the observed repression of Cyp7a1. The hepatic receptor for Fgf19 is formed by Fgfr4 and βKlotho. Expression of Fgfr4 was not affected by OCA treatment, with minor downregulation at the transcript level was observed for βKlotho after three days (FIG. 13B). These findings are consistent with downregulation of Cyp7a1 by OCA-mediated induction of ileal Fgf19.

OCA treatment resulted in reduced hepatic Fxr expression at day +7. Ostβ expression in the liver was elevated in OCA treated animals at day +3. Conversely, while ileal Shp expression is induced by OCA, this is not observed in the liver. The period between last OCA dose and sacrifice ranged between 9-12 hrs, and may have been suboptimal to observe consistent long-term transcriptional effects. Nonetheless, the aggregated findings from the gene expression analysis indicate that OCA treatment resulted in activation of both ileal and hepatic FXR.

Discussion

In this study the effect of the potent FXR agonist OCA on liver regeneration in a rabbit model of PVE was examined. OCA accelerated liver regeneration in the 7 days after PVE, as evidenced by a 2.2-fold increase in CLV at day 3 and a 1.5-fold increase in CLV at day 7 after PVE in OCA-treated animals compared to vehicle controls. In addition, hepatobiliary scintigraphy revealed an enhanced uptake capacity (1.2 fold, P=0.02) of the caudal liver lobe 3 days after PVE in OCA treated animals. This was accompanied by an increase in number of Ki67+ hepatocytes, indicating that PVE plus OCA elicited a stronger hyperplastic response than PVE without OCA. The accelerated liver regeneration induced by OCA holds great clinical potential.

The current data show that the potent FXR agonist OCA strongly increased the volume gain of the caudal lobe 3 days after PVE in a standardized rabbit model. Increased volume is due to hyperplasia as inferred from enhanced hepatocytic positivity for the proliferative marker Ki67. These results indicate that OCA might be able to reduce the time from PVE to liver resection, which could have several advantages such as avoiding the need for chemotherapy after PVE. Moreover, OCA might improve the liver's growth response to PVE, which could increase the resectability of patients with very small FLRs. Furthermore, when these results are extrapolated to hepatectomy, the increased liver regeneration by OCA could prevent postresectional liver failure. Patients are most prone to liver failure the first days after extended liver resection (Etra J W, et al. *HPB (Oxford)* 2014; 16(10):875-83), and early initiation of liver regeneration is associated with lower incidences of liver failure (Shirabe K, et al. *Scand J Surg* 2013; 102(2):101-5). Through enhancing liver regeneration in these first days, OCA has a benefit in reducing the risk of liver failure and consequent morbidity and mortality.

The volumetric as well as functional gain and increased number of Ki67+ hepatocytes indicate accelerated regeneration, which was most pronounced 3 days after PVE. We have previously shown that functional increase of FRL in patients precedes volumetric increase after PVE (de Graaf W, et al. *Br J Surg* 2011; 98(6):825-34). Thus, OCA-treated animals may have increased uptake capacity over control animals already in the initial period after PVE, prior to assessment of liver function at day +3. In line with the higher metabolic rate in rabbits, regeneration of the liver occurs at a higher pace in rabbits compared to humans, whereas in mice and rats, metabolism is even higher than in rabbits (West G B, et al. *J Exp Biol* 2005; 208(Pt 9):1575-92). The median increase in CLV of 67-71% in vehicle treated rabbits 7 days after PVE (van den Esschert, et al. *Ann Surg.* 2012; 255(2): 311-8).

is comparable to the 62% increase of future remnant liver volume after a median of 34 days in series of select patients who underwent PVE that included segment 4 (Shindoh J, et al. *J Am Coll Surg* 2013; 217(1):126-33; discussion 133-4). In the setting of ALPPS, CLV increase 7 days after PVE corresponds with a 74% increase in FRL volume after a median time of 9 days following the first stage of ALPPS (Shindoh J, et al. *J Am Coll Surg* 2013; 217(1):126-33; discussion 133-4). Therefore, the 7 days in rabbits resemble 4 to 5 weeks of PVE in humans and 9 days after ALPPS. In these time intervals, OCA potentially accelerates the regeneration process in humans.

OCA can be used as a pharmacological intervention that effectively enhances liver regeneration. Using OCA in a rabbit model of PVE, it can be shown that accelerated liver growth in terms of liver volume, liver function and hepatocyte proliferation, without signs of hepatic injury as assessed by histology and plasma transaminases can be achieved. OCA has potential in increasing the efficacy of PVE and reducing the time from PVE to liver resection. as well as in the prevention of postresectional liver failure following major hepatectomy [Olthof, et al. 2016 submitted for publication].

Example 5a. Effect of Obeticholic Acid on Portal Vein Embolization (PVE) in Rabbits Bile salt signaling is required for compensatory liver regrowth following surgical loss of liver tissue. The bile salt receptor FXR plays an important role in this process. In this study we explored whether FXR is involved in the regenerative response following portal vein embolization (PVE), an intervention to increase future remnant liver volume in patients scheduled for extended liver surgery.

Methods

Adult female rabbits received vehicle or the FXR agonist obeticholic acid (OCA; 10 mg/kg, daily oral gavage) for 7 days prior to, and after embolization (day 0) of the cranial liver lobes. Effectiveness of PVE was confirmed by portography, and caudal liver volume (CLV) was analyzed by CT-volumetric analysis at days −7, −1, +3 and +7. Rabbits were sacrificed at day +3 and +7 (n=5-6 per group).

Results

Figure 14:
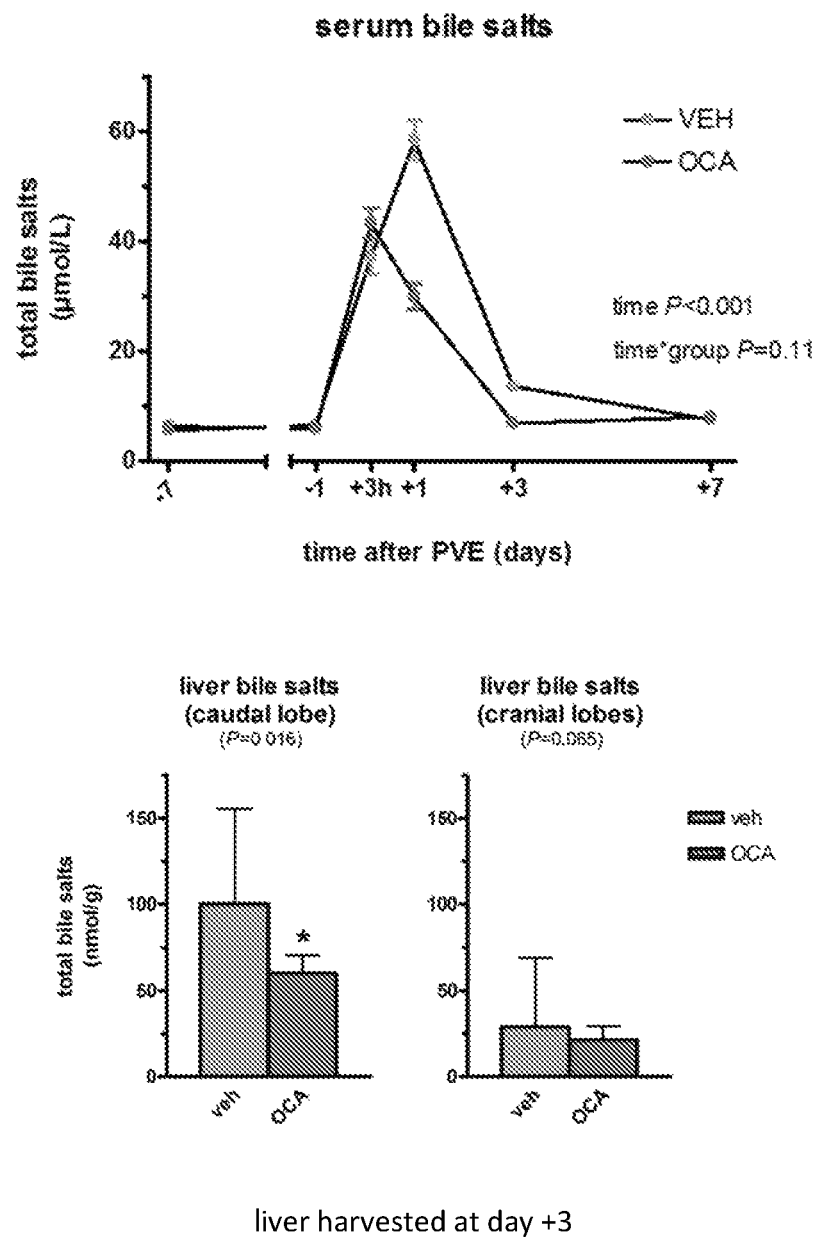
FIG. 14 shows levels of circulating bile salts.
Figure 15:
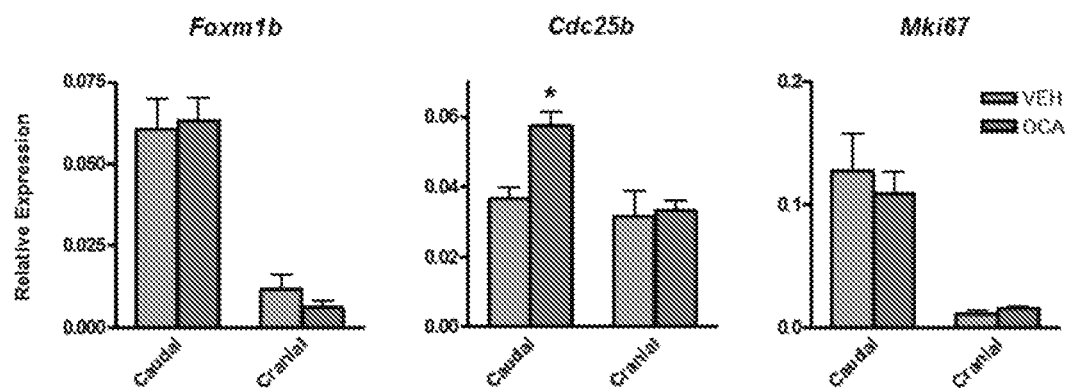
FIG. 15 shows bile salt homeostasis/proliferation related transcript levels.

OCA induced a larger increase in CLV at day 3 after PVE (59.3±19.2% vs 29.7±16.1% in controls, P=0.001), with both groups attaining a similar volume gain after 7 days. In both groups, PVE resulted in a similar pattern of serum bile salt elevation, with levels increasing after 3 hrs and normalizing at day +3. Analysis of tissues harvested at day +3, revealed that hepatic bile salt content was reduced (60.1 [IQR 16.0] vs 100.1 [IQR 75.1] nmol/g in controls; P=0.016) (FIG. 14) in the hypertrophied segments of OCA-treated animals. Reduced expression of the bile salt synthetic enzyme Cyp7a1 (−7.1 fold; P=0.004) and enhanced expression of the basolateral bile salt efflux pump subunit Slc51b (+6.5 fold; P=0.004) may have contributed to this lowering. Expression of Cdc25b, a phosphatase required for entry into mitosis, was elevated in the hypertrophic (+1.6 fold; P=0.006) but not atrophic (+1.1 fold; P=0.52) liver segments of OCA-treated animals. Cdc25b expression in the non-embolized segments correlated with FXR target genes Slc51b ($\rho=+0.80$, $P=0.002$) and Cyp7a1 ($\rho=-0.62$, $P=0.033$), and tended to be associated with percentage increase in CLV at day +3 ($\rho=+0.57$, $P=0.055$) (FIG. 15).

OCA accelerated the PVE-induced volume gain of the caudal lobe through a hyperplastic effect. OCA lowered bile salt content in the expanding caudal lobe. Reduced bile salt synthesis (Cyp7a1) and enhanced bile salt efflux (Ostb) may contribute to the reduced caudal bile salt content. OCA enhanced expression of Cdc25b, a phosphatase required for entry into mitosis, in the caudal lobe. This correlated with expression of FXR-regulated genes, and tended to be associated with CLV gain.

Conclusions

OCA accelerated liver regeneration in the first 3 days after PVE in rabbits, with control and OCA-treated animals having a similar volume gain in the non-embolized segments after 7 days. Improved bile salt homeostasis and induction of proliferative genes (e.g. Cdc25b) may underlie the augmented growth rate in the initial phase after PVE.

OCA treatment has potential in extending resectability of hepatic lesions and prevention of post-resectional liver failure.

Example 6. The FXR Agonist Obeticholic Acid Induces Liver Growth in Rats with Obstructive Cholestasis Materials and Methods Animals Adult male Wistar rats (300-325 g) were purchased from Harlan (Horst, the Netherlands), acclimated for one week, and housed under standardized laboratory conditions (12 h light-dark cycle, room temperature=$21\pm2°$ C., humidity=$50\pm10\%$) with unlimited access to water and chow (Hope Farms, Woerden, the Netherlands). Prior to each surgical procedure, animals received 0.025 mg/kg of buprenorphine subcutaneously as analgesia, after which general anesthesia was induced and maintained with a mixture of air/$O_2$ (1:1 volume ratio, 2 L/min) and 2-3% of isoflurane (Forene, Abbott Laboratories, Chicago, Ill.). The core body temperature of all rats was maintained at $37.0\pm0.2°$ C. with a heating mat and heating lamp during the procedure [NRC 2011].

Experimental Design

After the acclimatization period, the rats either continued on a regular chow diet or were switched to a methionine and choline-deficient (MCD) diet (Harlan Teklad, Madison, Wis.) for 3 weeks to induce moderate hepatic steatosis [Heger 2011a]. At the start of the second diet week, the rats either underwent sham surgery or were subjected to reversible bile duct ligation (rBDL). For rBDL, the extrahepatic bile duct was cannulated with a polyethylene catheter (length=$\pm1.5$ cm, inner diameter=0.4 mm, outer diameter=0.9 mm, Braun, Melsungen, Germany) connected to Silastic Tubing with a closed distal tip (length=$\pm7.5$ cm, inner diameter=0.8 mm, outer diameter=1.4 mm, Dow Corning, Midland, Mich.) [Kloek 2008]. Sham-operated animals underwent abdominal surgery, including bile duct mobilization, without inducing a biliary obstruction. Groups of rBDL rats were left untreated or received a daily oral gavage of the FXR agonist obeticholic acid (OCA, 10 mg/kg in 0.5% methylcellulose, 1.5 mL per 300 g body weight) between 7:30 and 9:00 AM.

Seven days after BDL or sham operation, all rats were subjected to 70% PHx [DeGraaf 2011]. In all rBDL rats, intestinal bile flow was restored directly prior to PHx by removing the closed cannula tip and inserting the cannula into the duodenum. Animals in all treatment groups were put on regular chow after PHx. OCA treatment was continued after PHx until sacrifice. As depicted in Scheme 1, the study consisted of five experimental groups (n=4-6 animals per group per time point): control (sham), steatosis (MCD), cholestasis (rBDL), combined steatosis and cholestasis (rBDL+MCD), and cholestasis+OCA (rBDL+OCA).

Scheme 1 (FIG. 23) shows a schematic overview of the study design. One hundred thirty rats were divided over five study arms. Animals were sacrificed before partial hepatectomy (PHx, i.e., sacrifice day 0) or 1-5 days after PHx (n=4-6/group). In the rBDL groups, biliary drainage was performed directly after PHx (rBDL=reversible bile duct ligation; Chol.=cholestasis; MCD=methionine and choline-deficient diet; OCA=obeticholic acid; rBDL=reversible bile duct ligation; steatochol.=combined simple steatosis and cholestasis).

At baseline (i.e., directly before PHx) and one to five days after PHx, animals were euthanized under isoflurane anesthesia by exsanguination. Blood samples were collected from the caval vein in heparin-anticoagulated vacutainers (BD, Franklin Lakes, N.J.) and centrifuged for 10 min ($3000\times g$, $4°$ C.). In rBDL animals sacrificed at baseline, bile was aspirated with a syringe from the dilated extrahepatic bile duct, weighed, and stored at $-80°$ C. The liver and ileum were excised, weighed, loafed, and either fixed in a 10% (vol/vol) neutralized formalin solution (J. T. Baker, Center Valley, Pa.), snap-frozen in liquid nitrogen and stored at $-80°$ C., or collected in RNAlater (Qiagen, Venlo, the Netherlands) and stored at $-20°$ C. Liver regrowth was calculated from the regenerated liver mass, and was expressed as percentage of total liver mass prior to PHx. The projected remnant liver mass was calculated using the weight of the resected liver segments, which represent 70% of the total liver mass. Dry liver weights were measured to correct for hepatic water content [Kloek 2010a].

Histology

After formalin fixation, liver specimens were dehydrated, paraffin-embedded, and stained with hematoxylin and eosin (H&E), the collagen type I and III stain picrosirius red, or the proliferation marker Ki67 [Marsman 2013]. Semi-quantitative analysis of H&E- and picrosirius red-stained liver histology was performed by an experienced hepatopathologist (JV) blinded to the experimental groups using a scoring system detailed in Table 1. Ki67-positive hepatocyte nuclei were manually counted by two observers (RFG and PBO) in four randomly-selected microscopic fields at 200× magnification.

TABLE 1

| Histological scoring system | |
| --- | --- |
| Confluent necrosis | |
| Absent | 0 |
| Present | 1 |
| Ductular reaction | |
| Absent | 0 |
| Periportal | 1 |
| Septal | 2 |
| Cirrhosis | 3 |
| Fibrosis | |
| Absent | 0 |
| (Peri)portal inflammation | 1 |
| Septal/bridging | 2 |
| Cirrhosis | 3 |

Quantitative Real-Time Polymerase Chain Reaction

Transcriptional analysis was performed [Olthof 2015]. Liver samples were homogenized with a MagNA Lyser and total RNA was extracted with the High Pure RNA Tissue Kit (both from Roche Applied Sciences, Penzberg, Germany). One µg of RNA was reverse transcribed to cDNA using the SensiFAST cDNA Synthesis Kit (Bioline, London, UK) according to manufacturer's instructions. Quantitative reverse transcriptase polymerase chain reaction was performed on a LightCycler 480 (Roche, Basel, Switzerland) using SensiFAST SYBR No-ROX mix (Bioline). Fluorescence data was processed and analyzed and normalized to hypoxanthine-guanine phosphoribosyltransferase (Hprt) for ileum samples, and the geometric mean of ubiquitin C (Ubc) and beta-2-microglobulin (B2m) for liver samples. These reference genes proved most stable over the experimental groups and time points (data not shown). Primers were designed using NCBI Primer Blast (http://www.ncbi.nlm.nih.gov/tools/primer-blast/) to span an intron or exon-exon junction and prevent amplification of residual genomic DNA (Table 2). Melting curve analysis and agarose gel electrophoresis were used to validate primer specificity.

homogenate was centrifuged for 10 min at 10,000×g (4° C.) and the TNF-α and IL-6 levels in the supernatant were measured by ELISA as per the kit manual (R&D systems, Minneapolis, Minn.). The cytokine concentration was normalized to the homogenate protein content (Protein Assay Kit, Pierce, Rockford, Ill.).

High Performance Liquid Chromatography Analysis of Bile Acid Pool Composition

Bile acids were separated and quantified by reverse-phase high-performance liquid chromatography (HPLC) [Lionarons 2016]. Bile or plasma samples (20 µL) were deproteinated by the addition of 5 volumes of acetonitrile. Following centrifugation (10 min at 20,000×g), solvent was evaporated from supernatants and bile salts were solubilized in 200 µL of 25% methanol. For liver homogenates, 100 mg liver tissue was sonicated for 30-90 s in 500 µL of water. One mL of acetonitrile was added for protein precipitation. Samples were subsequently centrifuged at 20,000×g for 10 min, after which the supernatant was used for analysis. Results were corrected for homogenate protein content. One hundred µL of sample was applied to a Hypersil C18 HPLC column (Thermo Scientific, Waltham, Mass.) operated at 20° C. The

TABLE 2 qRT-PCR primers

| Target | Forward (5'→3') | Reverse (5'→3') |
| --- | --- | --- |
| Cyp7a1 | GCAGCCTCTGAAGAAGTGAGTGG | GATGCTGTCTAGTACCGGCAGG |
| Ntcp | TGAACCTCAGCATCGTGATGACC | GGACGATCCCTATGGTGCAAGG |
| Mrp3 | ATGCTGGCCAAAATGCGGTTGC | CCAGGAGCCCTTGCAGTATTCC |
| Mrp4 | GTTCTGGCAAAGACCTTGGATGC | CCGTGTATTCAATCACCCTCTCC |
| Bsep | CTCTGCTTTGCCTTTTCCCAGG | AGAGACCACCCTGAAAACGTGG |
| Mrp2 | GAGTCTGAGGATGAATCTCGACC | TGCCCTATGCTCAGGTTGTCACC |
| Fxr | GTCATCCTCTCTCCAGACAGACA | GGTTGAATGTCCGGAGTTCTGTC |
| Shp | GCTAGAGGAACCCAACAGTGGT | CCTGGCACATCTGGGTTGAAGA |
| Ostβ | ACGACCGTGCATTCCTGAGTGGGTC CCTGCTGTTGCGAG | CAAGGAGTTGCATCCTCTGAACGC GTCTCTGGGCCTGGATCTGG |
| B2m | CCACCGGAGAATGGGAAGCCC | TCTCGGTCCCAGGTGACGGT |
| Ubc | ACACCAAGAAGGTCAAACAGGAAGA | AGACACCTCCCCATCAAACCCA |
| Foxm1 | AGGCGCCCTCAAGAGCATCA | TGGTrCCAACACTTCCAGCCT |
| Ccnd1 | AGTGTGACCCGGACTGCCTC | CCTCGGTGGCCTTGGGATCG |
| Fgfr4 | AGCTCCAGGCGGGTGAGTGT | CGCTGACCACCTTCCTGGCT |
| Fgf15 | AGGGCCAGAAACCTTCAAAC | GATCCATGCTGTCGCTCTC |
| Cyp8b1 | CCTGAAGGGAATGCGGGCCA | TGGGGCCAAAGGAGAGGGGA |
| Stat3 | CCGGCAAGGGCTTCTCGTTCTG | CCCGGGGGCTTTGTGCTTAGGAT |
| Socs3 | GGGGCCCCTTCCITTTCTTTACCA | GGCCCCCTCTGACCCTTTCTTTG |
| Tgfβ | ATACAGGGCTTTCGCTTCAGTGCT | CCCGGGTTGTGTTGGTTGTAGAG |
| Hprt | CCTCAGTCCCAGCGTCGTGATTA | TCAGCACACAGAGGGCCACA |

Cytokine Measurements

A Diax 900 tissue homogenizer (Heidolph, Schwabach, Germany) was used to homogenize±100 mg of rat liver on ice in 1400 µL of 5 mM NaPi buffer (pH=7.4) containing a protease inhibitor cocktail (cOmplete ULTRA, Roche). The starting eluent consisted of 6.8 mM ammonium formate (pH=3.9), followed by linear gradient or isocratic elution with acetonitrile at the following concentrations: 28% (1 min), 38% (13 min), 42% (19 min), 61% (20 min), 63% (25 min), 80% (28 min), 80% (31 min) and 0% (33 min). The flow rate was 0.8 mL/min. Detection was done using a Nano Quantity Analyte Detector QT-500 (Quant Technologies, Blaine, Minn.). Bile acids were quantified using a separate calibration curve per species. Biliary bile acid concentrations were multiplied by the total volume of bile to calculate biliary bile acid output.

Statistical Analysis

All statistical analyses were performed with GraphPad Prism (version 6.0, La Jolla, Calif.) abiding by a significance level (a) of 0.05. All numerical variables were assumed to (approximately) follow a Gaussian distribution and were therefore analyzed using a Student's t-test or one-way ANOVA with Tukey' s post-hoc correction. Paired variables were analyzed using a paired t-test. Histological scoring was analyzed using chi-square tests. Correlations were tested using Pearson product-moment correlation coefficient.

Results

Obstructive Cholestasis Impairs Liver Regeneration following Partial Hepatectomy Liver regeneration is often studied in animals with healthy livers, which is in stark contrast with surgical practice that is dominated by patients with a liver affected by chemotherapy, steatosis, cholestasis, or a combination of these factors. As these conditions impair liver regeneration and negatively affect post-operative outcomes [DeMeijer 2010; Farges 2013; Hubert 2015], the first aim was to investigate liver regeneration after 70% PHx under various conditions of parenchymal pathology. The effects of rBDL and MCD treatment on parenchymal inflammation prior to PHx were reported previously [Lionarons 2016].

Figure 16:
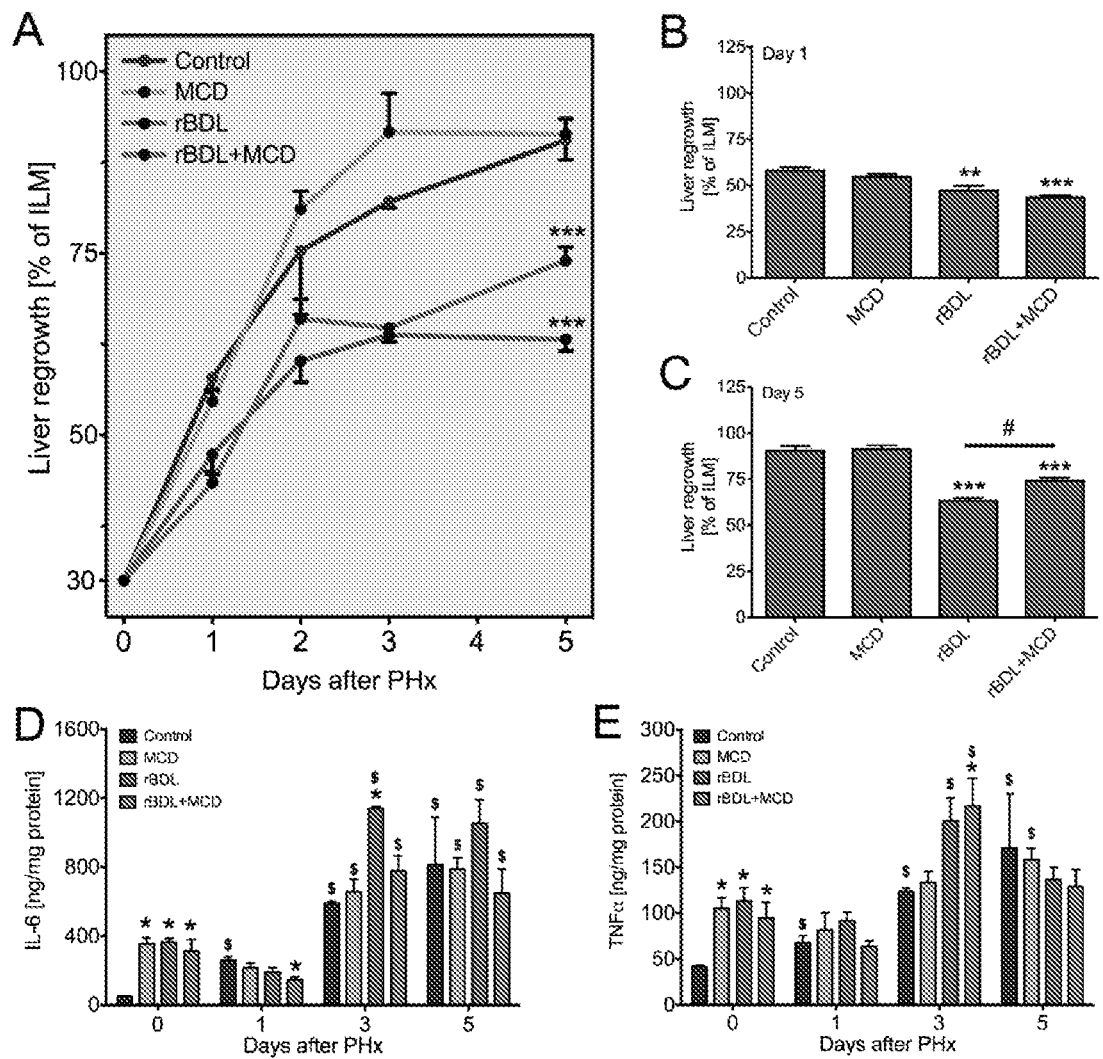
FIG. 16A-E shows effects of parenchymal liver disease on regeneration following partial hepatectomy.

FIG. 16 shows that healthy rat livers regenerate to approximately 90% of their original mass in five days after PHx (FIG. 16A, second, Control curve). Rat livers with simple steatosis regenerated as effectively as undamaged livers (FIG. 16A, first, MCD curve), which corroborates earlier findings that steatohepatitis rather than the more prevalent simple steatosis compromises hepatic regeneration [Marsman 2013; Reiniers 2013; Reddy 2012; Farrell 2002]. In contrast, liver regrowth was markedly impaired in rBDL animals with and without simple steatosis (FIG. 16A-C). Impaired liver regeneration in these groups was already manifest one day after PHx (FIG. 16A-B). The growth of rBDL livers stagnated on day 2 after PHx and did not exceed 60% of the initial liver mass, which was less than in the other study arms (FIGS. 16A and C).

In line with the liver regeneration paradigm [Fausto 2006; Michalopoulos 1997], hepatic levels of the cytokines Il-6 and Tnf-α were quantified to determine whether the diverging regrowth rates were related to post-PHx cytokine production. Inherent to pre-existent inflammation [Lionarons 2016], hepatic cytokine levels were already elevated prior to PHx in all animals with parenchymal liver disease (FIG. 16D-E). Il-6 and Tnf-α increased on day 1 after PHx in healthy rats compared to baseline, whereas this increase was not observed in the other study groups (FIG. 16D-E). The lack of a post-PHx cytokine surge could contribute to defective liver regrowth in rats with pre-existent parenchymal liver injury. Based on the regeneration profiles (FIG. 16A), the remainder of the experiments focused on improving liver regeneration after PHx in rBDL animals.

Obeticholic Acid Induces Liver Growth in Cholestatic Rats Prior to Liver Resection The diminished regenerative potential of rBDL rats (Scheme 1) likely results from abrogated intestinal Fxr signaling caused by interrupted intestinal BA delivery and toxicity associated with intrahepatic BA accumulation. Impaired liver regeneration in rBDL rats could be ameliorated by restoring intestinal FXR signaling through oral administration of the FXR agonist OCA.

Figure 17:
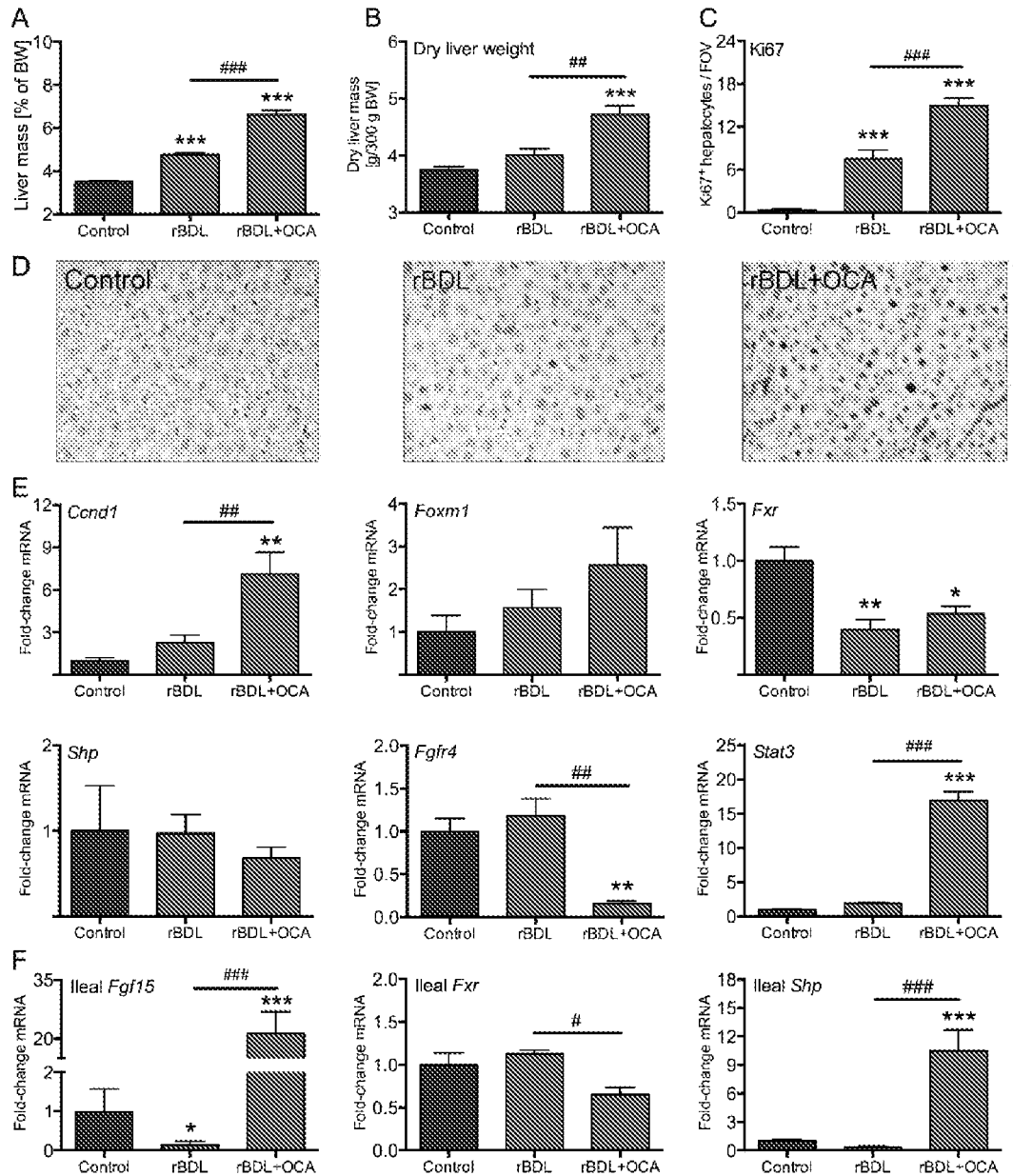
FIG. 17A shows the total liver weight (expressed as percentage of body weight) of controls (sham surgery) and after 7 days of rBDL with or OCA treatment.
FIG. 17B shows the total liver weight (expressed as dry weight per 300 g body weight) of controls (sham surgery) and after 7 days of rBDL with or OCA treatment.
FIG. 17C shows representative Ki67-stained liver sections.
FIG. 17D quantitative assessment of Ki67 positivity.
FIG. 17E shows expression levels of proliferation- and FXR-related genes in liver.
FIG. 17F shows expression levels of proliferation- and FXR-related genes in ileum.

Gross liver mass of animals sacrificed prior to PHx was higher in both rBDL groups compared with the control group (FIG. 17A). However, after correcting for hepatic water content (e.g., due to inflammatory edema), increased liver mass was only observed in OCA-treated animals (FIG. 17B), confirming that rBDL-induced cholestasis was associated with inflammation (Lionarons, et al. *Sci Rep.* 2016, 6:31829) and that OCA stimulated liver growth. Accordingly, hepatocyte proliferation measured by Ki67 staining and expression of cell cycle marker CyclinD1, encoded by Ccnd1, was more pronounced in the rBDL+OCA group compared to untreated rBDL or non-cholestatic animals (FIG. 17C-E). Both Ki67 staining and Ccnd1 expression also correlated positively with dry liver mass (FIG. 18A-C). As hepatocytes in non-injured liver are in a quiescent state (FIG. 17C-D), these results suggest that proliferation in the rBDL groups is part of a hepatic homeostatic response that aims to repair cholestatic liver damage. However, liver hyperplasia did not occur during the seven-day rBDL period in the absence of OCA treatment (FIG. 17B), despite the proliferative signaling.

OCA-induced hepatocyte proliferation reportedly proceeds via a direct (hepatic) pathway and/or an indirect intestinal pathway. The direct pathway is mediated by the hepatocellular Fxr target gene Foxm1 [Zhang 2012], which mediates cell cycle progression and is indispensable for effective liver regeneration after PHx [Huang 2006; Chen 2010c; Wang 2002a]. The indirect pathway involves intestinal Fxr-linked production of mitogenic Fgf15 and signaling via hepatic Fgfr4 [PadrissaAltés 2015; Kong 2014; Uriarte 2013]. It should be noted that there is no consensus on whether the indirect pathway also increases hepatic Foxm1b expression [Zhang 2012; PadrissaAltés 2015].

Figure 18:
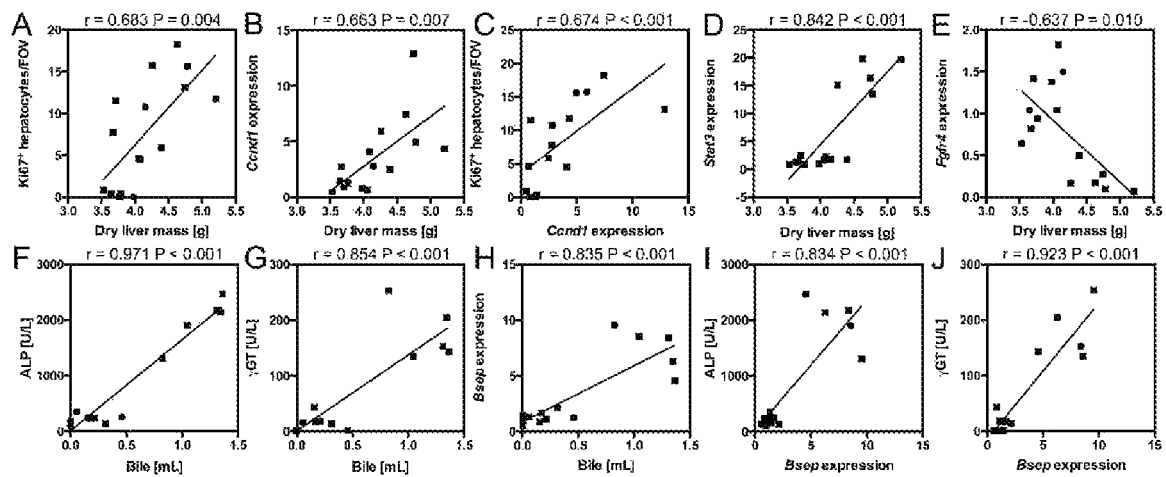
FIG. 18 shows correlation analysis of liver growth and hepatobiliary injury parameters.

Hepatic expression levels of Fxr and Foxm1 were comparable between both rBDL groups (FIG. 17E). Accordingly, the direct pathway was most likely not responsible for the proliferative signaling induced by OCA. In contrast, ileal Fgf15 transcription was strongly upregulated (~20-fold) in rBDL rats receiving OCA, and this coincided with marked upregulation of the Fxr target gene Shp (FIG. 17F). Thus, OCA treatment led to activation of intestinal Fxr, with a minor downregulation of ileal Fxr itself. Ileal Fgf15 and Shp expression was strongly suppressed in untreated rBDL animals (FIG. 17F), likely owing to the failed delivery of ileal Fxr ligands (i.e., BAs) after rBDL [Naugler 2014]. Fgf15 binds to its cognate (co)receptors Fgfr4 and βKlotho on hepatocytes, which leads to proliferative signaling through activation of the Stat3 pathway [PadrissaAltés 2015]. Although Fgfr4 was downregulated at the transcript level (FIG. 17E), possibly through a negative feedback loop [Fong 2003; Wong 2002], Stat3 was considerably upregulated (FIG. 17E), suggesting that signaling through Fgfr4 was still effective. Accordingly, Fgfr4 transcript levels were negatively correlated to dry liver mass, while Stat3 transcript levels exhibited a strong positive correlation (FIG. 18). Above findings support the involvement of the gut-liver axis in liver growth in rBDL rats treated with OCA.

FIGS. 17A-F show that obeticholic acid induces hepatocyte proliferation and hepatomegaly in cholestatic rats prior to liver resection. Specifically, FIGS. 17A-B show the total liver weight of controls (sham surgery) and after 7 days of rBDL with or OCA treatment (liver weight is expressed as percentage of body weight (A) or as dry weight per 300 g body weight (B)); representative Ki67-stained liver sections (C) and quantitative assessment of Ki67 positivity (D); and expression levels of proliferation- and Fxr-related genes in liver (E) or ileum (F) (wherein BW=body weight; FOV=field of view; OCA=obeticholic acid; rBDL=reversible bile duct ligation (cholestasis).* indicates p<0.05,  indicates p<0.01, and * indicates p<0.001, all versus the control group. # indicates p<0.05, ## indicates p<0.01, and ### indicates p<0.001, all versus the experimental group indicated by the solid line).

Liver Regrowth after Partial Hepatectomy is Stalled in Post-Cholestatic Rats Receiving Obeticholic Acid After establishing that OCA increases the size of cholestatic livers, it was investigated whether OCA also accelerates liver regeneration following 70% PHx. Unexpectedly, liver regrowth was stalled in OCA-treated rBDL animals compared to untreated rBDL and control rats (FIG. 19A). There are two possible explanations for this unexpected finding. First, Fgfr4 expression was markedly downregulated on the day of PHx (FIG. 19D). The slower recovery of liver mass in the OCA group could therefore result from reduced relay of mitogenic Fgf15 signaling. The finding that Fgfr4 transcript levels were elevated on day 1 after PHx in control and untreated rBDL animals supports this line of thought (FIG. 19D, discussed below). Moreover, the early induction of Fgfr4 following PHx in rBDL rats not treated with OCA is followed by a sharp decline of Fgfr4 mRNA levels on day 2 after PHx, which coincides with the cessation of liver regrowth (FIG. 19AD). Second, the dry weight of the remnant liver at the time of PHx was already higher in the OCA group than in the other two groups (FIG. 19B). As the rate of liver regeneration is proportional to the amount of liver removed, and thus inversely related to the size of the remnant liver [Michalopoulos 1997; Yamanaka 1993], the reduced regrowth rate after PHx in OCA-treated animals may have resulted from the expansion of liver size before resection. In line with this premise, the liver-to-body-weight ratio of rBDL+OCA rats was similar to control animals five days after PHx (FIG. 19B). This ratio remained lower in the untreated rBDL group relative to controls, indicating that the slower regeneration rate in the OCA group ultimately did not compromise the extent of liver mass restoration.

To closer investigate these findings, the expression of FXR-related genes and proliferation parameters were monitored the first five days after PHx. Apart from Fgfr4, hepatic Fxr was markedly upregulated on day one after PHx in controls and untreated rBDL rats (FIG. 19D). The simultaneous induction of Ccnd1 (FIG. 19D) and appearance of Ki67+ hepatocytes (FIG. 19C) in these groups supports previous notions that an Fxr-Fgf15-Fgfr4 signaling axis is required for liver regeneration (Uriarte, et al. *Gut.* 2013, 62(6):899-910; Naugler *PLoS One.* 2014, 9(5):e97426). Accordingly, the stagnating regrowth in untreated rBDL animals on day two after PHx was paralleled by a loss of Fxr and Fgfr4 expression (FIG. 19A-D). This finding could not only explain the exhaustion of regeneration in cholestatic livers, but also strengthens the rationale for targeting this pathway to enhance liver regeneration.

In line with the strong pre-PHx induction of intestinal Fgf15 expression (FIG. 17), hepatic Fgfr4 expression remained low on OCA-treated animals during the regrowth phase. Effects of OCA on hepatic Fxr were most pronounced the first two days after Phx, as is indicated by the high transcript levels of the Fxr target Shp relative to untreated rBDL and control rats. The latter is supported by the slight decrease in liver Fxr mRNA on day 1 post-PHx. Despite the successful induction of hepatic Fxr targets by OCA, hepatic Foxm1 expression did not change during liver regeneration in any group (FIG. 19D).

In contrast to the regrowth kinetics, the number of Ki67+ hepatocytes was highest in the OCA group on day one after PHx (FIGS. 19C and 20), which indicates increased proliferation. This discrepancy may stem from the OCA-induced increase in liver mass prior to PHx. The induction of proliferative signaling by OCA before resection may have caused the peak in Ki67 staining observed on day one after PHx, while the loss of Fgfr4 expression and induction of signals for termination of liver regeneration such as transforming growth factor beta (Tgfβ) and suppressor of cytokine signaling 3 (Socs3) (FIG. 19D) could account for the delayed recovery of liver mass in the OCA group. This stalled regrowth in the OCA group also fits the 'hepatostat' paradigm (Moschetta, et al. *Gastroenterology,* 2015, 149(3): 537-40; Naugler, et al. *Gastroenterology* 2015, 149(3):728-40), as livers that are larger prior to PHx (i.e., OCA-treated livers (FIG. 17B) require less expansion to reach a fixed, predefined liver-to-body-weight ratio. This notion is substantiated by FIG. 19B, which shows that liver size in the OCA group was comparable to healthy controls five days after PHx.

Figure 19:
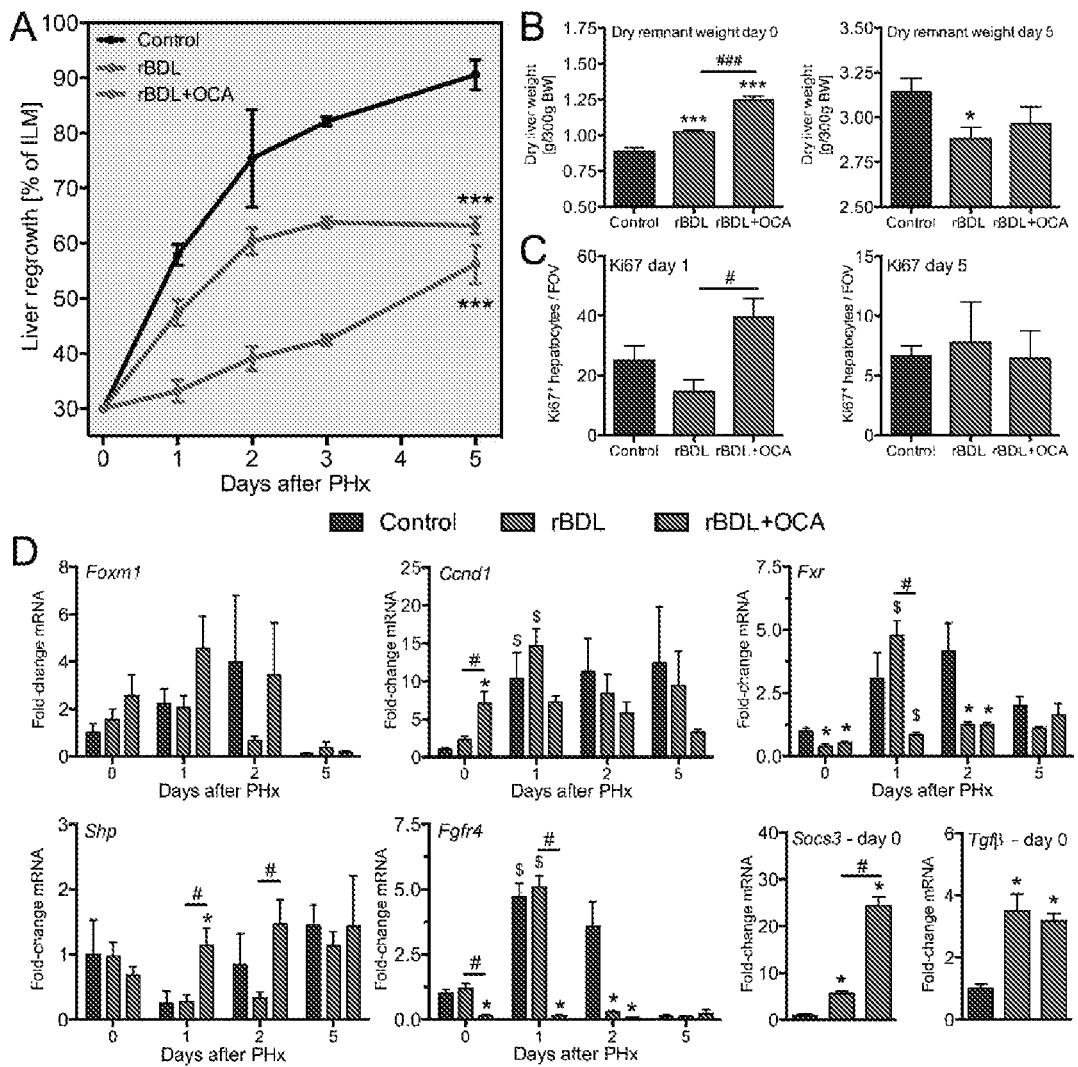
FIG. 19A shows liver regrowth after partial (70%) hepatectomy (PHx) of healthy rats (top line), post-cholestatic rats (rBDL, middle line), and rBDL rats treated with obeticholic acid (OCA, bottom line).
FIG. 19B shows dry weights over the remnant liver immediately (left) and five days after PHx (right).
FIG. 19C shows the number of proliferating hepatocytes on day 1 (left) and day 5 (right) after PHx.
FIG. 19D shows the hepatic expression of various proliferation and FXR-related genes.
Figure 20:
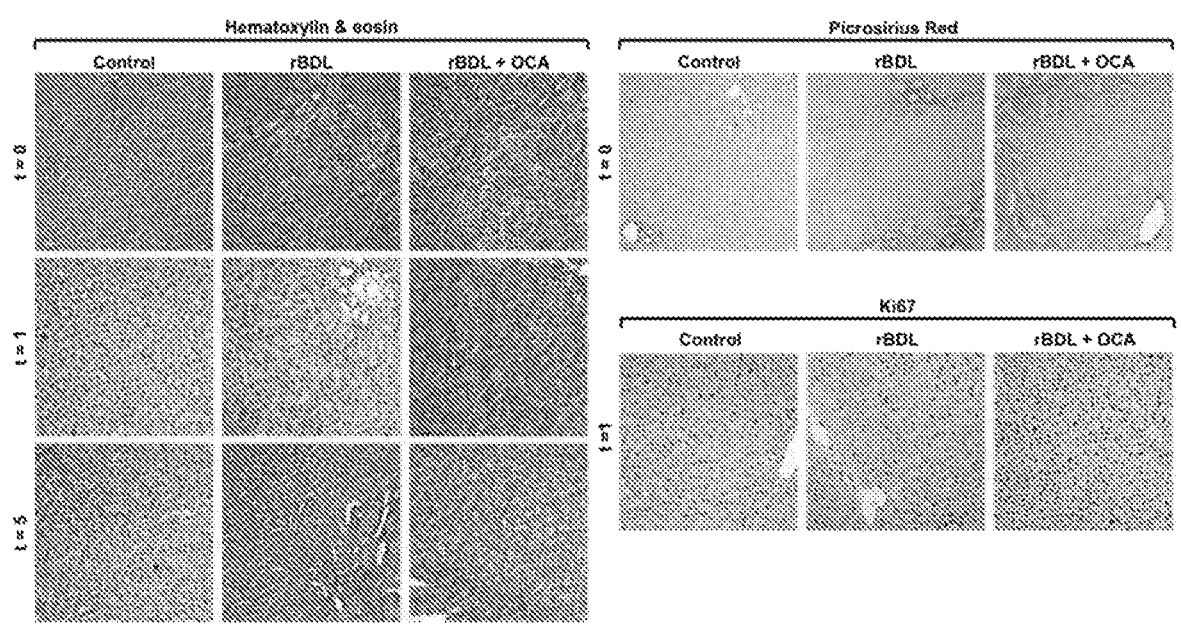
FIG. 20 shows representative images of hematoxylin and eosin-(H&E, left), picrosirius red-(PSR, top right) and Ki67-stained liver slides.

FIG. 19 shows that liver regrowth is stalled in post-cholestatic rats treated with obeticholic acid. Specifically, FIG. 19A shows liver regrowth after partial (70%) hepatectomy (PHx) of healthy rats (black line), post-cholestatic rats (rBDL, green line), and rBDL rats treated with obeticholic acid (OCA, red line). FIG. 19B shows dry weights over the remnant liver immediately (left) and five days after PHx (right). FIG. 19C shows the number of proliferating hepatocytes on day 1 (left) and day 5 (right) after PHx. FIG. 19D portrays the hepatic expression of various proliferation and Fxr-related genes (BW=body weight; rBDL=reversible bile duct ligation (cholestasis); OCA=obeticholic acid. * indicates p<0.05 versus the control group. # signifies p<0.05 versus the experimental group indicated by the solid line. $ indicates p<0.05 versus baseline (day 0) within an experimental group).

OCA Aggravates Biliary Injury during Obstructive Cholestasis by Modulating Bile Acid Transport It has been demonstrated that Fxr agonists [Liu 2003] or the Fxr target FGF19/Fgf15 [Luo 2014; Modica 2012] attenuate cholestatic liver injury. It has been also found that genetic deletion of Fxr actually reduces BDL-induced liver injury by altering BA detoxification and excretion [Wagner 2003a; Stedman 2006]. To further examine the effects of OCA treatment, serum and histological markers for hepatic injury were assessed prior to PHx and the first five days after PHx. The expression of various genes related to BA homeostasis was monitored concomitantly.

Cholestasis

Prior to PHx, alanine aminotransferase (ALT) and alkaline phosphatase (ALP) levels were considerably higher in rBDL rats receiving OCA than in the other two groups, indicating aggravated hepatobiliary injury (FIG. 21A-C). Plasma gamma glutamyltransferase concentrations followed the same dynamics as ALP. Histological analysis revealed a similar extent of hepatocellular necrosis and fibrotic changes in the rBDL groups at the time of PHx (FIG. 21D). As histological changes are a lagging indicator for cholestatic injury, the apparent disconnect between plasma and histological injury profiles probably relates to the relatively short duration of combined OCA treatment and BDL.

To explore the effects of OCA on liver biochemistry at baseline, the expression of various Fxr target genes related to BA metabolism and transport was assessed. RBDL rats adapted to BA overload by upregulating basolateral BA exporter Mrp3 FIG. 21F, which is analogous to the response seen in cholestatic mice and patients [Schaap 2009; Boyer 2006]. OCA treatment led to a more robust induction of Mrp3 than in untreated rBDL animals (FIG. 21F), and concurrently upregulated basolateral BA exporters Ostβ and Mrp4 (FIG. 21F). In addition, the archetypal Fxr target Bsep, coding for the canalicular BA exporter, was almost 8-fold upregulated (FIG. 21F). As OCA induces choleresis [Roda 2014; Fiorucci 2005a], the liver injury profile at baseline is likely caused by forced pumping of BAs via Bsep into the obstructed biliary tree. This can cause biliary infarcts due to heightened biliary pressures [Wagner 2003a; Fickert 2002]. The substantial increase in bile retrieved from the extrahepatic bile duct and elevated biliary BA output after seven days of OCA treatment also supports this notion (FIG. 21E). Comparable side effects of choleretics on BDL-induced liver injury have been observed [Weerachayaphorn 2014]. A crucial role for Bsep in mediating this effect is supported by previous findings that pharmacological suppression of Bsep reduces cholestatic injury in mice [Chen 2015]. The latter is also corroborated by the positive correlation between Bsep expression, extrahepatic bile volume, and markers for biliary injury (FIG. 18) seen prior to PHx. Despite the reduction in hepatic BA load by OCA (FIG. 21E), hepatocellular injury was also increased in OCA-treated animals at baseline (FIG. 21A). This could either be secondary to ductular reaction and related neutrophil influx (FIG. 20) or could relate to the slight changes in the composition of the BA pool in favor of the more toxic chenodeoxycholate (FIG. 22).

Notably, the basolateral BA importer Ntcp was mildly upregulated in the OCA group (FIG. 22E), whereas Ntcp is normally repressed by Fxr during cholestasis to limit hepatocyte BA loading [Zollner 2005; Lionarons 2016]. A similar loss of Ntcp suppression was previously seen in mice with intrahepatic (but not extrahepatic) cholestasis treated with Fxr agonist GW4064 [Liu 2003]. It was also expected that hepatic Cyp7a1 would be repressed by OCA [Liu 2003], either via Shp, via Fgf15-Fgfr4, or a combination of both [Inagaki 2005; Modica 2012; Naugler 2015; Li 2014a]. Despite signs of hepatocyte Fxr activation (discussed above) and ileal Fgf15 expression (FIG. 22F), OCA did not alter hepatocyte Shp (FIG. 21D) or Cyp7a1 mRNA levels (FIG. 22F). Both findings reaffirm that (regulation of) BA synthesis during cholestasis is not independently controlled by FXR and SHP, but involves other BA receptors and transcriptional (co)activators such as, e.g., the pregnane X receptor and hepatic nuclear factors [Geier 2005; Fiorucci 2014]. The interspecies differences in regulation of Ntcp [Jung 2004; Geier 2007] and Cyp7a1 [Wagner 2003a; Schaap 2009] under cholestatic conditions could also explain these observations. The rise in hepatic BA content caused by rBDL, however, was effectively counteracted by OCA treatment (FIG. 22E), which suggests that sustained BA production by Cyp7a1 and BA uptake by Ntcp during OCA treatment likely has little harmful consequences.

Regeneration

Consistent with the restoration of regular bile flow, hepatobiliary injury markers normalized within 48 h after PHx in rBDL groups, albeit recovery was more gradual in OCA-treated animals (FIG. 22A-C). Despite a ~4-fold decline, ALP levels remained higher in the OCA group than in the other study arms during regeneration (FIG. 22B). Bilirubin clearance also lagged marginally in OCA-treated animals (FIG. 22C), which in light of the low ALT values may reflect impaired canalicular bilirubin export by MRP2 and compensatory basolateral export by MRP3 (FIG. 22F) [Keppler 2014] rather than compromised liver function. On a histological level, the modest degree of hepatocellular necrosis seen in the rBDL groups prior to PHx gradually subsided during the regeneration phase (FIG. 5F), which is consistent with the downward trend in serum injury markers. Periportal fibrosis with a non-ductular etiology was observed in all control animals on day 5 after PHx, suggesting this is part of the normal regenerative response. A similar degree of periportal to septal fibrosis was seen in both rBDL groups. This indicates that the increase in biliary injury markers caused by OCA prior to PHx did not exacerbate liver injury after hepatectomy. Accordingly, there was no mortality noted in any study group during the regeneration phase.

Figure 21:
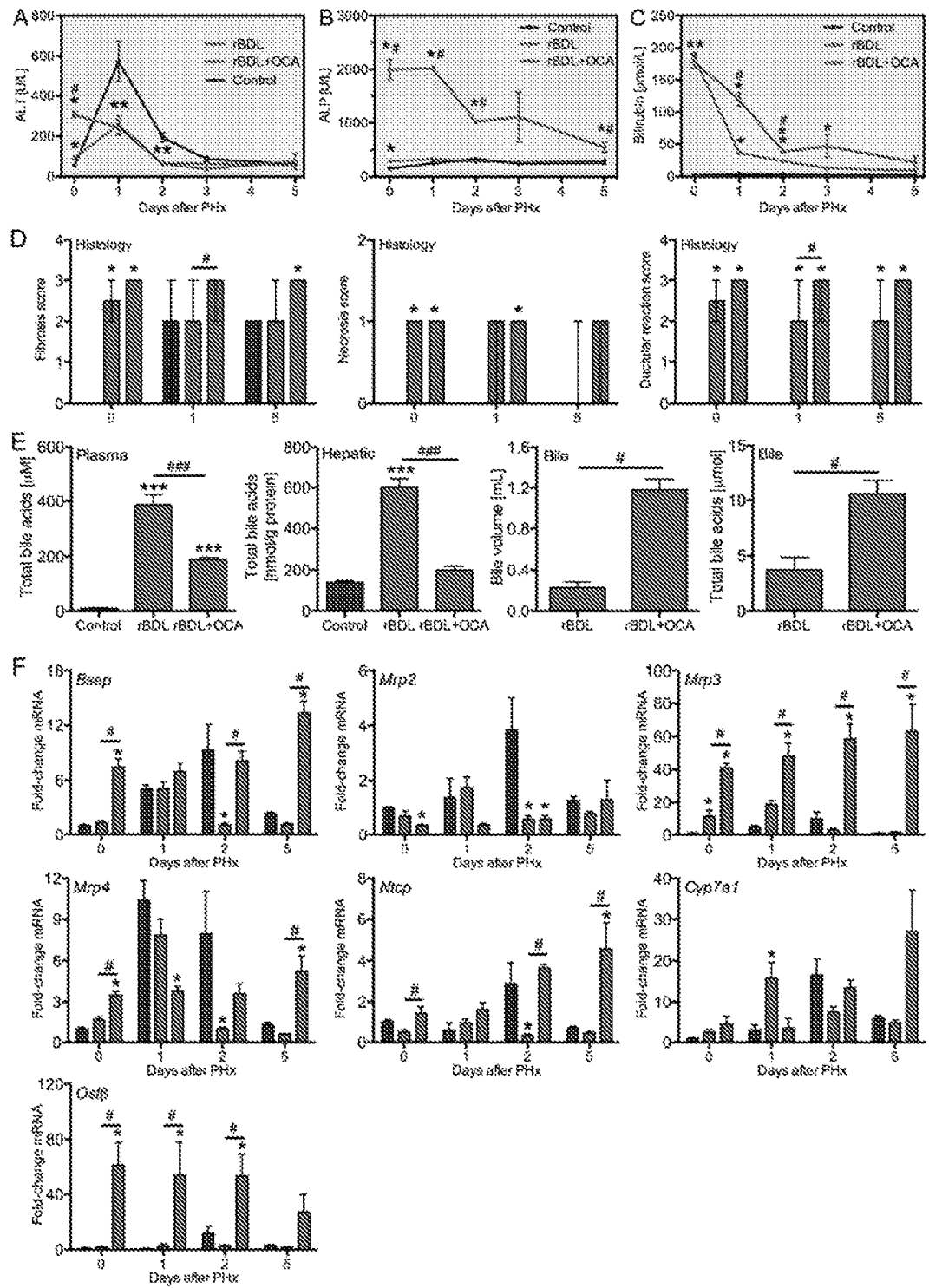
FIG. 21 shows effect of OCA on cholestatic injury through Bsep-mediated bile acid.
Figure 22:
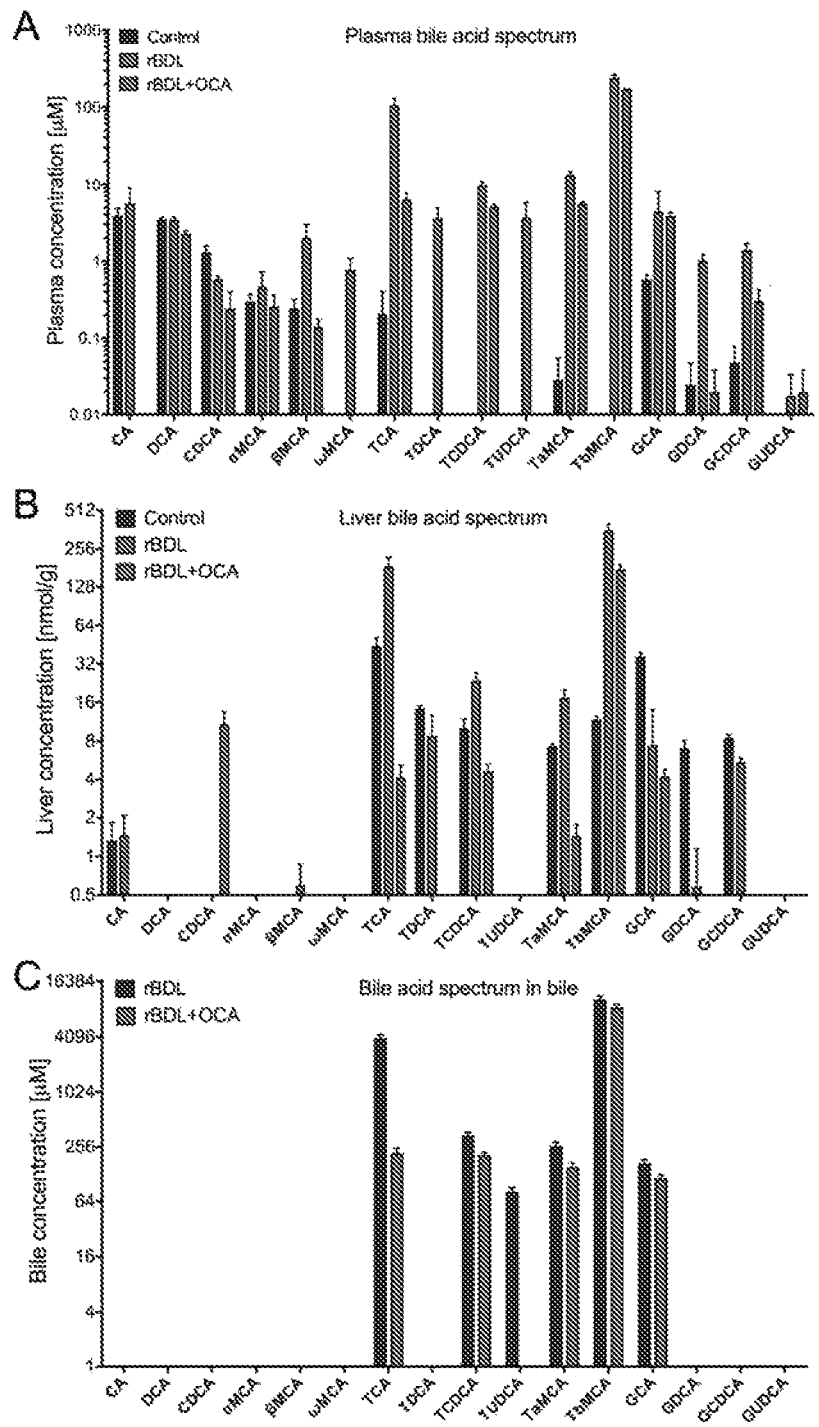
FIG. 22 shows the influence of obstructive cholestasis and obeticholic acid treatment on the bile acid pool composition of plasma, liver, and bile in rats.

As shown in FIG. 21, ALT (A), ALP (B), and bilirubin levels (C) in plasma obtained before (t=0) and after partial hepatectomy (PHx) in controls rats (Control line), and (post)cholestatic rats left untreated (rBDL line) or receiving obeticholic acid (OCA, rBDL-OCA line). Histologic scoring of liver sections shown as mean score+range (D). The scoring system and representative images are shown in Table 1 and FIG. 20. Total bile acid (BA) level of plasma, liver tissue, and biliary BA output prior to PHx (E). The total BA data for the control and rBDL groups were also published in an earlier report [Lionarons 2016]. Expression of genes related to hepatocyte BA homeostasis (F). Group color coding in (F) is similar to (A-E). (Abbreviations: ALP=alkaline phosphatase; ALT=alanine aminotransferase; rBDL=reversible bile duct ligation (cholestasis); OCA=obeticholic acid. * indicates p<0.05 versus the control group and # signifies p<0.05 versus the experimental group indicated by the solid line).

Discussion

Impaired liver regeneration remains a serious risk for patients with parenchymal liver disease that undergo major liver surgery. The data presented here indicate that the Fxr agonist OCA may be used to improve the surgical management of cholestatic patients. Most importantly, OCA triggered the growth of cholestatic rat livers prior to PHx. A similar increase in liver size was observed in healthy mice fed a cholic acid-containing diet, but was not seen in Fxr knock-out animals [Huang 2006]. This indicates that Fxr (agonists) can stimulate liver growth in absence of established mitogenic triggers such as PHx. Although the underlying mechanism is incompletely understood, BAs appear to be able to alter liver size. It was recently shown that unrestrained BA synthesis and the consequent rise in circulating BAs increased the size of humanized mouse livers by ~3-fold [Naugler 2015]. It is however questionable whether an expanded BA pool by itself is sufficient to trigger hepatocyte proliferation, as BDL also increases systemic BA levels but does not induce liver growth, possibly due to the lack of intestinal Fxr stimulation under BDL conditions. The correction for hepatic water content seems important in that respect, as gross liver mass increases following BDL in rats as well as mice [Modica 2012], indicating that the increase in wet liver mass likely represents an inflammatory artifact (e.g. edema).

As Fxr is expressed at both ends of the gut-liver axis, it is precarious to discern whether the effects of OCA on liver growth originate in the liver and/or the small intestine. Our transcriptional analyses point towards the latter, as the strong induction of intestinal Fxr targets such as Fgf15 was coupled to activation of the proliferative hepatic Fgfr4-Stat3 pathway [Kong 2014; PadrissaAltés 2015]. The effect of OCA on the expression of hepatic Fxr targets such as Ntcp and Cyp7a1 was less clear. The apparent importance of intestinal Fxr in driving liver growth is supported by studies stating that Fgf15 is indispensable for liver regeneration after PHx [Uriarte 2013; PadrissaAltés 2015], whereas the selective genetic deletion of hepatocyte Fxr only slightly delays regeneration [Borude 2012]. Further defining the relative contribution of intestinal and hepatic Fxr to liver regeneration is also exacted in light of the increase in biliary injury caused by OCA during rBDL (discussed below). The recently developed FGF19 analog M70 could be used to circumvent this drawback of hepatic Fxr stimulation during obstructive cholestasis. Although the anticipated effect of engineered FGF19 on liver growth remains to be experimentally proven, M70 reduces liver injury in Mdr2$^{-/-}$ and in BDL mice [Zhou 2015; Luo 2014], and suppresses BA synthesis in healthy volunteers [Luo 2014].

The current experiments cannot determine whether OCA is also able to accelerate liver regeneration after PHx, considering that the post-PHx liver mass recovery is strongly influenced by pre-resection hepatomegaly in the OCA group. The differences in liver size and downregulation of Fgfr4 blunt the proliferative response [Yamanaka 1993] and may even direct the mode of regeneration towards hypertrophy instead of proliferation [Miyaoka 2012], thereby preventing an accurate and reliable comparison with regeneration dynamics in the other groups. In light of translatability, the ability to increase liver size before surgery is more appealing than accelerating the growth of a small liver remnant.

PHx and biliary drainage were performed simultaneously in this model, whereas PHC patients usually undergo biliary drainage several weeks prior to surgery, to allow the liver to recover from the cholestatic hit. The increase in biliary injury seen in cholestatic animals treated with OCA, which has also been observed with other choleresis-inducing compounds such as oltipraz [Weerachayaphorn 2014] and ursodeoxycholic acid [Fickert 2002], likely causes little harm in the setting of pre-operative biliary drainage. This premise is corroborated by the rapid normalization of injury markers during the regeneration phase, and the therapeutic success of OCA in treating cholestatic conditions with an incomplete obstruction of bile flow such as primary biliary cirrhosis [Hirschfield 2014]. Considering the strong induction of BA exporters, it is conceivable that OCA could even expedite BA clearance following biliary drainage. If so, OCA might reduce drainage-associated complications such as cholangitis [Yokoyama 2014] by narrowing the interval between drainage and surgery. The notion that Fxr agonists such as ursedeoxycholic acid also augment biliary innate immune function could further suppress drainage-related complications [Daldebert 2009]. Temporally separating biliary decompression and liver resection in an animal model would also limit the influence of parameters such as inflammation, edema, and nutritional status on liver and body weight after resection, which could not be discounted in the current work.

OCA has been exclusively used to treat patients with benign disorders such as non-alcoholic steatohepatitis [NeuschwanderTetri 2014]. The vast majority of patients who would benefit from the effects of OCA on liver growth, however, suffer from a hepatobiliary malignancy. All proliferative interventions carry the risk of inducing tumor progression as side effect, as was demonstrated earlier for PVE [Hoekstra 2012b; Simoneau 2015; Kokudo 2001]. The potential effect of OCA on malignancies may differ per cancer type. On the one hand, the FXR target Fgf15 seems to expedite the growth of FGFR$_4$-positive hepatocellular carcinomas [Ho 2009]. On the other hand, FXR suppresses the growth of PHC [Dai 2011] and colorectal cancer [Modica 2008]. Preliminary safety studies indicate that 2 years of high-dose treatment (25 mg/kg) does not lead to malignant transformation in mice (Adorini L., Intercept Pharmaceuticals).

The invention claimed is:

1. A method of accelerating, promoting or increasing hepatic regeneration in a subject with reduced liver function, comprising administering to the subject a therapeutically effective amount of a compound of formula (A):

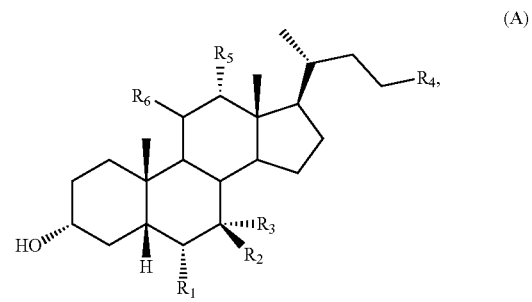

(A)

or a pharmaceutically acceptable salt thereof, wherein:
$R_1$ is hydrogen or $C_1$-$C_6$ alkyl;
$R_2$, $R_3$, and $R_5$ are each independently hydrogen or hydroxyl;
$R_6$ is hydrogen;
$R_4$ is $CO_2H$, $C(O)NH(CH_2)_mSO_3H$, $C(O)NH(CH_2)_nCO_2H$, or $OSO_3H$; and
m and n are each independently 1, 2, or 3.

2. The method of claim 1, wherein $R_4$ is $CO_2H$ or $OSO_3H$.

3. The method of claim 1, wherein $R_1$ is methyl, ethyl or propyl and $R_5$ is hydrogen.

4. The method of claim 1, wherein $R_2$ is hydrogen and $R_3$ is hydroxyl.

5. The method of claim 1, wherein the compound is

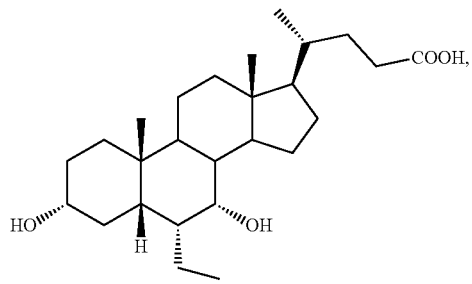

or a pharmaceutically acceptable salt thereof.

6. The method of claim 1, wherein the compound is

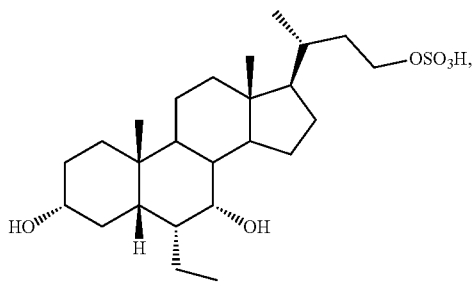

or a pharmaceutically acceptable salt thereof.

7. The method of claim 1, wherein the compound is a pharmaceutically acceptable salt.

8. The method of claim 6, wherein the salt is a sodium or triethylammonium salt.

9. The method of claim 1, wherein the subject has a transplanted liver.

10. The method of claim 1, wherein the subject has a resected liver.

11. The method of claim 1, wherein the reduced liver function is the result of surgical operation, disease, pathological condition, or injury.

12. The method of claim 11, wherein the reduced liver function is the result of surgical operation.

13. The method of claim 12, wherein the surgical operation is hepatic arterial embolization or portal venous manipulations.

14. The method of claim 12, wherein the surgical operation is partial hepatectomy.

15. The method of claim 12 wherein the compound is administered prior to or after the surgical operation, or in combination.

16. The method of claim 11, wherein the reduced liver function is the result of a disease or pathological condition selected from cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, liver transplant associated graft versus host disease, congenital hepatic fibrosis, choledocholithiasis, granulomatous liver disease, Sjogren's syndrome, sarcoidosis, Wilson's disease, Gaucher's disease, hemochromatosis, and alpha 1-antitrypsin deficiency.

17. The method of claim 11, wherein the reduced liver function is the result of a disease or condition is selected from hepatocellular carcinoma, intrahepatic malignancy and extrahepatic malignancy.

18. The method of claim 11, wherein the reduced liver function is the result of an injury selected from drug-induced injury or physical injury.

19. A method of increasing liver mass in a subject with reduced liver function, comprising administering to the subject a therapeutically effective amount of a compound of formula (A):

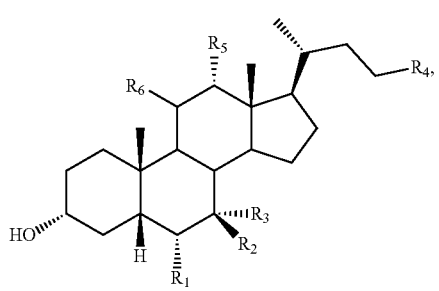

or a pharmaceutically acceptable salt thereof, wherein:
$R_1$ is hydrogen or $C_1$-$C_6$ alkyl;
$R_2$, $R_3$, and $R_5$ are each independently hydrogen or hydroxyl;
$R_6$ is hydrogen;
$R_4$ is $CO_2H$, $C(O)NH(CH_2)_mSO_3H$, $C(O)NH(CH_2)_nCO_2H$, or $OSO_3H$; and
m and n are each independently 1, 2, or 3.

* * * * *